United States Patent
Avneri et al.

(10) Patent No.: US 9,439,653 B2
(45) Date of Patent: Sep. 13, 2016

(54) DEVICES AND METHODS FOR ENDOVASCULAR ACCESS AND THERAPY

(71) Applicants: Itzhak Avneri, Tel Aviv-Yafo (IL); Ben-Ami Avneri, Moshav Udim (IL); Shahar Avneri, Herzliya (IL); Lior Avneri, New York, NY (US)

(72) Inventors: Itzhak Avneri, Tel Aviv-Yafo (IL); Ben-Ami Avneri, Moshav Udim (IL); Shahar Avneri, Herzliya (IL); Lior Avneri, New York, NY (US)

(73) Assignee: TRAUMATEK SOLUTIONS B.V., Tel Aviv (IL)

( * ) Notice: Subject to any disclaimer, the term of this patent is extended or adjusted under 35 U.S.C. 154(b) by 571 days.

(21) Appl. No.: 13/708,878

(22) Filed: Dec. 7, 2012

(65) Prior Publication Data
US 2013/0178711 A1    Jul. 11, 2013

Related U.S. Application Data

(60) Provisional application No. 61/568,111, filed on Dec. 7, 2011, provisional application No. 61/612,334, filed on Mar. 18, 2012.

(51) Int. Cl.
*A61B 17/12* (2006.01)
*A61M 25/01* (2006.01)
*A61M 25/06* (2006.01)
(Continued)

(52) U.S. Cl.
CPC ... *A61B 17/12109* (2013.01); *A61B 17/12031* (2013.01); *A61B 17/3403* (2013.01); *A61M 25/0105* (2013.01); *A61M 25/065* (2013.01); *A61B 17/1214* (2013.01); *A61B 17/12136* (2013.01); *A61B 17/12168* (2013.01); *A61B 2017/00022* (2013.01); *A61B 2034/2072* (2016.02); *A61M 25/0127* (2013.01); *A61M 25/09041* (2013.01); *A61M 2025/0024* (2013.01); *A61M 2025/1052* (2013.01)

(58) Field of Classification Search
CPC ............ A61B 2017/00672; A61B 2017/3405; A61B 2017/00022; A61B 17/3403; A61B 2025/0024; A61B 25/09041
See application file for complete search history.

(56) References Cited

U.S. PATENT DOCUMENTS

| | | |
|---|---|---|
| 4,671,287 A | 6/1987 | Fiddian-Green |
| 4,721,123 A | 1/1988 | Cosentino et al. |

(Continued)

FOREIGN PATENT DOCUMENTS

| | | |
|---|---|---|
| EP | 0832663 A2 | 4/1998 |
| WO | WO-2008/137956 A2 | 11/2008 |

(Continued)

OTHER PUBLICATIONS

Notification of Transmittal, International Search Report, and Written Opinion for International Application No. PCT/US2013/032641 (Aug. 6, 2013).

(Continued)

*Primary Examiner* — Alexander Orkin
(74) *Attorney, Agent, or Firm* — Venable LLP; Michele V. Frank

(57) ABSTRACT

The present invention provides for devices and methods for providing endovascular therapy, including facilitating establishment of vascular access, placement of endovascular sheaths, catheter tip localization, and administration of vascular occlusion. The inventions includes a vessel cannulation device, an expandable sheath, an occlusion catheter, and a localizer each of which may be provided separately or used as part of a system.

26 Claims, 41 Drawing Sheets

(51) Int. Cl.

| | | |
|---|---|---|
| A61B 17/34 | (2006.01) | |
| A61M 25/09 | (2006.01) | |
| A61M 25/00 | (2006.01) | |
| A61M 25/10 | (2013.01) | |
| A61B 17/00 | (2006.01) | |

(56) References Cited

U.S. PATENT DOCUMENTS

| | | |
|---|---|---|
| 4,917,094 A | 4/1990 | Lynch et al. |
| 5,256,150 A | 10/1993 | Quiachon et al. |
| 5,312,361 A | 5/1994 | Zadini et al. |
| 5,318,588 A | 6/1994 | Horzewski et al. |
| 5,320,611 A | 6/1994 | Bonutti et al. |
| 5,335,551 A | 8/1994 | Ohnishi et al. |
| 5,415,177 A | 5/1995 | Zadini et al. |
| 5,480,388 A | 1/1996 | Zadini et al. |
| 5,527,290 A | 6/1996 | Zadini et al. |
| 5,527,291 A | 6/1996 | Zadini et al. |
| 5,579,780 A | 12/1996 | Zadini et al. |
| 5,749,371 A | 5/1998 | Zadini et al. |
| 5,749,835 A | 5/1998 | Glantz |
| 5,944,691 A | 8/1999 | Querns et al. |
| 5,997,508 A | 12/1999 | Lunn et al. |
| 6,115,624 A | 9/2000 | Lewis et al. |
| 6,197,001 B1 | 3/2001 | Wilson et al. |
| 6,217,558 B1 | 4/2001 | Zadini et al. |
| 6,245,052 B1 | 6/2001 | Orth et al. |
| 6,263,230 B1 | 7/2001 | Haynor et al. |
| 6,626,869 B1 | 9/2003 | Bint |
| 6,692,462 B2 | 2/2004 | Mackenzie et al. |
| 6,827,710 B1 | 12/2004 | Mooney et al. |
| 7,197,354 B2 | 3/2007 | Sobe |
| 7,343,195 B2 | 3/2008 | Strommer et al. |
| 7,449,011 B2 | 11/2008 | Wenchell et al. |
| 7,753,887 B2 | 7/2010 | Botich et al. |
| 7,766,820 B2 | 8/2010 | Core |
| 7,881,769 B2 | 2/2011 | Sobe |
| 7,927,309 B2 | 4/2011 | Palm |
| 8,313,493 B2 | 11/2012 | Fischer |
| 2001/0023334 A1 | 9/2001 | St. Goar et al. |
| 2002/0183781 A1 | 12/2002 | Casey et al. |
| 2003/0073955 A1 | 4/2003 | Otawara |
| 2004/0059179 A1 | 3/2004 | Maguire et al. |
| 2005/0075606 A1* | 4/2005 | Botich et al. .......... 604/110 |
| 2006/0106336 A1 | 5/2006 | Saab |
| 2006/0116633 A1 | 6/2006 | Shachar |
| 2007/0185380 A1 | 8/2007 | Kucklick |
| 2008/0004571 A1 | 1/2008 | Voss |
| 2008/0058836 A1 | 3/2008 | Moll et al. |
| 2008/0132911 A1 | 6/2008 | Sobe |
| 2008/0147002 A1 | 6/2008 | Gertner |
| 2008/0221593 A1 | 9/2008 | Liddicoat et al. |
| 2009/0156926 A1 | 6/2009 | Messerly et al. |
| 2009/0240202 A1 | 9/2009 | Drasler et al. |
| 2009/0287182 A1 | 11/2009 | Bishop et al. |
| 2009/0287223 A1 | 11/2009 | Pua et al. |
| 2010/0049062 A1 | 2/2010 | Ziv |
| 2010/0130937 A1 | 5/2010 | Voss |
| 2010/0198159 A1 | 8/2010 | Voss et al. |
| 2010/0198160 A1 | 8/2010 | Voss |
| 2010/0204613 A1 | 8/2010 | Rollins et al. |
| 2010/0234873 A1 | 9/2010 | Nagano et al. |
| 2010/0274178 A1 | 10/2010 | LePivert |
| 2011/0152836 A1 | 6/2011 | Riopelle et al. |
| 2011/0190697 A1 | 8/2011 | Farnan |
| 2012/0190981 A1 | 7/2012 | Harris et al. |
| 2015/0065916 A1 | 3/2015 | Maguire et al. |

FOREIGN PATENT DOCUMENTS

| | | |
|---|---|---|
| WO | WO-2010/036560 A1 | 4/2010 |
| WO | 2010/056538 A1 | 5/2010 |
| WO | 2012/088471 A1 | 6/2012 |
| WO | 2015/031481 A1 | 3/2015 |

OTHER PUBLICATIONS

Assar, A.N. et al., "Endovascular proximal control of ruptured abdominal aortic aneurysms: the internal aortic clamp," *J Cardiovasc Surg (Torino)*, 2009; 50:381-5.

Avaro, J.-P. et al., "Forty-Minute Endovascular Aortic Occlusion Increases Survival in an Experimental Model of Uncontrolled Hemorrhagic Shock Caused by Abdominal Trauma," *Journal of Trauma-Injury Infection & Critical Care*, 2011; 71:720-726.

Bell-Thomas, S.M. et al., "Emergency use of a transfemoral aortic occlusion catheter to control massive haemorrhage at caesarean hysterectomy," *BJOG*, 2003;110:1120-2.

Blackbourne, L. H. et al., "Exsanguination Shock: The Next Frontier in Prevention of Battlefield Mortality," *Journal of Trauma-Injury Infection & Critical Care*, 2011; 7:S1-S3.

Champion H.R., et al., "A profile of combat injury," *A. J Trauma*, 2003; 54(5 Suppl):S13-9.

Cothren C.C. and Moore, E. A.,"Emergency department thoracotomy for the critically injured patient: Objectives, indications, and outcomes," *World J Emerg Surg.*, 2006;1:4.

Edens, J.W. et al., "Longterm outcomes after Combat Casualty Emergency Department Thoracotomy," *J Am Coll Surg.*, 2009; 209(2):188-97.

Martinelli, T et al. "Intra-aortic balloon occlusion to salvage patients with life-threatening hemorrhagic shocks from pelvic fractures," *J Trauma*, 2010; 68(4):942-8.

Rabinovici R., et al., "Control of bleeding is essential for a successful treatment of hemorrhagic shock with 7.5 per cent sodium chloride solution," *Surg Gynecol Obstet.* 1991; 173(2):98-106 (Abstract only).

Tang, X et al. "Use of Aortic Balloon Occlusion to Decrease Blood Loss During Sacral Tumor Resection", *The Journal of Bone & Joint Surgery*, 2010; 92:1747-1753.

White, J.M. et al., "Endovascular balloon occlusion of the aorta is superior to resuscitative thoracotomy with aortic clamping in a porcine model of hemorrhagic shock," *Surgery*, 2011; 150:400-9.

Boctor, E., et al., "Three-dimensional ultrasound-guided robotic needle placement: an experimental evaluation", Int J Med Robot. Jun. 2008; 4(2): 180-191.

Perry, S., Making a robot that can draw blood faster and more safely than a human can, IEEE Spectrum, Jul. 26, 2013, available online at <http://spectrum.ieee.org/robotics/medical-robots/profile-veebot> (last accessed Jun. 22, 2015).

Saito, H., et al., "Detection of needle puncture to blood vessel using puncture force measurement", Medical and Biological Engineering and Computing , 2005, vol. 43, Issue 2, pp. 240-244 (Abstract only).

Zivanovic, A., et al., "A robotic system for blood sampling", IEEE Trans Inf Technol Biomed., Mar. 2000;4(1):8-14 (Abstract only).

Cincinati Children's Hospital Press Release, "International Collaborative Funds Three Early-Stage Pediatric Medical Device Concepts", Dec. 21, 2012, available online at <http://www.cincinnatichildrens.org/news/release/2012/bgu-cincinnati-childrens-collaboration-12-21-2012/> (last accessed Jun. 22, 2015).

VenousPro Product Description, Vasculogic, LLC, 2010, available online at <http://vasculogic.com/venouspro.html>, (last accessed Jun. 22, 2015).

Veebot: Automated Venipuncture Product Description, Veebot LLC, 2014, available online at <http://www.veebot.com/solutions.html> (last accessed Jun. 22, 2015).

Extended European Search Report in European Patent Application No. 13764355.7 dated Sep. 28, 2015.

* cited by examiner

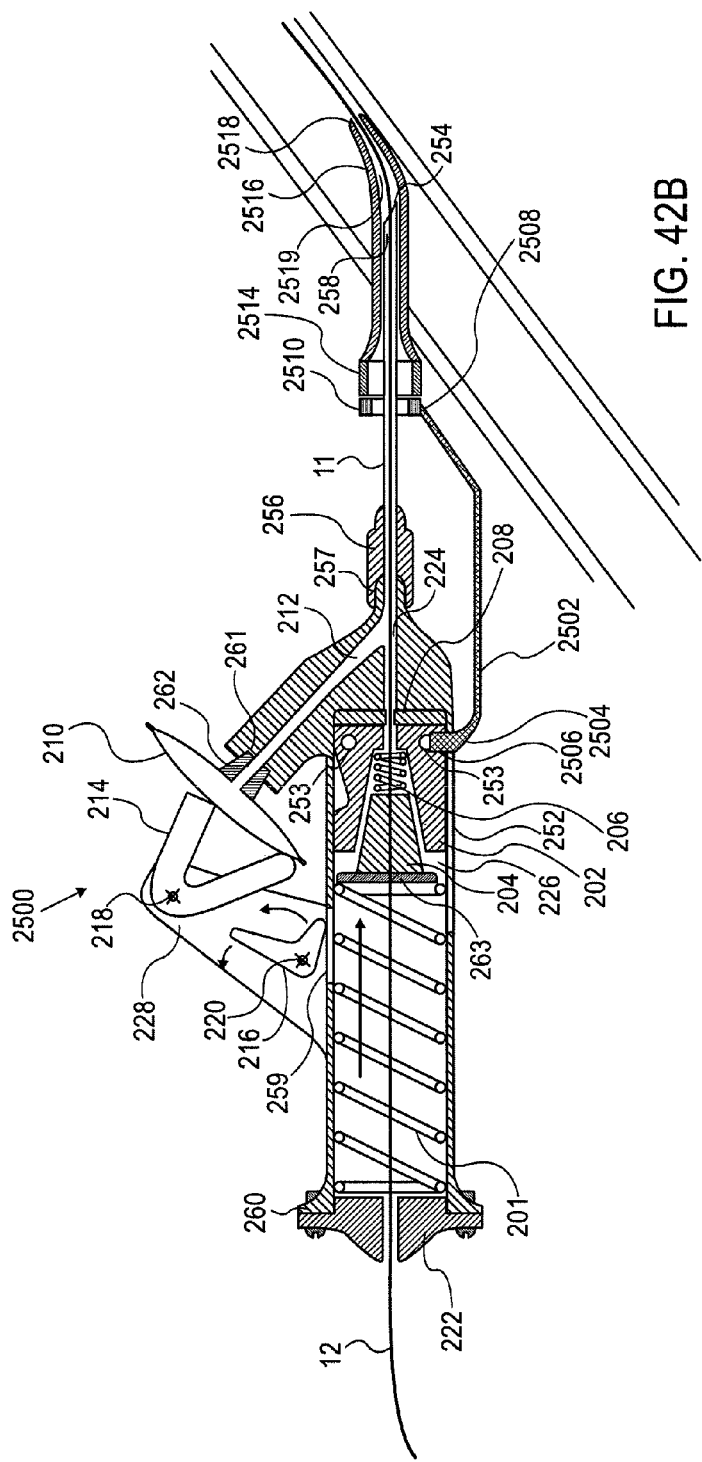

DEVICES AND METHODS FOR ENDOVASCULAR ACCESS AND THERAPY

CROSS-REFERENCE TO RELATED APPLICATIONS

This application claims priority to U.S. Provisional Application 61/568,111 (filed on Dec. 7, 2011) and U.S. Provisional Application No. 61/612,334 (Mar. 18, 2012), the disclosures of which are incorporated by reference in their entireties.

FIELD OF THE INVENTION

The invention relates to devices and methods for providing endovascular therapy, including facilitating establishment of vascular access, placement of endovascular sheaths, catheter tip localization, and administration of vascular occlusion.

BACKGROUND OF THE INVENTION

I. Clinical Need

General:

Vascular access is a crucial element of medical therapy in a vast majority of clinical settings and procedures. This is true in both elective and in emergent situations. In a specific type of emergency, hemorrhagic shock, there may further be a need to perform aortic occlusion. Both these clinical needs, vascular access and aortic occlusion, are the subject of the current invention.

Vascular Access:

A large part of medical interventions, both elective and emergent, are endovascular procedures. These procedures have become very common and continue to grow in numbers due to both the increase in cardiovascular patient absolute numbers and to the trend of shifting from open surgery to endovascular surgery.

Once vascular access is secured, delivery of treatment is quick and easy, be it the administration of fluids, analgesics, sedative medications, vasopressors, inotropics, percutaneous endovascular trans-catheter treatments or other interventions. Patient monitoring is also aided by central vascular access, as it enables direct arterial or venous pressure measurements and blood sampling.

Vascular Access in Elective Situations:

Although extremely common, the ways to establish vascular access remain very basic and are often inadequate. This is especially unfortunate in elective settings, as it is those older and sicker individuals who usually have more "difficult blood vessels", and must frequently endure additional suffering caused by painful repeated attempts at blood vessel cannulation, even when performed by experienced personnel.

Vascular Access in Emergency Situations:

In emergency situations, the importance of vascular access is increased, as stabilization of patients often requires administration of fluids or blood and medications. However the emergency setting also increases the obstacles to successful blood vessel cannulation. Possible impediments include environmental factors such as darkness (night), cold and wet weather, unstable surroundings (wind, waves, bumpy vehicle or aircraft), patient factors such as shock which may cause collapse of veins and an inpalpable arterial pulse, burns, or movements due to shivering or convulsions, care provider factors such as stress caused by the need to deliver therapy urgently in a dying patient, additional patients, imminent danger from warfare or natural hazards, or lack of expertise, and finally equipment factors such as the absence of expensive ultrasound guidance. A venous cut down may be performed using simple tools by an experienced physician, but this too takes time and requires certain expertise, making it impractical in many cases.

Aortic Occlusion:

Massive hemorrhage remains the major cause of death in the battlefield. Approximately 50% of combat deaths are due to exsanguinating hemorrhage, and 80% of these are from noncompressible torso injuries. Champion H. R., et al., "A profile of combat injury," *A. J Trauma*, 2003; 54(5 Suppl): S13-9; Blackbourne, L. H. et al., "Exsanguination Shock: The Next Frontier in Prevention of Battlefield Mortality," *Journal of Trauma-Injury Infection & Critical Care*, 2011; 7:S1-S3. The pathophysiology of death in these cases involves incompletely understood cellular, inflammatory, and hematologic pathways. Blackburne et al. Whatever the processes involved, large volume blood loss is a major factor, and more effective control of hemorrhage is key to improving outcomes. Rabinovici R., et al., "Control of bleeding is essential for a successful treatment of hemorrhagic shock with 7.5 percent sodium chloride solution," *Surg Gynecol Obstet.* 1991; 173(2):98-106. Clearly, new modalities of treatment for exsanguination shock are required.

II. Current Practice

Current Practice of Vascular Access:

In performing an endovascular procedure, access into the vasculature must be established and maintained for the duration of the procedure. This is most commonly done by placing an introducer sheath in the blood vessel to enable passage of the interventional instruments in and out without losing the entry point or causing damage to the vessel.

Placement of an endovascular sheath is usually performed using the modified Seldinger technique. This entails puncture of the vessel with a needle, passage of a guide-wire through the needle, removal of the needle, incision of the skin, placement of a sheath with a dilator in it over the guide-wire, removal of the guide-wire and dilator.

The Seldinger technique, although useful, suffers from several drawbacks. First, it requires significant experience in order to be successfully performed, especially when circumstances are suboptimal such as in emergency and trauma situations. As it is mainly used for placement of large bore catheters, which are less common than regular small-medium bore venous catheters, the exposure to it (and hence the procedure practice) is less than that of over the needle venous catheter placement. Second, there are several points during the procedure which may lead to its failure.

One such point is after entry of the needle into the blood vessel, which is evident by the flow of blood out of the needle. At this point, the physician must thread a guide-wire into the needle. Holding the needle absolutely still, while bringing the guide-wire and threading it with the other hand requires a certain level of coordination, which not all physicians possess. Even the slightest movement of the needle at this stage might cause it to move forward and exit the artery through its posterior wall, or withdraw out of the lumen through the anterior wall of the artery. This will prevent the guide wire from entering the lumen and will require an additional puncture attempt. Additionally, this might cause blood to leak around the vessel causing an internal hematoma, which might compress the vessel and make repeat cannulation more difficult. Worse yet, unintended movement of the needle might place it within one of the arterial walls, and attempted insertion of the guide wire can then damage the arterial wall, possibly leading to large hematomas or other complications.

Another sensitive point in the procedure is after the guide-wire insertion and needle removal. The physician must now thread the guide-wire edge into the dilator, which has a very small aperture the size of the guide-wire, while at the same time compressing the puncture site to prevent hematoma and make sure the guide-wire is not pulled out. Exit of the guide-wire from the artery at this stage will cause the sheath to be placed into tissues instead of into the artery, which besides tissue damage usually causes the guide-wire to bend, necessitating its replacement.

Additional drawbacks of the Seldinger technique are related to the use of a long guide-wire, which carries with it an increased risk of contamination of its proximal end, as well as a danger of splashing blood at the physician. Also, during the time between needle entry into the vessel and until the guide-wire is inserted into it, either profuse bleeding or entry of air into the circulation might occur, depending on whether pressure within the vessel is higher or lower than ambient pressure.

In contrast to the above, regular small to medium bore venous cannulas are usually placed using the over the needle technique. With this technique, the cannula, which has an inner diameter ("ID") matched to the outer diameter ("OD") of the needle, is inserted into the artery together with the needle. When blood is observed in a "flash" chamber connected to the needle lumen, the needle is held in place and the cannula is manually advanced and slid over the needle into the vessel. Not only is this technique technically simpler than the Seldinger technique, it is also more commonly used, and there is a greater possibility of exposure to it for training, so the learning curve is significantly shorter and competence in it is easier to maintain.

In the "over-the-needle" method, the cannula must have an ID matched to the OD of the needle, in order for it to enter the vessel with the needle. Therefore, the diameters of cannulas inserted using this technique are limited to the outer diameters of needles that can be used for these purposes, which are usually 21 G-18 G (0.8 mm-1.3 mm.) Endovascular procedures often require insertion of instruments having ODs of 8 fr-14 fr (2 mm-4.6 mm) or more.

Since the "over-the-needle" technique is not adequate for placing large bore catheters or sheaths, the Seldinger technique is used in these cases, which as mentioned, include most endovascular interventions.

The WAND, manufactured by Access Scientific of San Diego, Calif., is a device intended to provide a solution for the above drawbacks of the Seldinger technique. This device includes a needle, guide-wire, dilator, and sheath in an all-in-one assembly, which is intended for easier and safer over-the-wire sheath insertion. Use of the WAND requires manual advancement of both the guidewire and the sheath by the operator. The WAND mainly addresses safety issues such as needle-stick injury and air embolism but the technique is still rather complicated and requires significant training.

Expandable sheaths were described in the art in various contexts, mainly for retrieval of large devices such as heart valve delivery systems, aortic balloon catheters etc. usually having a self-expanding and balloon expandable components. Such solutions are cumbersome and expensive and are not appropriate for direct over the needle vascular access.

Another drawback of existing sheaths related to their having a fixed diameter, is that the arterial puncture site remains dilated to the maximum size for the whole duration of the procedure. The duration of puncture site dilation is one of the factors affecting the chances of its closure. With the current invention, the artery would only be exposed to maximal dilation when the largest instruments are used, while during the rest of the procedure, it will be only slightly dilated. This will increase the successful closure rates and reduce puncture site complication rates.

It is therefore an aspect of the current invention to provide a simple, safe, easy to use, and low cost solution for establishing vascular access.

Current Practice of Aortic Occlusion

The currently accepted paradigm for trauma treatment is "scoop and run": patients are evacuated as soon as possible to a medical facility without wasting time on their stabilization, usually arriving within minutes. When a patient with penetrating trauma arrives at the Emergency Department ("ED") with recent loss of vital signs, Emergency Department Thoracotomy ("EDT") is indicated. EDT is a "last resort" procedure attempting temporary stabilization of patients to enable their rapid transfer to the operating room or angiography suite for administration of definitive care. The procedure involves an anterior lateral thoracotomy, which allows achieving the following objectives: (a) release pericardial tamponade; (b) control cardiac hemorrhage; (c) control intrathoracic bleeding; (d) evacuate massive air embolism; (e) perform open cardiac massage; and (f) temporarily occlude the descending thoracic aorta. Combined, these objectives attempt to address the primary issue of cardiovascular collapse from mechanical sources or extreme hypovolemia. Cothren C. C. and Moore, E. A., "Emergency department thoracotomy for the critically injured patient: Objectives, indications, and outcomes," *World J Emerg Surg.,* 2006; 1:4.

In cases of exsanguination due to extrathoracic penetrating torso trauma (i.e. abdominal, pelvic, junctional), the main reason to perform EDT is for aortic clamping. The rationale for temporary thoracic aortic occlusion in the patient with massive hemorrhage is two-fold. First, in patients with hemorrhagic shock, aortic cross clamping redistributes the patient's limited blood volume to the myocardium and brain. Second, patients sustaining intraabdominal injury may benefit from aortic cross clamping due to reduction in subdiaphragmatic blood loss.

Paradoxically, patients who undergo EDT because of shock due to penetrating cardiac injury, fare better (up to 50% survival rates, average 35%) than those with exsanguination shock due to all penetrating injuries (average survival 15%) or due to blunt trauma (2% survival). Cothren C. C. and Moore, E. A., "Emergency department thoracotomy for the critically injured patient: Objectives, indications, and outcomes," *World J Emerg Surg.,* 2006; 1:4. This may in part be because EDT is an aggressive procedure, and its invasive nature and associated morbidity limit its therapeutic potential.

Possible risks and complications of EDT include:
 technical complications which may include but are not limited to: unintentional injury to the heart, coronary arteries, aorta, phrenic nerves, esophagus, and lungs, avulsion of aortic branches to components of the mediastinum;
 compromised respiratory function;
 increased risk for hypothermia;
 recurrent chest bleeding;

infection of the pericardium, pleural spaces, sternum, and chest wall;

post-pericardiotomy syndrome; and high risk of personnel exposure to HIV or hepatitis.

III. Endovascular Aortic Occlusion (EAO)

Although first reported during the Korean war (Assar, A. N. et al., "Endovascular proximal control of ruptured abdominal aortic aneurysms: the internal aortic clamp," *J Cardiovasc Surg (Torino)*, 2009; 50:381-5), interest in EAO has re-emerged during the past decade as an alternative to EDT for hemorrhagic shock due to extrathoracic torso injuries.

Animal research provides support for this approach. A recent porcine study demonstrated improved survival with EAO compared to no occlusion. Avaro, J-P. et al., "Forty-Minute Endovascular Aortic Occlusion Increases Survival in an Experimental Model of Uncontrolled Hemorrhagic Shock Caused by Abdominal Trauma," *Journal of Trauma-Injury Infection & Critical Care*, 2011; 71:720-726. The superiority of EAO over open clamping for hemorrhagic shock was demonstrated in another recent study in a porcine model of hemorrhagic shock. EAO increased central perfusion pressures with less physiologic disturbance than thoracotomy with aortic clamping. White, J. M. et al., "Endovascular balloon occlusion of the aorta is superior to resuscitative thoracotomy with aortic clamping in a porcine model of hemorrhagic shock," *Surgery*, 2011; 150:400-9.

Use of EAO in humans for treatment or prevention of massive hemorrhage was described in various clinical situations such as blunt trauma with pelvic fractures (Martinelli, T et al. "Intra-aortic balloon occlusion to salvage patients with life-threatening hemorrhagic shocks from pelvic fractures," *J Trauma*, 2010; 68(4):942-8), ruptured abdominal aortic aneurysm (Cothren C. C. and Moore, E. A., "Emergency department thoracotomy for the critically injured patient: Objectives, indications, and outcomes," *World J Emerg Surg.*, 2006; 1:4), obstetric hemorrhage (Bell-Thomas, S. M. et al., "Emergency use of a transfemoral aortic occlusion catheter to control massive haemorrhage at caesarean hysterectomy," *BJOG*, 2003; 110:1120-2) and sacral tumor resection (Tang, X et al. "Use of Aortic Balloon Occlusion to Decrease Blood Loss During Sacral Tumor Resection", The Journal of Bone & Joint Surgery., 2010; 92:1747-1753) (see also FIG. 3).

The above-mentioned reports as well as other available data provide ample support for use of EAO to control acute massive extrathoracic hemorrhage.

When using traditional equipment, EAO requires experience with endovascular techniques as well as specialized equipment such as fluoroscopy, both of which are usually unavailable in the resource limited battlefield environment or even in the ED.

In one aspect of the invention tools, devices, systems and methods are provided which enable rapid, safe, and effective deployment of endovascular occlusion for controlling hemorrhagic shock at the point of injury. In an additional aspect of the invention, such tools, etc. would be easy to use for inexperienced personnel such as doctors who are unfamiliar with endovascular techniques, paramedics, and possibly battlefield medics. Another objective is to provide such devices that are relatively simple and cheap to manufacture.

It is therefore an additional aspect of the current invention to provide a simple, safe, easy to use, and low cost solution for the above need and for other applications.

SUMMARY OF THE INVENTION

In one aspect of the invention, devices and methods provide endovascular therapy, including facilitating establishment of vascular access, placement of endovascular sheaths, catheter tip localization, and administration of vascular occlusion.

In one aspect of the current invention, devices and methods are provided for facilitating vascular access and quick, safe, and easy deployment of temporary EAO in order to stop the hemorrhage and enable stabilization of the injured until definite treatment can be provided. Use of the current invention by trauma teams is expected to result in significant reductions in mortality related to traumatic hemorrhage.

Certain elements of the invention may also be utilized alone or in combination for other indications.

One embodiment of the invention is a vessel cannulation device including: a cannulation body having a distal end and proximal end, a pressure chamber, a guidewire lumen for passing a guidewire through it, a pressure sensor coupled to the pressure chamber; a guidewire advancing member configured for advancing a guidewire, wherein the guidewire advancing member is operably coupled to the pressure sensor; and a needle on a distal end of the device body and the needle is coupled to the pressure chamber, wherein the device is capable of advancing a guidewire in response to a fluid entering the pressure chamber. The pressure sensor may be a pressure operable diaphragm. The pressure operable diaphragm may be located on the exterior of the cannulation body and connected the pressure chamber. The pressure chamber may include a Y-shaped lumen on one end of which the pressure operable diaphragm is located. The pressure chamber may have a proximal and distal end and wherein the pressure chamber further includes a pressure gasket at the proximal end of the pressure chamber. The pressure gasket may have an opening for passing a guidewire through the cannulation device and wherein the pressure gasket is configured for sealantly surrounding a guidewire. The needle may be fluidly coupled to the pressure chamber and/or may include a lumen for passing a guidewire and fluid. The guidewire advancing member may be compressible such as e.g. a spring. The device may be provided with the guidewire advancing member compressed. When provided in such a fashion operation of the pressure sensor causes decompression of the device thereby advancing a guidewire. The device may also be adapted to receive bodily fluid through the needle into the anterior lumen. In one embodiment, a pressure is established in the pressure chamber and at a certain pressure, the pressure asserts pressure on the pressure operable diaphragm. This pressure in turn may operates a lever. The device may also include a guidewire. In another embodiment, the device further includes an expandable sheath disposed on the distal end of the device such as those described below.

In one embodiment, operation of the operable lever causes the lever to be no longer in contact with the guidewire member, thereby resulting in advancement of the guidewire through the device. In another embodiment, blood pressure operates the pressure operable diaphragm thereby advancing a guidewire.

The cannulation device may further include one or more side openings and/or a distal tip, which may be tapered. The cannulation device may also further include a backplate covering the device body at the proximal end of the device body having an opening configured for passing the needle. In other embodiments, the device may further include rollers for pushing the guidewire through the lumen of the device and/or an expandable sheath surrounding the needle. The pressure chamber may be partially prefilled with biologically acceptable fluid, which may shorten response time.

The guidewire advancing member may include a large compressible member and a small compressible member and wherein the device includes: the large compressible member in contact with a backplate configured for passing a guidewire through the cannulation device; a gripper in contact with the compressible member having an opening configured for passing a guidewire through the cannulation device; the small compressible member in contact with a gripper configured for passing a guidewire through the cannulation device; a slidable member having a proximal end, a distal end and an opening configured for passing a guidewire through the cannulation device, wherein the proximal end of the slidable member is configured to be in contact with and optionally surround the small flexible member, wherein the slidable member is positioned to be contact with the side opening of the cannulation device and wherein the slidable member is configured to accommodate a lever; and an operable lever positioned on the exterior of the device body configured to pass through the one side or more side opening and to contact the slidable member, wherein the lever is in contact with the pressure operable diaphragm;

Another embodiment is a kit including: the cannulation device; an expandable sheath; an occlusion catheter; and a tip localization device. The expandable sheath may include: a sheath hub having a through lumen, a distal tip and proximal end, wherein the through lumen is configured for passing a needle and a guidewire; and an expandable sheath shaft connected to the proximal end of the sheath hub, wherein the expandable sheath shaft has a lumen and is configured for passing a needle and guidewire; wherein the expandable sheath shaft has an exterior surface which includes one or more beams connected by one or more strips each running longitudinally along the exterior, wherein the one or more beams have a thickness greater than the one or more strips, and wherein the expandable sheath is configured to expand radially. The occlusion catheter may include: a catheter body having a working lumen and a balloon lumen and a distal tip; a magnet located towards the distal tip of the catheter body; and an inflatable balloon configured for passage through the balloon lumen, wherein the working lumen passes through the distal tip of the catheter body, and wherein the balloon lumen passes through a side of the catheter body at a location proximate to the magnet. This localization device includes one or more magnetic field detectors mounted on a support, wherein the device is configured for placement on the outside of a patient's body proximate to the target area of the catheter tip, wherein the one or more magnetic field detectors are capable of detecting the magnetic field emitted by the magnetic catheter tip inside the body of a patient and wherein the one or more magnetic field detectors visually indicate the proximity of the catheter tip. The tip of the localization device may be flexible.

Another embodiment of the invention is an expandable sheath including: a sheath hub having a through lumen, a distal tip and proximal end, wherein the through lumen is configured for passing a needle and a guidewire; and an expandable sheath shaft connected to the distal end of the sheath hub, wherein the expandable sheath shaft has a lumen and is configured for passing a needle and guidewire; wherein the expandable sheath shaft has an exterior surface which includes one or more beams connected by one or more strips each running longitudinally along the exterior, wherein the one or more beams have a thickness greater than the one or more strips, wherein the one or more beams and one or more strips include the same compliant material, and wherein the expandable sheath is configured to expand radially. The one or more beams may be configured to confer longitudinal rigidity to the shaft. Alternatively, the one or more strips may be configured to confer radial expandability to the shaft. The sheath shaft may be configured be expandable from the proximal end of the shaft to the distal end of the shaft. The expandable sheath shaft and/or the tip of the expandable sheath shaft may be tapered. The sheath shaft may also be curved. The tip may also be covered by a membrane.

The expandable sheath may have additional components including but not limited to (a) a hemostatic valve inside sheath hub, wherein the valve spans the lumen of the hub; (b) a needle hub adaptor to the sheath hub, wherein the needle hub adaptor is configured for connecting the sheath hub to the needle hub and for passing a needle; and/or (c) a fluid outlet connected to lumen of the sheath hub. The sheath may be configured for passage of a needle, and wherein the distal tip of the sheath has an inner diameter having a close tolerance fit of the needle. The sheath hub may have an inner diameter larger than the inner diameter of the expandable sheath shaft.

Another embodiment of the invention is an occlusion catheter including: a catheter body having a working lumen and a balloon lumen and a distal tip a magnet located towards the distal tip of the catheter body; and an inflatable balloon configured for passage through the balloon lumen, wherein the working lumen passes through the distal tip of the catheter body, and wherein the balloon lumen passes through a side of the catheter body at a location proximate to the magnet. The magnet may be a rare earth magnet. The balloon may be folded beyond the distal tip of the catheter to achieve low profile. The balloon may also further include a wire support, which may be coiled around the balloon, folded distal to distal catheter tip. The balloon may also further include a membrane support and may be configured to have a tubular shape continuous with the catheter tip, and wherein the balloon is further configured to be expandable under high pressure above 3 ATM. The balloon may also be movable. In one embodiment, the working lumen and a balloon lumen of the catheter are unitary.

Another embodiment of the invention is tip localization device including one or more magnetic field detectors mounted on a support, wherein the device is configured for placement on the outside of a patient's body proximate to the target area of the catheter tip, wherein the one or more magnetic field detectors are capable of detecting the magnetic field emitted by the magnetic catheter tip inside the body of a patient and wherein the one or more magnetic field detectors visually indicate the proximity of the catheter tip. The support may be flexible and the one or more magnetic field detectors may be arranged in an array. The array may include rows and columns of the one or more magnetic field detector which may be configured in arrays including from 3 to 8 rows by from 3 to 8 columns. The distance between the rows and columns of the one or more magnetic field detectors may vary. In one embodiment, the one or more magnetic field detectors include LED which light up when a magnetic field is detected. The flexible support may include a medically acceptable soft pad or cloth. The tip localization device may be configured to remain approximately flat on the patients' body and to prevent extreme overlap between detector fields.

The invention also encompasses a system for treating endovascular aortic occlusion including a vessel cannulation device, an expandable sheath, an occlusion catheter and a tip localization device of the invention. In addition, the invention also encompasses a system for performing hemorrhagic shock including a vessel cannulation device, an expandable sheath, an occlusion catheter and a tip localization device of the invention.

Yet another embodiment of the invention is a vessel cannulation device having a lumen, wherein the device is configured for automatically inserting guidewire or sheath in response fluid entering the entering lumen containing fluid at different pressure. Certain embodiments of the device may further include one or more of (1) a pressure sensor such as e.g. a diaphragm, (2) an automatic guidewire release mechanism, (3) a wheel mechanism for pushing a guidewire, (4) a needle and (5) an expandable sheath over the needle. The lumen of the device may be prefilled with a fluid for shortening response time.

Another embodiment of the invention is an expandable sheath including alternating longitudinal strips of single noncompliant material, wherein the rigid strips covered by compliant material, connected to each other at specific points. The sheath may have a directional preference to expand from one side. For example, the sheath expands from the proximal to the distal end. The expandable sheath may also include a curved tip or membrane cover tip.

An alternate embodiment of the invention is an occlusion catheter having a tip and a magnet at the tip. The magnet may be a rare earth magnet. The occlusion catheter may include a balloon starting at tip and folding beyond to achieve low profile. Alternatively, the occlusion catheter may further include a wire support or membrane support surrounding the balloon. The balloon may be configured to have a folded shape and be expandable in response to pressure. The occlusion catheter may also include lumen acting as a work-channel and balloon inflation lumen and/or a movable balloon.

Another aspect of the invention is a localizer including a soft pad with an array of magnetic field detectors. The localizer may include different distances between array rows and columns. The localizer may also include a support, which remains essentially straight on the patient's body to prevent extreme overlap between detector fields.

A system including a vessel cannulation device, an expandable sheath, an occlusion catheter, and a localizer.

A system for treating hemorrhagic shock including a vessel cannulation device, an expandable sheath, an occlusion catheter, and a localizer. The system may include a monitoring system, which may control balloon pressure such as intermittent deflations.

Additionally, the invention provides for a system for vascular access and aortic occlusion. Another embodiment is a device for vascular access including a needle gun having three dimensional ultrasound guidance. An alternate embodiment is a device access including multiple needles for identifying lumen penetration. Yet another embodiment is a ratchet based expandable vascular sheath. Another embodiment is a spiral based expandable vascular sheath. An alternate embodiment is an expandable vascular sheath comprising external cutting elements. Yet another embodiment is a low profile occlusion balloon catheter including a wire support. Another embodiment is a noninflatable occlusion catheter with umbrella like wireframe structure. An alternate embodiment, is a noninflatable occlusion catheter having loops in a wireframe structure. Yet another embodiment is a retractable tubular balloon occlusion catheter.

The invention also encompasses method of treating hemorrhagic shock and/or treating endovascular aortic occlusion via use of the above described vessel cannulation device, an expandable sheath, an occlusion catheter, and a localizer. In particular, the method of the invention rely on a pressure operated cannulation device to advance a guidewire into a vessel.

Accordingly, one embodiment is a method for treating hemorrhagic shock wherein the method includes use of a vessel cannulation device, an expandable sheath, an occlusion catheter, and a localizer. Another embodiment is a method for treating endovascular aortic occlusion including use of a vessel cannulation device, an expandable sheath, an occlusion catheter, and a localizer.

Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention and are incorporated in and constitute a part of this specification, illustrate preferred embodiments of the invention and together with the detailed description serve to explain the principles of the invention. In the drawings:

FIGS. 42A-D show various embodiments of a vessel cannulation device in accordance with the principles of the invention.

DETAILED DESCRIPTION

The invention is a system including ways for facilitating automatic access into the arterial system at the puncture site, placement of an expandable endovascular sheath, detection of the catheter tip location without fluoroscopy, and aortic occlusion. The system is designed to be used by personnel inexperienced with endovascular techniques and enables rapid, safe, and effective deployment of EAO for controlling hemorrhagic shock. Thus, it can function as a substitute for EDT, allowing cross-clamping without thoracotomy for extrathoracic non-compressible torso injuries.

Non-compressible torso hemorrhage remains the leading cause of potentially preventable death on the battlefield as well as in non-military trauma. A substantial body of evidence has established that endovascular aortic occlusion (EAO) is a viable treatment modality, which can improve outcomes in such cases. However, current aortic occlusion catheters are not adequately adapted to be used by non-expert physicians operating in the emergency setting.

The current invention provides devices and methods for facilitating vascular access and quick, safe, and easy deployment of temporary EAO in order to stop the hemorrhage and enable stabilization of the injured until definite treatment can be provided. Use of the current invention by trauma teams is expected to result in significant reductions in mortality related to traumatic hemorrhage. Certain elements of the invention may also be utilized alone or in combination for other indications. It is contemplated that this invention is also suitable for any endovascular occlusion procedure.

I. System

A preferred embodiment of the present invention includes a system having a device and or system and associated methods for insertion of a guidewire into the vascular system, an expandable sheath, an aortic occlusion catheter, and/or a tip localization device.

Figure 1A:
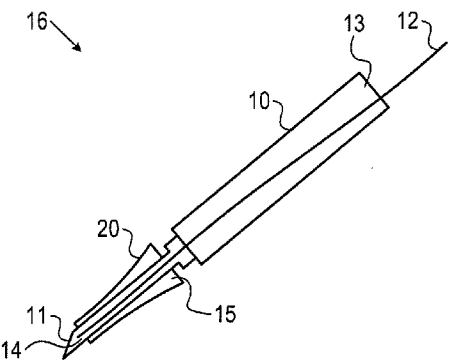
FIGS. 1A-C show a preferred embodiment of the complete system of the invention in accordance with the principles of the invention.
Figure 1B:
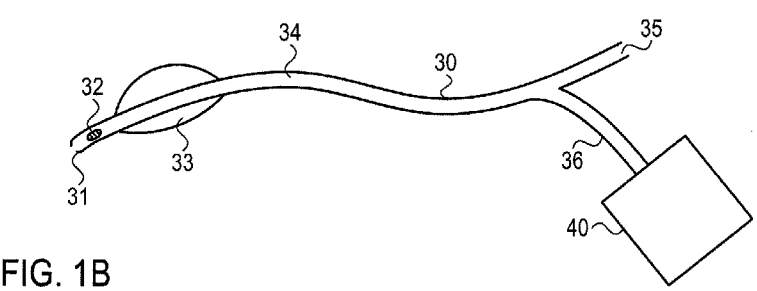
Figure 1C:
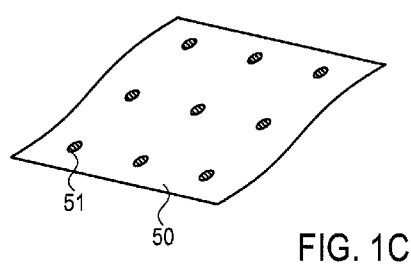

A schematic drawing of the system is seen in FIG. 1A-C. The system includes a vascular cannulation device 10, an expandable sheath 20, an occlusion catheter 30 and a localizer 50. More particularly, FIG. 1A shows assembly 16 including vascular cannulation device 10 having a needle 11 in fluid communication with the device, a guidewire 12 positioned within needle 11, and an expandable sheath 20 positioned over needle 11. The vascular cannulation device 10 has a lumen 13 through which guidewire 12 may pass. The needle 11 has a lumen 14 through which the guidewire 12 may pass. The expandable sheath 20 has a lumen 15 through which needle 11 and guidewire 12 may pass. FIG. 1B shows occlusion catheter 30 having tip 31, magnet 32 located adjacent tip 31, occluder 33 located adjacent magnet 32, catheter lumen 34 with an opening at distal tip and at least one proximal port 35 and 36, and monitor 40 optionally connected to port 36. FIG. 1C shows localizer 50 having multiple detectors 51.

Figure 2A:
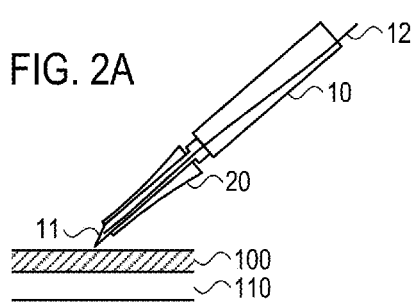
FIGS. 2A-K show the stages of use of the invention in accordance with the principles of the invention.
Figure 2B:
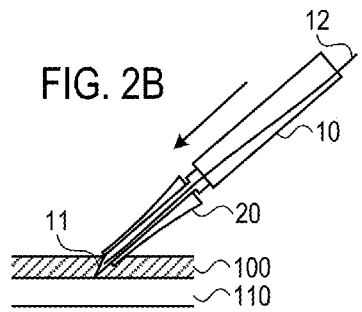
Figure 2C:
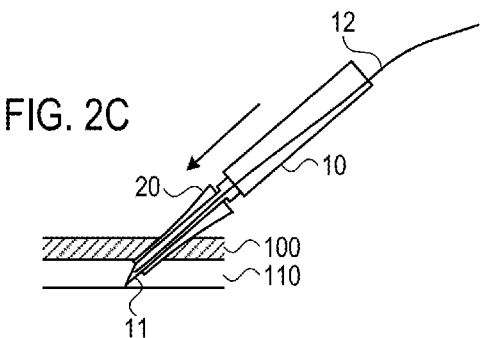
Figure 2D:
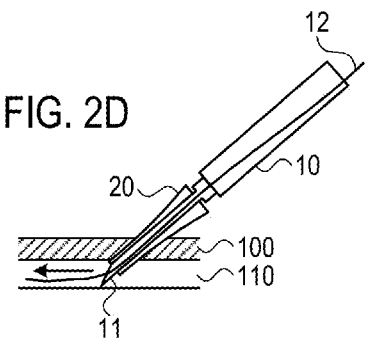
Figure 2E:
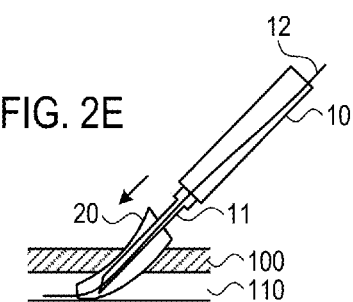
Figure 2F:
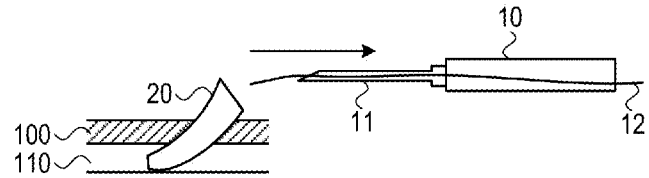

Typical use of the system is shown in FIGS. 2A-2K. More particularly, FIG. 2A shows vascular cannulation device 10 with needle 11, guidewire 12, and sheath 20 in proximity of tissue 100 over vessel 110. Vascular cannulation device 10 has a lumen 13 through which the guidewire 12 may pass. Needle 11 has a lumen 14 through which guidewire 12 may pass. Sheath 20 has a lumen 15 through which needle 11 and guidewire 12 may pass. Sheath 20 is positioned beyond the distal end of vascular cannulation device 10. Cannulation device 10 is advanced towards vessel 110 such that needle 11 together with sheath 20 penetrates tissue 100, as shown in FIG. 2B. With further advancement of cannulation device 10, needle 11 penetrates vessel 110 (FIG. 2C). This triggers a mechanism which is described below, within cannulation device 10, which pushes guidewire 12 forward through needle 11 into vessel 110 (FIG. 2D). Once pushed into the vessel 110, guidewire 12 acts as an anchor for needle 11, such that it cannot easily move inwards or outwards relative to the vessel and exit the vessel. The user then manually advances sheath 20 over needle 11 and guidewire 12, both acting as guides for sheath 20, through tissue 100 and into vessel 110 until it is well within the vessel and cannot be advanced further while holding cannulation device 10 together with needle 11 in place (FIG. 2E). Cannulation device 10 together with guidewire 12 and needle 11 are then removed from the vessel and tissue, leaving sheath 20 inside vessel 110 (FIG. 2F).

Once pushed out of the needle tip and into the vessel lumen, the guidewire straightens the vessel in the direction of the needle and prevents the needle from poking through the vessel. Thus, the guidewire "blunts" the needle. The degree to which the guidewire performs this depends on the vessel properties and on the guidewire's diameter, flexibility and rigidity, which depend on its material and specific design (braided, non-braided etc.). Importantly, the cannulation device may provide an indication that the vessel was entered, by the mere pushing forward of the guidewire as well as by an additional indication such as e.g a LED or sound. In one embodiment, the guidewire may be approximately 0.018 inch in diameter and may be stainless steel or nitinol guidewire and the needle may be an 18 fr 90 mm needle.

Figure 2G:
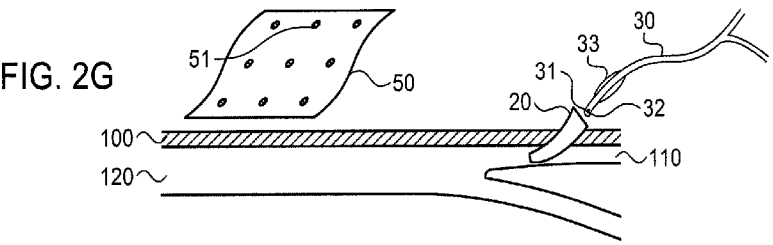
Figure 2H:
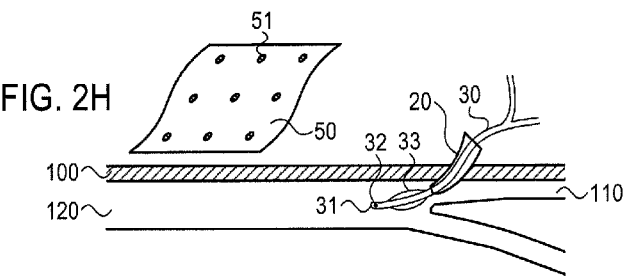
Figure 2I:
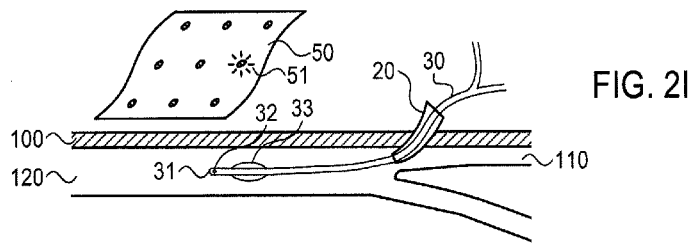
Figure 2J:
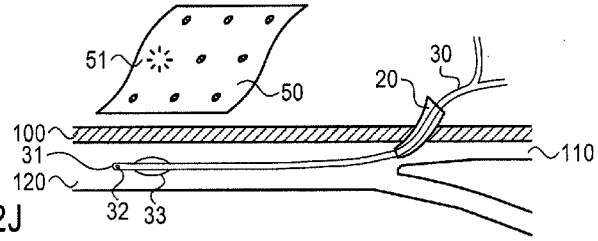
Figure 2K:
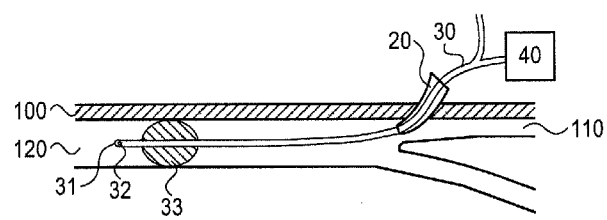

After placement of the expandable sheath within the vessel lumen, insertion of the occlusion catheter 30 commences, as shown in FIGS. 2G-2K. More particularly, FIG. 2G shows sheath 20 inside lumen of vessel 110, which is continuous with more proximal vessel 120 (110 being for example a femoral artery and 120 for example an aorta). Also shown are: occlusion catheter 30 having distal tip 31, magnet 32, and occluder 33, and localizer 50 with detectors 51. The magnet 32 is positioned towards or in distal tip 31. The occluder 33 having a lumen through which the occlusion catheter 30 may pass is positioned on the exterior of occlusion catheter 30 towards the distal end. Localizer 50 having detectors 51 is placed over a patient's body at the approximated area where occlusion is to be performed, while occlusion catheter tip 31 is brought in proximity of sheath 20. Occlusion catheter tip 31 is advanced through sheath 20 which expands and allows catheter 30 to enter vessel lumen 110, and advance into more proximal vessel 120 (FIG. 2H). As catheter tip 31 is advanced under localizer 50, each detector 51 within localizer 50 indicates sensing of magnet 32 at catheter tip 31. FIG. 2I shows indication by first detector 51, which is closest to magnet 32, and as catheter is advanced forward in the vessel towards its target (in the case of endovascular aortic occlusion for traumatic hemorrhage, the target is above the diaphragm, and the surface anatomy mark is the xiphoid process), subsequent detectors 51 indicate their proximity to magnet 32 (FIG. 2J). The user relies on these indications to verify the approximate location of the tip, and once satisfied with tip 31 location, the user may deploy occluder 33 (FIG. 2K). Physiologic parameters may be measured through catheter 30 and by sensors located either within the catheter or in monitor 40. Such parameters include but are not limited to pressure (venous or arterial, depending on the vessel that was cannulated), pulse rate, temperature, hemoglobin saturation, and blood pH. Fluids and drugs may be administered through catheter 30.

Following is one embodiment of the invention methods for providing vascular access and/or endovascular aortic occlusion ("EAO") using the above-referenced system. The method includes the following steps: As shown in FIGS. 2A-K the user identifies a patient in need of vascular access and/or vascular occlusion. User chooses puncture site. After preparation of the puncture site user prepares assembly 16. Preparation of assembly 16 may include opening of sterile packaging, flushing cannulation device 10 with saline, removal of safety pin and possibly loading of cannulation device 10. User punctures patient's skin and tissue 100 with needle 11 of assembly 16 (FIG. 2A-B). User advances assembly 16 towards direction of vessel. Immediately upon penetration of vessel lumen 110 (FIG. 2C), vessel cannulation device 10 automatically advances guidewire 12 into lumen 110 to a predetermined distance (FIG. 2D), usually approximately 5 cm. Optionally vessel cannulation device provides an audio or visual indication of wire advancement. Optionally at this point vessel cannulation device 10 automatically releases guidewire 12 which can then be manually advanced further into the lumen 110. Optionally guidewire may be marked so as to provide an indication of depth of insertion. The user now holds vessel cannulation device 10 together with needle 11 completely still while manually advancing expandable sheath 20 over needle 11 and guidewire 12 into lumen 110 (FIG. 2E). User then holds expandable sheath 20 in place while retracting and removing vessel cannulation device 10, needle 11, and guidewire 12 together (FIG. 2F). Expandable sheath 20 can now be secured to patient's tissues 100 as known in the art. This concludes the establishment of vascular access according to the current invention. Following are the steps of the method for providing vascular occlusion: User places localizer device 50 over intended area of vessel occlusion. User inserts catheter 30 through sheath 20 into lumen 110 and typically advances it into larger vessel 120 (FIG. 2G-H). User continues to advance catheter 30 within vessel 120. As magnet 32 at catheter tip 31 passes under detectors 51 of localizer 50, an indication is given by detectors 51 most proximate to magnet 32 (FIG. 2I). As user continues to advance catheter 30 the indications by detectors 51 will provide the user with an approximation of catheter tip 31 location (FIG. 2J). When satisfied with location of tip 31, user inflates balloon 33 and typically secures catheter 30 in place (FIG. 2K). User can now optionally connect catheter port 36 to monitoring system 40 for measurement of pressure distal to occlusion balloon 33 or use port 35 for administration of drugs, fluids, or drawing of blood samples. Removal of the system is as known in the art and includes deflation of balloon 33, and retraction of catheter 30

Following is a more detailed description of each of the above-mentioned system components.

II. Vessel Cannulation Device

One of the main problems with cannulation of blood vessels is the inadvertent puncture through the posterior wall of the vessel. The various embodiments of the vessel cannulation device described herein address this problem by "blunting" the needle. Such "blunting" may be performed by insertion of an object such as a guidewire through the needle lumen, which decreases the ability of the needle to contact the vessel wall or penetrate and exit it, or by advancing a sheath covering the needle beyond the needle tip, thereby placing a blunt sheath ending distal to the sharp needle ending, thus protecting the vessel from being punctured, and practically "trapping" the needle inside it.

Figure 3A:
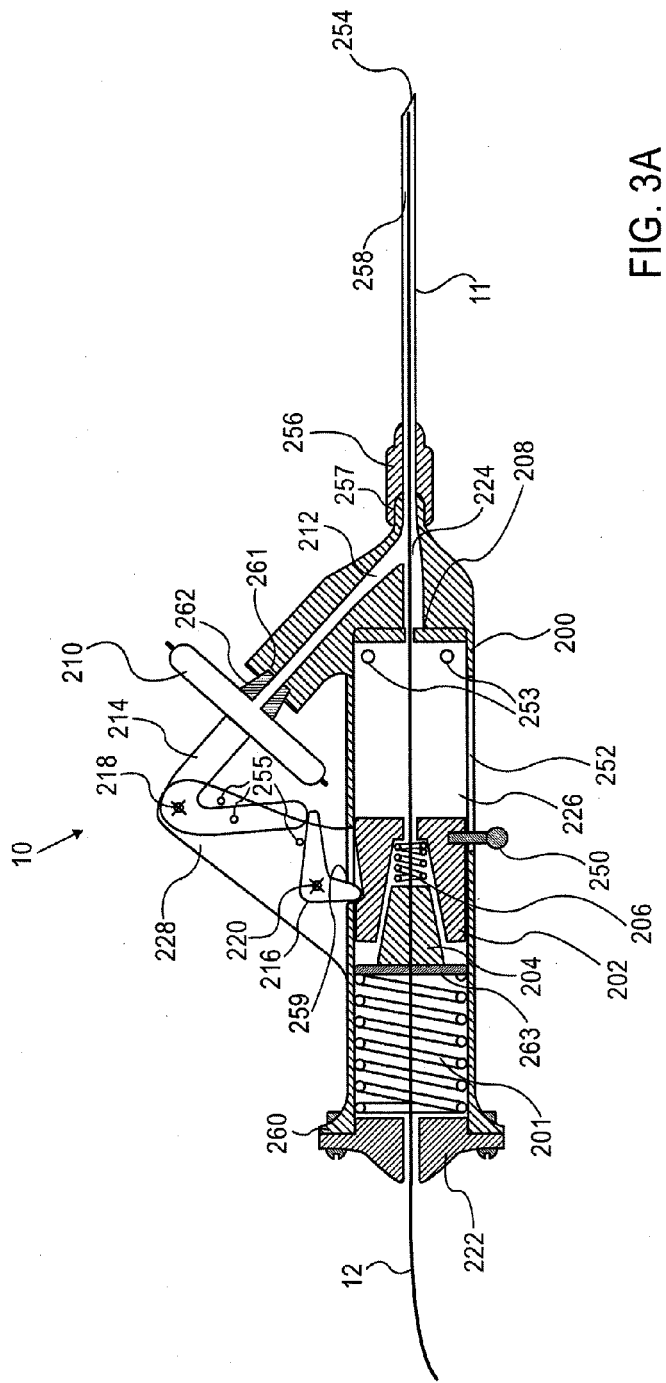
FIG. 3A shows a preferred embodiment of the vessel cannulation device in its loaded state in accordance with the principles of the invention.
Figure 3B:
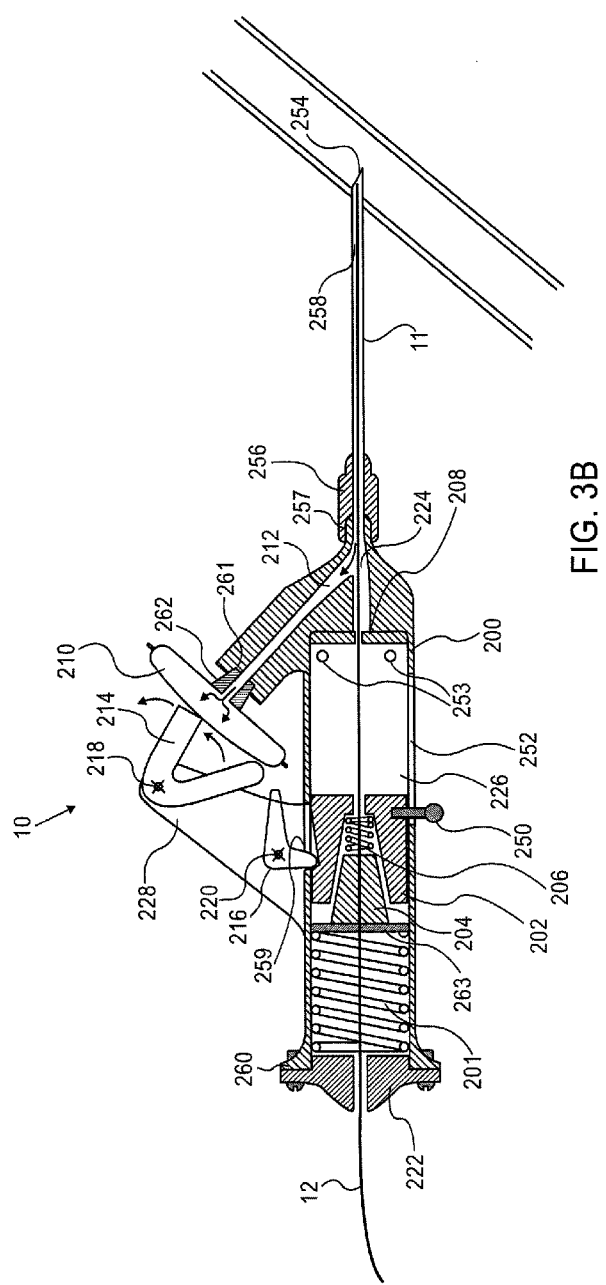
FIG. 3B shows a preferred embodiment of the vessel cannulation device in its at the moment of vessel puncture in accordance with the principles of the invention.
Figure 3C:
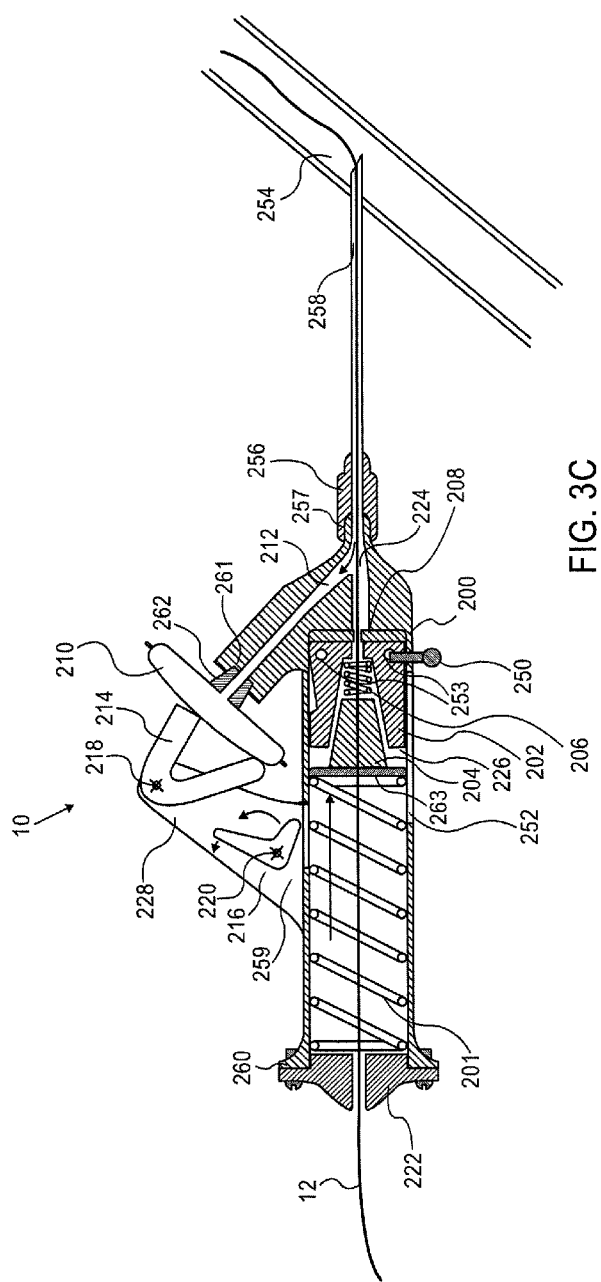
FIG. 3C shows a preferred embodiment of the vessel cannulation device at the moment of vessel puncture in accordance with the principles of the invention.

A preferred embodiment of the vessel cannulation device is a spring-loaded device, which automatically inserts a guidewire into the vessel upon penetration of the vessel by a needle. An embodiment 10 of such a device is shown in FIG. 3A-C. More particularly, FIG. 3A is a longitudinal section of an embodiment of vessel cannulation device 10 in its loaded/armed state, including a body 200, with needle 11 having needle tip 254, needle lumen 258 and needle hub 256 is attached to its front end at needle adapter 257. Body 200 includes needle adapter 257, anterior lumen 224, channel 212 ending in body to diaphragm interface 261, posterior lumen 226, air release holes 253, window 252, aperture 259, and bracket 228. Backplate 222 is connected to proximal end 260 of body 200. Diaphragm 210 connects to body 200 at body to diaphragm interface 261 through diaphragm adaptor 262. Diaphragm 210 is in fluid communication with adapter 262, body to diaphragm interface 261, channel 212, needle adapter 257, needle hub 256, and needle lumen 258. Lever 214 has two arms and is hinged at axis 218. Lever 216 has two arms and is hinged at axis 220. One arm of lever 214 rests on diaphragm 210 and the other on one arm of lever 216. The second arm of lever 216 protrudes through trigger aperture 259 into posterior lumen 226 and is pressed against slider 202. Holes 255 in bracket 228 are possible locations for insertion of a safety pin. Handle 250 connects to slider 202 and protrudes through window 252. Spring 206 rests against slider 202 on its distal side and against gripper 204 on its proximal side. Plate 263 is pressed between the proximal side of gripper 204 and the distal side of spring 201. Spring 201 is pressed on its proximal side against backplate 222. Gasket 208 divides body 200 into anterior lumen 224 and posterior lumen 226. Guidewire 12 runs the length of vessel cannulation device 10, where its distal tip lies a few millimeters proximal to tip 254 of needle 11, passing through lumen 258 of needle 11, hub 256, anterior lumen 224, gasket 208, posterior lumen 226, slider 202, spring 206, gripper 204, plate 263, spring 201, backplate 222, protruding proximally from backplate 222 as required.

In this embodiment needle 11 is a needle of a standard design well known to those skilled in the art. Needle adapter between said needle and body 200 is of standard design, well known to those skilled in the art, for example a "screw-on" design, or a conical press fit.

The methods and materials for making guidewires are well known to those skilled in the art. The guidewire 12 may have a soft and/or flexible tip, possibly formed as a "J" tip, such that is common in normal guidewire use. The flexible tip may prevent the guidewire 12 from damaging the blood vessel when it is advanced by the cannulation device.

In a certain embodiment, the guidewire 12 may have markings on its proximal end, which protrudes from the backplate 222, so that the user has an indication of the length of the guidewire inserted into the blood vessel.

Clearance between the outer diameter of the guidewire 12 and the inner diameter of needle 11 must be such as to allow a pressure transmission upon insertion of the needle's tip into the blood vessel. Too small a clearance will attenuate the pressure transmission into the device, thus increasing the device's response time. An excessively large clearance will have an adverse effect on the devices response time by increasing the volume of blood required to enter the device before the pressure in the device reaches the required threshold. A preferred clearance, which was tested successfully, is such that is the result of using a standard 0.018 inch outer diameter guidewire with a standard 18 G (0.84 mm) inner diameter needle. Optimization of needle size for each required guidewire outer diameter may be accomplished using methods well known to those skilled in the art of fluid dynamics.

From backplate 222 toward distal tip extends large spring 201, shown in its compressed position. In a preferred embodiment, spring 201 is supported by body 200, allowing it to have a free-length to mean-diameter ratio larger then is usually attainable without support. Spring 201 exerts a compressive force on gripper 204, which presses forward on small spring 206.

Spring 206 having a maximum force considerably smaller than spring 201 has in its compressed state, is fully compressed in the device's loaded state, allowing gripper 204 to push against slider 202. Due to the conical shape of gripper 204 and slider 202, the pressing of gripper 204 against slider 202 presses the two gripper halves together so that it exerts pressure on guidewire 12. (Both gripper and slider are described in more detail below).

In this embodiment diaphragm 210 is in fluid communication with anterior space 224 through channel 212. Importantly, all internal channels, lumens and chambers in fluid communication including needle lumen 258, hub 256, anterior chamber 224, channel 212, diaphragm connector 262 and diaphragm 210 must have a minimal possible volume. This total internal volume is one of the major factors affecting device response time from the moment of vessel penetration to automatic advancement of guidewire 12.

Figure 43A:
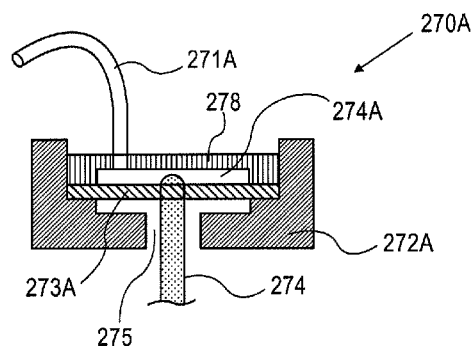
FIGS. 43A-D show various possible embodiments of diaphragm in accordance with the principles of the invention.

FIGS. 43A-D show various possible embodiments of diaphragm 212. More particularly, FIG. 43A is a cross section of diaphragm embodiment 270a including bottom housing 272a, top housing 278, membrane 273a, inlet 271a, vent 275 and plunger 274. Membrane 273a is pressed at its periphery between top housing 278 and bottom housing 272a, producing sealed chamber 274a. Inlet 271a is in fluid communication with chamber 274a. Plunger 274 is connected to diaphragm 273a at its center. Such diaphragms are well known in the art. Fluid entering through inlet 271a increases pressure within chamber 274a thus causing membrane 273a to stretch and protrude outwardly, pushing plunger 274.

Figure 43B:
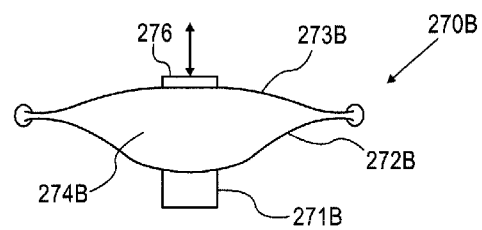

FIG. 43B is a cross section of diaphragm embodiment 270b including bottom housing 272b, diaphragm 273b, having actuating zone 276, inlet 271b. Membrane 273b is connected at its circumference to bottom housing 272b producing sealed chamber 274b. Inlet 271b is in fluid communication with chamber 274b. Actuating zone 276 is the location of highest possible deformation of membrane 273b. Such diaphragms are well known in the art. Fluid entering through inlet 271b increases pressure within chamber 274b thus causing membrane 273b to stretch and protrude outwardly, together with actuating zone 276.

Figure 43C:
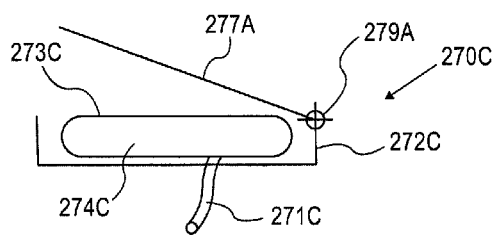

FIG. 43C is a cross section of diaphragm embodiment 270c including bottom housing 272c, balloon 273c having actuating plate 277a hinged at axis 279a to bottom housing 272c, and inlet 271c. Balloon 273c has internal lumen 274c in fluid communication with inlet 271c. Fluid entering through inlet 271c increases pressure within lumen 274c of balloon 273c thus causing balloon 273c to stretch and protrude outwardly, rotating actuating plate 277a around axis 279a.

Figure 41:
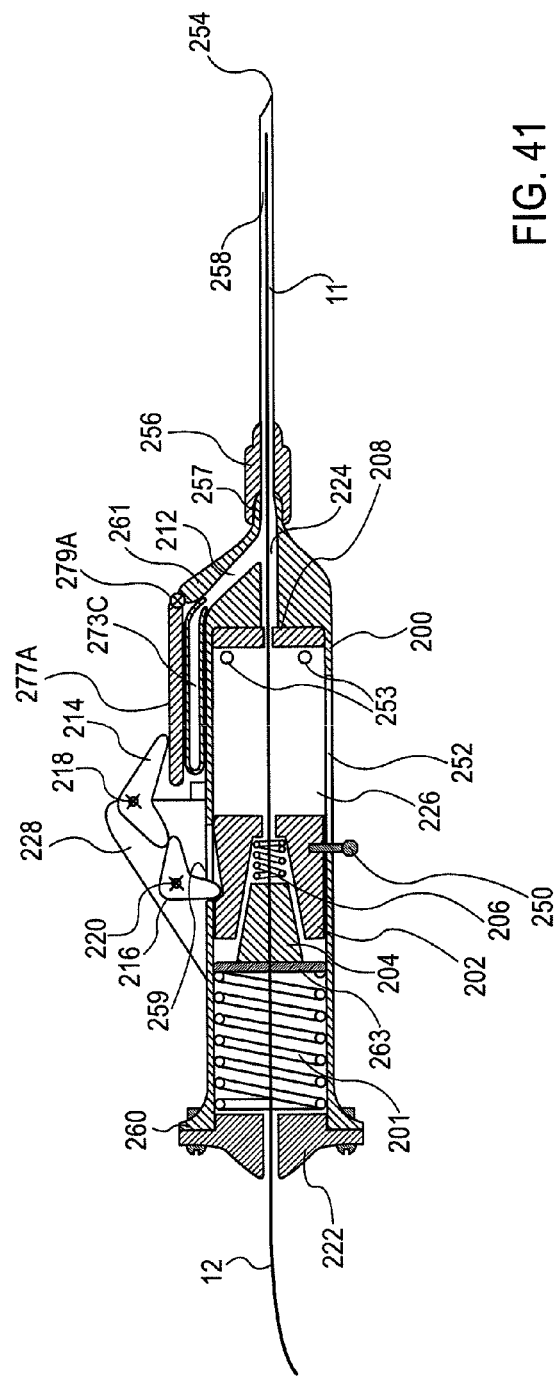
FIG. 41 shows a longitudinal section of an alternative embodiment of a vessel cannulation device in accordance with the principles of the invention.

An embodiment of vessel cannulation device 269 utilizing diaphragm 270c is shown in FIG. 41. All aspects of device 269 except for the diaphragm 270c replacing diaphragm 210, are identical to those of device 10. Use of diaphragm 270c enables device 269 to have dimensions significantly smaller than those of device 10.

Figure 43D:
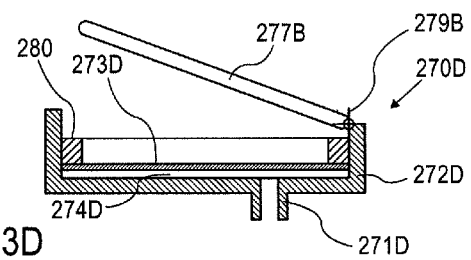

FIG. 43D is a cross section of diaphragm embodiment 270d including bottom housing 272d, diaphragm 273d having actuating plate 277b hinged at axis 279b to bottom housing 272d, and inlet 271d. Diaphragm 273d pressed around its circumference between housing 272d and clip 280, creating sealed chamber 274d. Chamber 274d is in fluid communication with inlet 271d. Fluid entering through inlet 271d increases pressure within chamber 274d thus causing membrane 273d to stretch and protrude outwardly, rotating actuating plate 277b around axis 279b.

Typically, diaphragm 210 embodiments 270a and 270b will have a generally rounded shape, while embodiments 270c and 270d may have other general shapes such as oblong or other shapes, which may aid in minimizing device 10 dimensions.

Returning to FIG. 3A, diaphragm 210 has a minimal volume chamber on the side connected to channel 212. In a preferred embodiment, the diaphragm will have a diameter of about 25 mm, and will exert a total force of about 3.5 Newtons when inserted into a blood vessel having an internal pressure of 40 mm hg. In this embodiment, the diaphragm is pre-calibrated to trip the lever assembly when a pressure of 40 mm hg or more is transmitted to the diaphragm.

Typically, a diaphragm 210 will have a diameter between 5 mm and 100 mm, and will exert a total force of between 0.1 Newtons and 60 Newtons when inserted into a blood vessel having an internal pressure of 40 mm Hg.

Preferably, a diaphragm 210 will have a diameter between 10 mm and 60 mm, and will exert a total force of between 0.5 Newtons and 20 Newtons when inserted into a blood vessel having an internal pressure of 40 mm hg.

In a different embodiment, the diaphragm pressure threshold may be calibrated manually by set-screw or similar device adjusting the length of a compressed resilient member which exerts a force on the diaphragm. Methods of constructing diaphragms are well known to those skilled in the art.

In a different embodiment the diaphragm pressure threshold may be calibrated manually by set screw or similar device adjusting the length of a compressed resilient member which exerts a force on both or one of the levers 216 and 214.

Figure 3D:
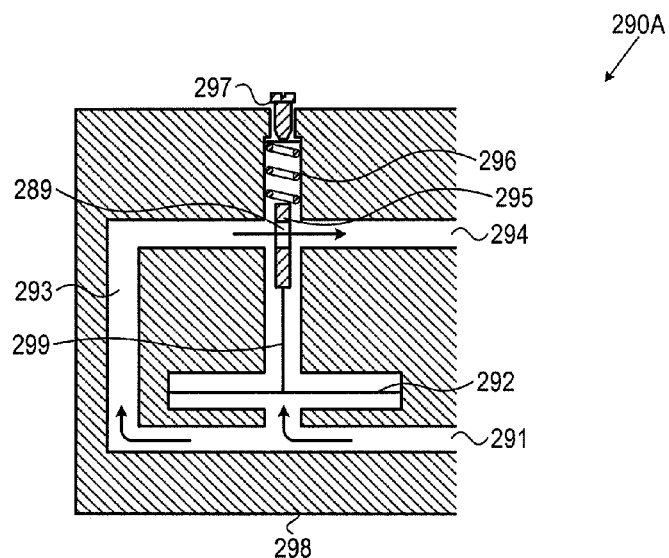
FIGS. 3D-E show a schematic representation of a mechanism for providing an upper threshold limit to the vessel cannulation device in accordance with the principles of the invention.
Figure 3E:
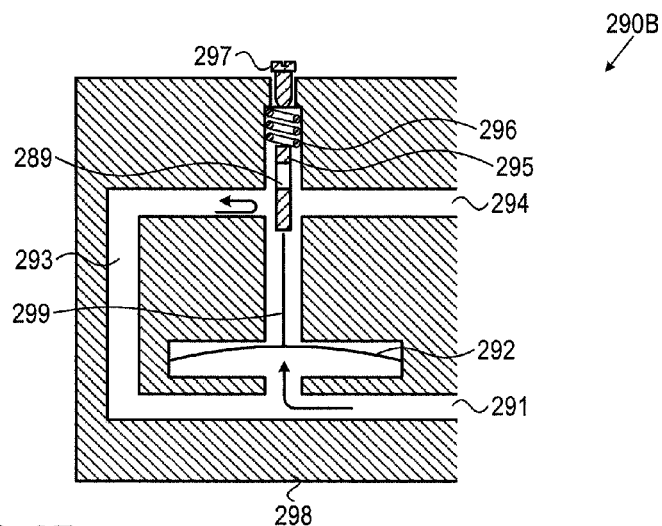
Figure 3F:
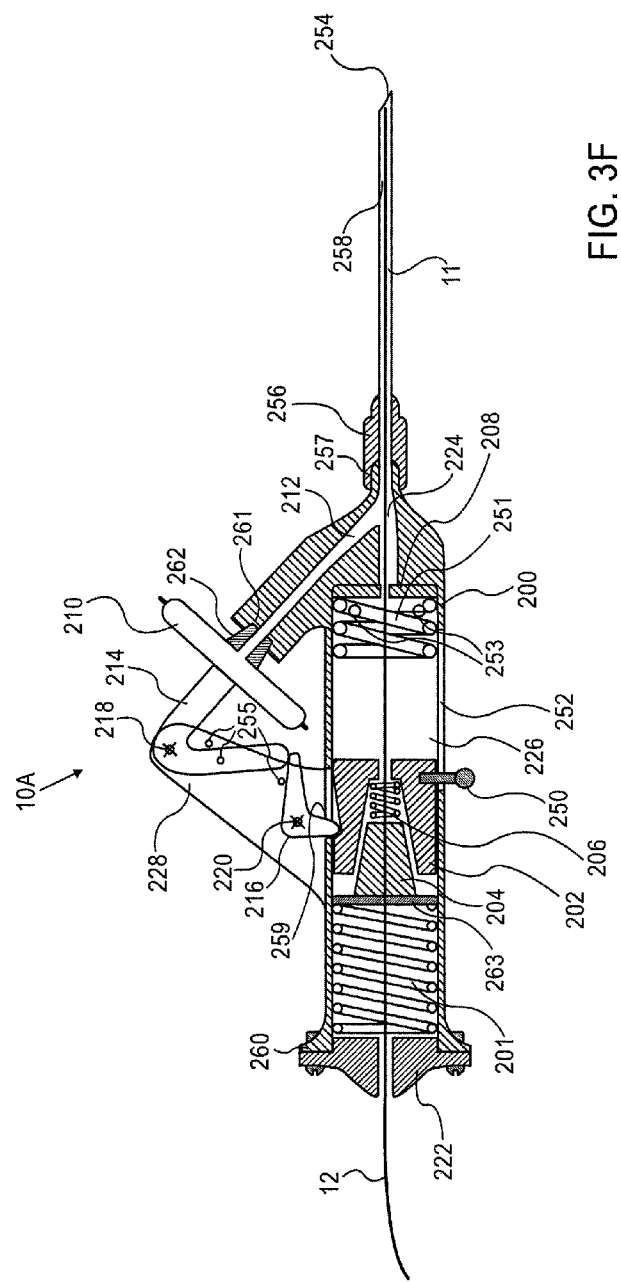
FIG. 3F shows one embodiment of the cannulation device in accordance with principles of the invention.

In a different embodiment, the pressure that will operate the lever mechanism may be set to a range that has both minimum and maximum values. A maximum pressure cutoff value may be set by installing a pilot valve as schematically shown in FIG. 3D-E.

Pressures:

Typically, in the state of shock, arterial blood pressure may fall to an average of about 50 mm Hg, diastolic pressure may even be lower, possibly as low as 30 mmHg, but seldom lower than 20 mm Hg, while the patient is still alive.

In a preferred embodiment, the chamber of diaphragm 210 and channel 212 will be filled with a biocompatible fluid or gel. A biocompatible fluid or gel may reduce diaphragm response time to the needle penetrating into the blood vessel.

In a preferred embodiment, spring 201 will be made of music wire, have a spring constant of 0.3 Newton/mm, a wire diameter of about 0.8 mm, a mean diameter of about 9 mm, have 17 active coils, and a free length of about 90 mm. In its compressed state, the spring will have a deflected length of 30 mm, and will exert a force of approximately 20 Newtons.

Typically, spring 201 uncompressed length may range between 50 mm-200 mm, preferably between 80 mm-150 mm. Typically, spring 201 mean diameter will range between 2 mm-30 mm, preferably between 5 mm-15 mm. Typically, spring 201 wire diameter may range between 0.3 mm-2 mm, preferably between 0.5 mm-1.2 mm. Typically, spring 201 spring constant may range between 0.05 Newton/mm to 2 Newton/mm, preferably between 0.15 Newton/mm to 1 Newton/mm.

Optionally, spring 201 may be made of a plurality of nested springs, the application of which is well known to those skilled in the art.

In a preferred embodiment, spring 206 will be made of music wire, have a spring constant of 0.6 Newton/mm, a wire diameter of about 0.5 mm, a mean diameter of about 5 mm, have 8 active coils, and a free length of about 8 mm. In its compressed state, the spring will have a deflected length of 6 mm, and will exert a force of approximately 1.3 Newtons.

Gasket 208 in the front part of body 200 is a rounded seal with a small hole in its center for passage of guidewire 12. Gasket 208 separates the anterior and posterior parts of body 200. Such a gasket is known as a hemostatic valve, commonly used in vascular devices. The methods and materials for constructing such a gasket are well known to those skilled in the art.

Lever 214 swivels on hinge 218 attached to bracket 228 outwardly extending from body 200. Trigger 216 swivels on hinge 220 also on bracket 228.

In the device's "loaded" state shown in FIG. 3A, guidewire 212 is positioned through centers of backplate 222, spring 201, gripper 204, spring 206, slider 202, gasket 208, with its distal end just a few millimeters from the tip of needle 11. Slider 202 is positioned such that trigger 216 prevents it from moving forward, while large spring 201, gripper 204 and small spring 206 exert forces on it trying to push it forward. Since the force of large spring 201 is much greater than that of small spring 206 at this position, gripper 204 is pressed into conical cavity of slider 202 and its longitudinal slit 230 is compressed, such that its two halves compress guidewire 12 and prevent it from moving relative to vessel cannulation device 10.

Slider 202 presses against one arm of trigger 216, while its other arm is locked against one arm of lever 214, the other arm of which is pressed against diaphragm 210.

Figure 4:
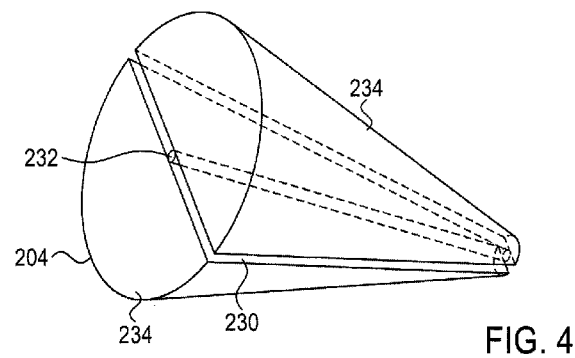
FIG. 4 shows one embodiment of the gripper element of the vessel cannulation device in accordance with the principles of the invention.

FIG. 4 shows gripper 204 in more detail. Gripper 204 may be a cone shaped element with a longitudinal slit 230, dividing it into two halves 234, and a longitudinal groove 232, which has a diameter smaller than that of guidewire 12, creating an interference fit.

Figure 5A:
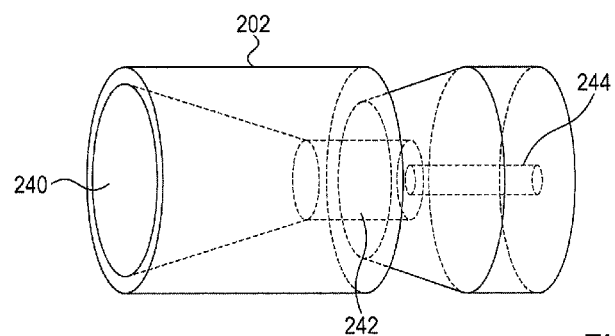
FIGS. 5A-B show one embodiment the slider element of the vessel cannulation device in accordance with the principles of the invention.
Figure 5B:
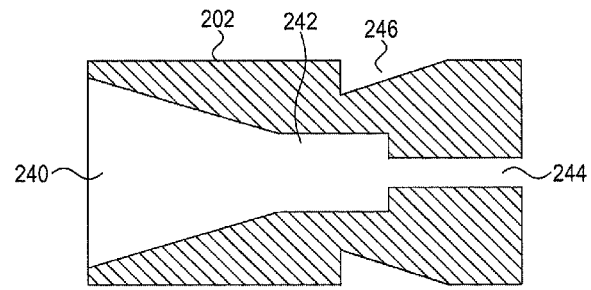

FIGS. 5A and 5B show slider 202 in more detail. FIG. 5A is a three-dimensional drawing of slider 202, which is a cylindrical element with a conical cavity 240, a cylindrical cavity 242, and a tunnel 244 which has a diameter slightly larger than that of guidewire 12. The conical cavity 240 and tunnel 244 are connected to the cylindrical cavity 242. The conical cavity 240 faces towards the proximal end of the cannulation device 10. The cylindrical cavity 242 faces towards the distal end of the cannulation device 10. The guidewire may pass through slider 202 via tunnel 244. Slider 202 may additionally have a circumferential groove 246 around its circumference. FIG. 5B is a longitudinal section of the same part.

In use, when needle 11 of vessel cannulation device 10 penetrates a blood vessel or other lumen containing pressurized fluid, the pressure is transmitted through needle 11 and anterior part of cylinder 224 into channel 212, which leads it to diaphragm 210. As a result of this positive pressure, the diaphragm 210 is rotated. Displacement of diaphragm 210 causes rotation of lever 214 such that it no longer locks trigger 216 in place, in turn allowing slider to shoot forward in body 200. As slider 202 with gripper 204 move forward, guidewire 12 is pushed forward into the vessel. At the end of its travel, large spring 201 applies less force the small spring 206, so that gripper 204 is no longer compressed within conical cavity 240 of slider 202, and its two halves are not compressed towards each other, thus releasing guidewire 12 and allowing it to move freely through all elements of vessel cannulation device 10.

The gasket and diaphragm may be constructed from suitable medical grade materials well within ordinary skill of the art. In particular, the diaphragm is preferably constructed from a material that is expandable in response to pressure generated by blood.

In one embodiment of the cannulation device, a handle 250 is connected to the slider 202. A longitudinal window 252 is added to body 200, to allow the arming of the cannulation device by pulling back on the handle 250 towards the proximal end of the cannulation device, thus compressing spring 201, and placing slider 202 in a position where it may be locked by lever 216.

In a different embodiment, the handle 250 may be of a detachable design, having no parts protruding through window 252 after it is detached.

In another embodiment of the cannulation device 10a as seen in 3F, a spring 251 is added. Also, springs 201 and 206 are sized so that when slider 202 pushes against spring 251 after it has been released by lever 216, the force exerted by spring 201 is greater than that exerted by spring 206, so that the guidewire is not automatically released. The guidewire may then be manually released by pushing on handle 250 towards the distal tip of the device, thus compressing spring 251 and increasing the length of spring 201 to the point where the force it exerts is smaller than the force exerted by spring 206. The gripper will then be pushed towards the device's proximal end, releasing the guidewire.

In a preferred embodiment as seen in FIG. 3A-C, hole or opening 253 or a multiplicity thereof will enable the rushing of air out of body 200, preventing a damping effect caused by compression of air through the travel of slider 202 towards gasket 208.

In a preferred embodiment of the cannulation device, a safety-pin 254 placed in any of the openings 255, will be kept in place until such time as the device must be used. The safety pin will prevent the accidental actuation of the device, which may occur if it is dropped, or otherwise mishandled. The safety pin prevents the operation of the lever mechanism by acting as a mechanical stop.

In one embodiment, the expandable sheath may have a way for attaching it to the distal end of the needle hub. In another embodiment, the expandable sheath may have a way for attaching it to the distal end of the cannulation device.

Figure 40A:
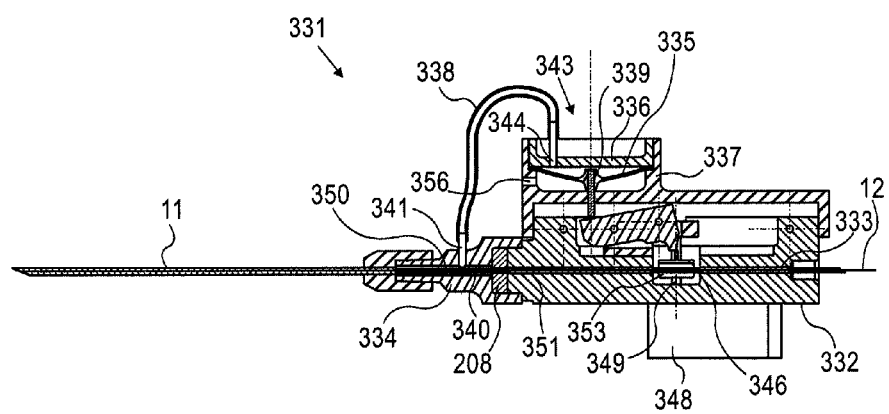
FIGS. 40A-D show various views of embodiments of a wheel driven vessel cannulation device in accordance with the principles of the invention.
Figure 40B:
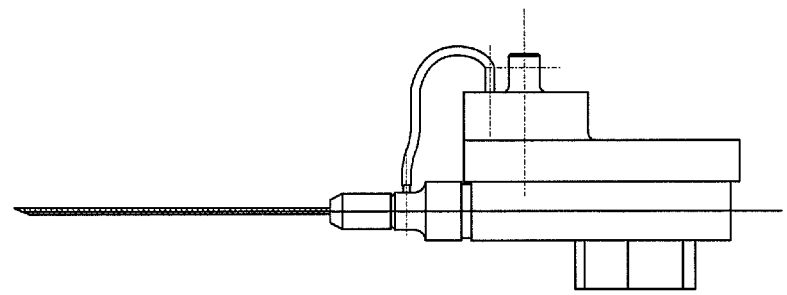
Figure 40C:
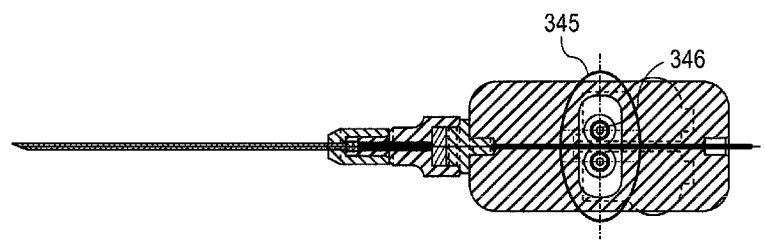

Another embodiment of the cannulation device 331 is shown in FIGS. 40A-C. This embodiment uses rotating wheels as the advancement mechanism. Using wheels is beneficial as it allows the cannulation device to have a length, which is independent of the desired guidewire insertion depth.

This embodiment includes the following: device body 332 having a through opening 333, needle hub adapter 334 having a through opening 340, and one or more radial openings 341, connecting opening 340 with tube 338. The embodiment also includes gasket 208, separating the device 331 into an anterior area 350, and a posterior area 351.

Needle 11 is connected to the distal tip of needle hub adapter 334, and guidewire 12 is inserted into through opening 333.

Device 331 also includes diaphragm assembly 343, which is comprised of top diaphragm housing 336, diaphragm 335, plunger 339, and bottom diaphragm housing 337 having a vent hole 356. Top diaphragm 336 having an opening 344, which is connected by tube 338 to needle hub adapter 334.

Device 331 also includes advancement assembly 345, which includes the following: wheel hub 346, coil spring drive motor 348, drive shaft 349, freewheeling shaft 352, and wheel 353. The wheels axes are at a distance that produces an interference fit between the circumferences of wheels 353 creating a surface that contacts guide wire 12, and produces a sufficient frictional force to drive the guidewire 12. One of the factors determining the frictional force, which drives guidewire 12, is the coefficient of friction between the guidewire 12 and the wheels 353.

In one embodiment of the device 331, the guidewire 12 is pre-treated with a surface coating to produce a high coefficient of friction, thus reducing the required interference fit of the wheels 353, and reducing the required torque supplied by the drive motor. In another embodiment of the device 331, a second drive wheel replaces the free wheel. The extra torque provided by the second drive wheel may allow for a larger interference fit between the wheels 353. In yet another embodiment of the device 331, there are 2 or more sets of drive wheels. Having a plurality of drive motors enables more force to be transferred into the guidewire, or the same force with a smaller interference fit between the wheels 353, and thus less required torque from drive motors 348.

Figure 40D:
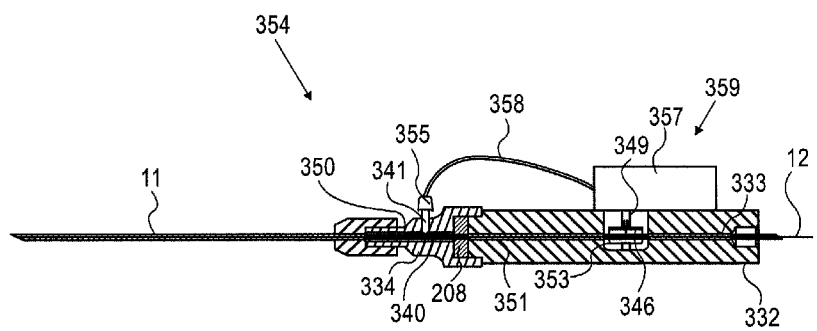

In a different embodiment of the device 354 shown in FIG. 40D, a sensor 355 is located proximal to the needle hub adapter 334. Drive motor assembly 357 includes an electric motor, battery and control circuit as known the art. When the sensor 355 sends a signal to the motor control circuit it turns on the motor 357, which propels the guidewire 12.

Sensor 355 may be any of the following sensors known in the art: pressure sensor, photoelectric sensor, resistance sensor, ultrasonic sensor.

More particularly, FIG. 40D is a longitudinal section of device 354. This embodiment includes the following: Device body 332 having a through opening 333, needle hub adapter 334 having a through opening 340, and one or more radial openings 341, connecting opening 340 with sensor 355. Also gasket 208, separating the device 354 into an anterior area 350, and a posterior area 351.

Needle 11 is connected to the distal tip of needle hub adapter 334, and guidewire 12 is inserted into through opening 333.

Device 354 also includes advancement assembly 359 which includes the following: wheel hub 346, electric drive motor 357, drive shaft 349, freewheeling shaft 352, and wheel 353. The wheels axes are at a distance that produces an interference fit between the circumferences of wheels 353 creating a surface that contacts guide wire 12, and produces a sufficient frictional force to drive the guidewire 12.

Figure 42A:
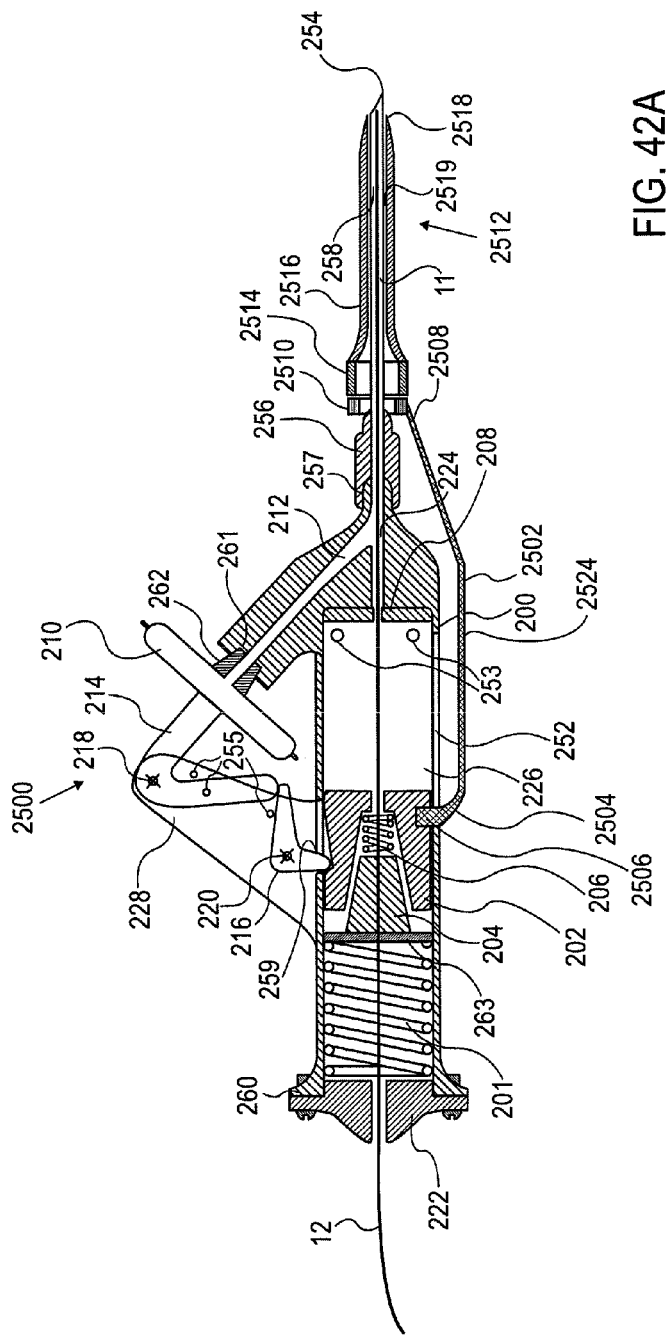

Embodiment 2500 of vessel cannulation device shown in FIGS. 42A-B utilizes a similar mechanism to that previously described for vessel cannulation device 10, in order to automatically advance a sheath over the needle into the blood vessel. Device 2500 automatically advances a sheath over the needle a large distance, inserting the sheath into the vessel.

Typically, in embodiment 2500, sheath 2512 will be automatically advanced between about 20 mm-100 mm, preferably about 30 mm-60 mm.

More particularly, FIG. 42A is a longitudinal section of an embodiment of vessel cannulation device 2500 in its loaded/armed state, including a body 200, with needle 11 having needle tip 254, needle lumen 258 and needle hub 256 is attached to its front end at needle adapter 257. Body 200 includes needle adapter 257, anterior lumen 224, channel 212 ending in body to diaphragm interface 261, posterior lumen 226, air release holes 253, window 252, aperture 259, and bracket 228. Backplate 222 is connected to proximal end 260 of body 200. Diaphragm 210 connects to body 200 at body to diaphragm interface 261 through diaphragm adaptor 262. Diaphragm 210 is in fluid communication with adapter 262, body to diaphragm interface 261, channel 212, needle adapter 257, needle hub 256 and needle lumen 258. Lever 214 has two arms and is hinged at axis 218. Lever 216 has two arms and is hinged at axis 220. One arm of lever 214 rests on diaphragm 210 and the other on one arm of lever 216. The second arm of lever 216 protrudes through trigger aperture 259 into posterior lumen 226 and is pressed against slider 202. Holes 255 in bracket 228 are possible locations for insertion of a safety pin. Spring 206 rests against slider 202 on its distal side and against gripper 204 on its proximal side. Plate 263 is pressed between the proximal side of gripper 204 and the distal side of spring 201. Spring 201 is pressed on its proximal side against backplate 222. Gasket 208 divides body 200 into anterior lumen 224 and posterior lumen 226. Guidewire 12 runs the length of vessel cannulation device 10, where its distal tip lies a few millimeters proximal to tip 254 of needle 11, passing through lumen 258 of needle 11, hub 256, anterior lumen 224, gasket 208, posterior lumen 226, slider 202, spring 206, gripper 204, plate 263, spring 201, backplate 222, protruding proximally from backplate 222 as required.

Additionally, vessel cannulation device 2500 includes bridge 2502 including proximal end 2504, tab 2506, distal end 2508, and ring 2510. Tab 2506 is connected to slider 202 and ring 2510 surrounds needle 11 adjacent and distal to hub 256. Device 2500 further includes sheath 2512 including hub 2514, shaft 2516, tip 2518 and lumen 2519. Sheath 2512 is placed over needle 11, such that needle 11 passes through hub 2514 and lumen 2519, hub 2514 being adjacent and distal to ring 2510.

As shown in FIG. 42B, upon puncture of vessel and release of lever 216, slider 202 is pushed forward, moving bridge 2500 forward with it. As it advances relative to needle 11, ring 2510 pushes hub 2514 of sheath 2512 forward over needle 11, such that tip 2518 is pushed into the blood vessel a distance similar to that of the travel of the guidewire.

Figure 42C:
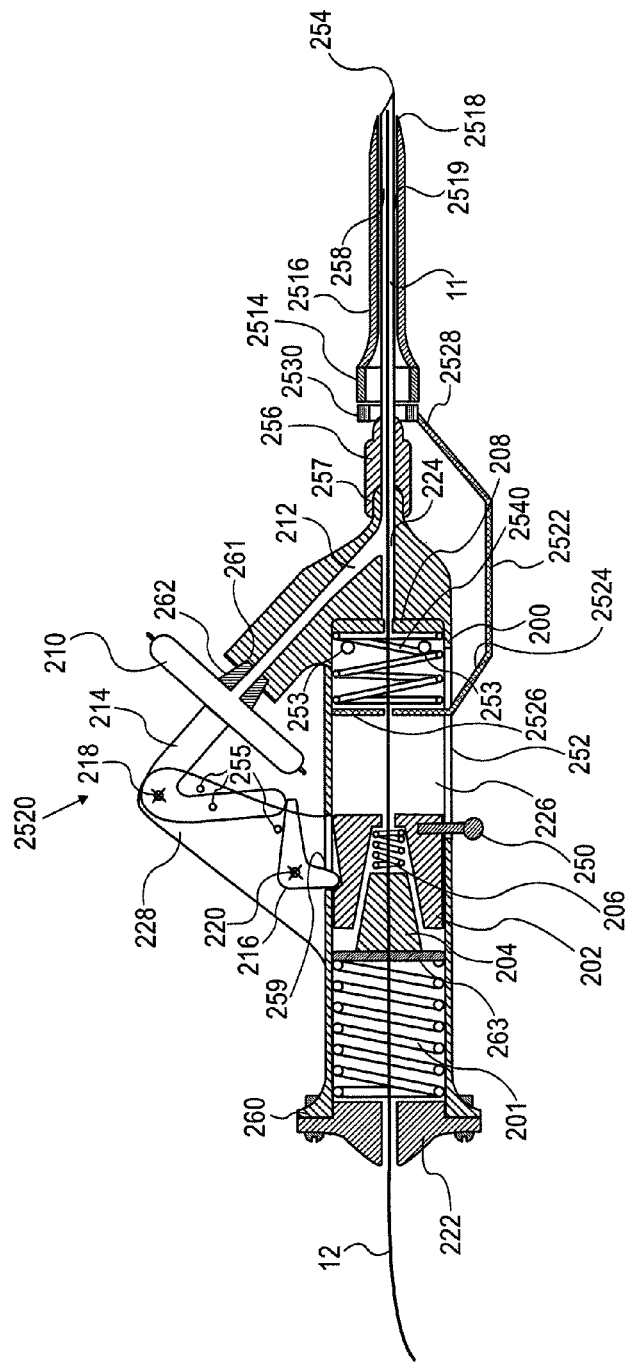
Figure 42D:
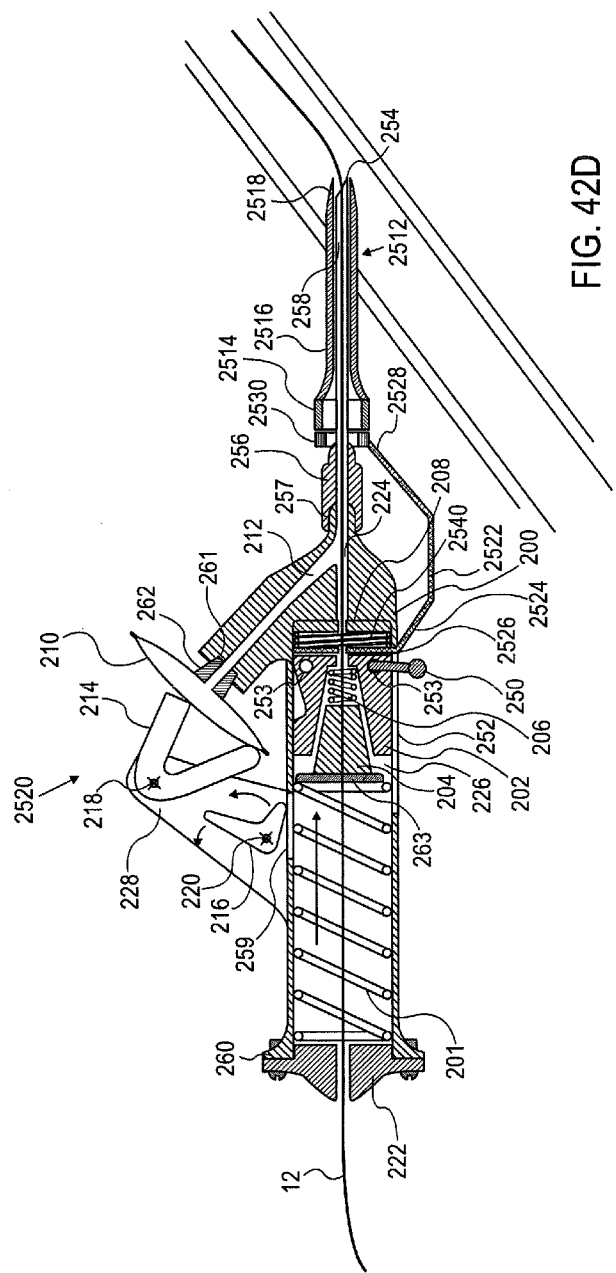

Alternatively, embodiment 2520 of vessel cannulation device shown in FIGS. 42C-D utilizes a similar mechanism to that previously described for vessel cannulation device 2500, in order to automatically advance a sheath over the needle into the blood vessel. Device 2520 automatically advances sheath over the needle a small distance sufficient to cover the needle tip, thus "blunting" it and enabling further manual insertion of device 2520 by the user without danger of puncturing the posterior vessel wall.

FIG. 42C is a longitudinal section of device 2520. Other than bridge 2502, all elements of device 2520 are identical to those of device 2500 above. In addition, vessel cannulation device 2520 includes bridge 2522 including proximal end 2524, tab 2526, distal end 2528, and ring 2530. A spring 2540 is located proximal and adjacent to gasket 208. Tab 2526 is located proximal and adjacent to spring 2540, and ring 2530 surrounds needle 11 adjacent and distal to hub 256. Device 2520 further includes sheath 2512 including hub 2514, shaft 2516, tip 2518 and lumen 2519. Sheath 2512 is placed over needle 11, such that needle 11 passes through hub 2514 and lumen 2519, hub 2514 being adjacent and distal to ring 2510.

As shown in FIG. 42D, upon puncture of vessel and release of lever 216, gripper 204 and slider 202 are pushed forward, advancing guidewire 12 into vessel 11. Slider 202 advances in posterior lumen 226, until it reaches tab 2526. Slider 202 then continues to advance while pushing tab 2526 and bridge 2522. As bridge 2522 advances relative to needle 11, ring 2530 pushes hub 2514 of sheath 2512 forward over needle 11, such that tip 2518 is pushed into the blood vessel a distance sufficient to cover tip 254 of needle 11, and smaller than the distance of advancement of guidewire 12. Typically, in embodiment 2520, sheath 2512 will be automatically advanced between about 1 mm-20 mm, preferably 3 mm-10 mm.

The insertion of sheath 2512 in embodiment 2520 will lag after the insertion of guidewire 12. This occurs because tab 2526 is located a distance from slider 202, which must advance this distance before pushing tab 2526 forward, thus inserting sheath 2512 into vessel. This is beneficial in that better anchoring is achieved before the sheath is advanced, preventing loss of the tract to the lumen in case the sheath insertion faces high resistance from tissues.

The sheath used for embodiments 2500 and 2520 may either be a regular non expandable vascular cannula as known in the art, or an expandable sheath of the invention.

The cannulation device may insert both sheath 2512 and guidewire 12 simultaneously. Alternatively, insertion of sheath 2512 may be the only action performed by the vessel cannulation device, if for example, a guidewire is not used.

Insertion of a guidewire into a body requires that the guidewire be maintained sterile. In order to facilitate the preservation of guidewire sterility in non sterile environments, a cover or housing may be provided. The guidewire protruding from the cannulation device's proximal end, will be housed in said housing thus keeping it sterile. Guidewire may be stored in a rolled state or free state.

III. Expandable Sheath

Figure 6:
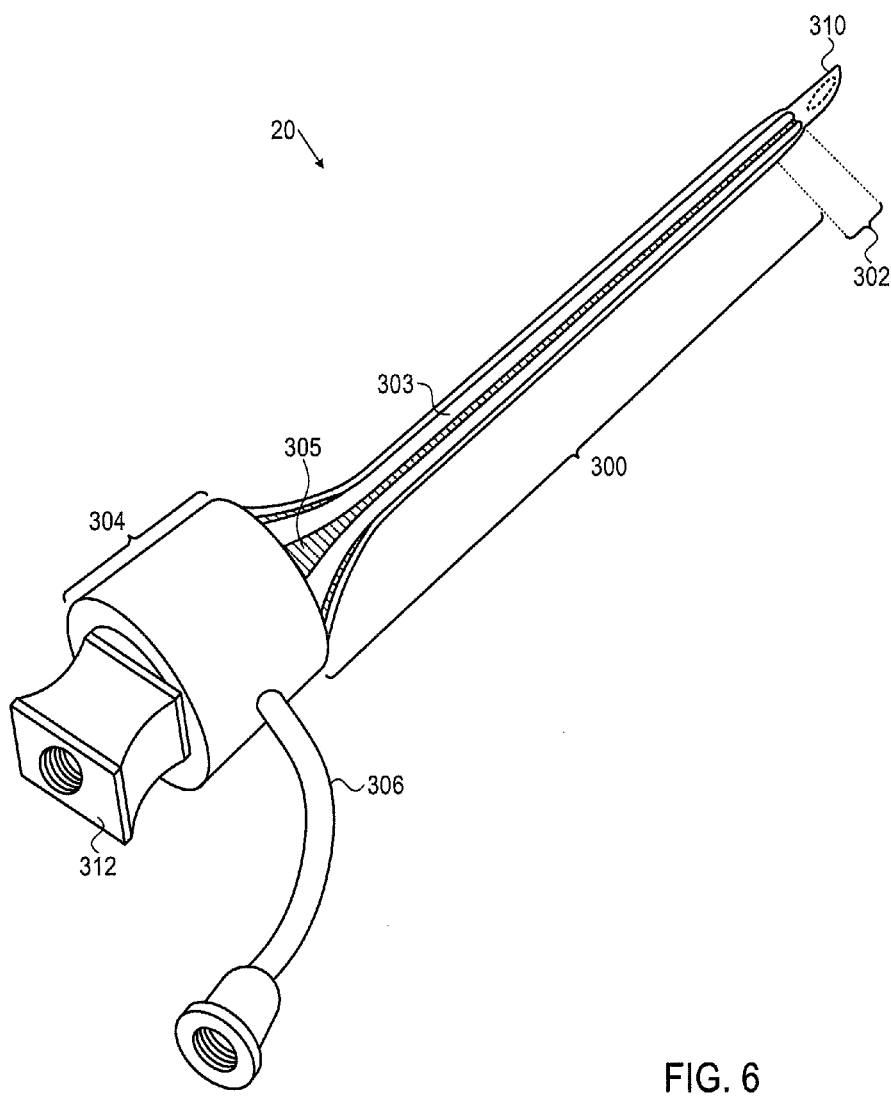
FIG. 6 shows a three-dimensional view of a preferred embodiment of an expandable sheath in accordance with the principles of the invention.
Figure 7:
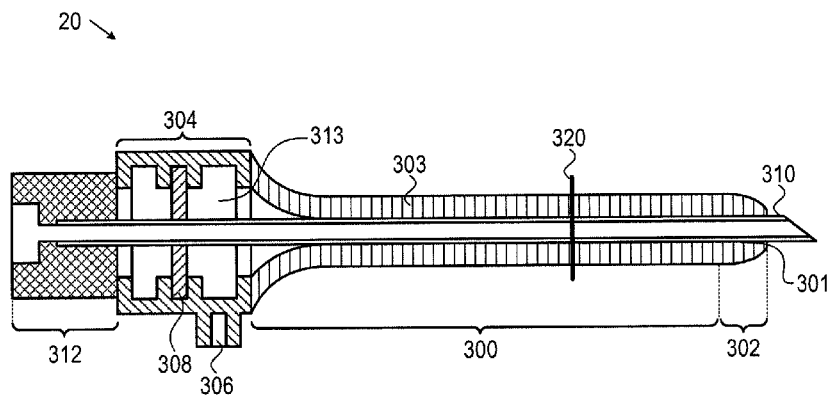
FIG. 7 shows a longitudinal section of a preferred embodiment of an expandable sheath in accordance with the principles of the invention.

A preferred embodiment of the expandable sheath 20 is shown in FIGS. 6-8. More particularly, FIG. 6 is a three-dimensional view of an embodiment of expandable sheath 20 including sheath hub 304 from which longitudinally extends sheath shaft 300 having at its distal end a tip 302. Expandable sheath 20 has a lumen through which a needle and guidewire may pass. Sheath shaft 300 includes longitudinal beams 303 and strips 305. Hub 304 may have fluid outlet 306. Fluid outlet is connected to the lumen of hub 304. Sheath 20 is typically inserted into a vessel over a needle, such that needle hub 312 is proximal to sheath hub 304 and needle tip 310 is distal to sheath tip 302. FIG. 7 is a longitudinal section showing the same elements and in addition is shown hemostatic valve 308. Hemostatic valve 308 is positioned inside hub 304 spanning across the lumen 313 of hub 304. Hemostatic valve 308 may be located proximally to the fluid outlet 306. Hemostatic valve 308 may be removable to facilitate insertion of instruments with a larger diameter.

Also shown in this Fig. is the location 320 of the cross-sections shown in FIGS. 8A-B, 15-21, 25B, and 30A.

Sheath tip 302 has an inner diameter ("ID") having a close tolerance fit to the outer diameter ("OD") of needle 11. The inner diameter ("ID") of sheath shaft 300 also has a close tolerance fit to the outer diameter ("OD") of needle 11 along most of its length. As it nears sheath hub 304, sheath shaft 300, the inner diameter ("ID") may enlarge to sheath hub 304 inner diameter ("ID"). Sheath hub 304 has an inner diameter ("ID") larger than the outer diameter ("OD") of needle 11, for example 50% larger, preferably about 300% larger, possibly 500% larger or more. For example, an 18 G needle, which has an outer diameter ("OD") of approximately 1.3 mm, may be used with an expandable sheath 20 having a sheath hub 304 with an inner diameter ("ID") of 14 fr, which is approximately 4.6 mm, i.e. 250% larger than the needle. Thus, the sheath shaft 300 may circumferentially expand the distance between the outer diameter of the needle 11 and inner diameter of the sheath hub 304, although it may even expand to diameters beyond the hub inner diameter ("ID").

Sheath tip 302 may be tapered so that at its edge, sheath tip 302 outer diameter ("OD") becomes close or essentially equal to the outer diameter of needle tip 310.

Needle 11 may additionally have a cap and "flash" chamber at its hub 312 to allow identification of entry into the vessel without the vessel remaining open to external air. The needle can also be a structure that is capable of piercing the tissue and/or vessel (such as e.g. the artery wall).

Figure 8A:
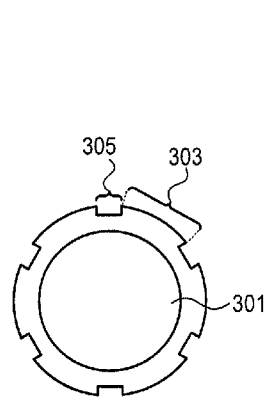
FIGS. 8A-B show cross-sections of a preferred embodiment of an expandable sheath in accordance with the principles of the invention.
Figure 8B:
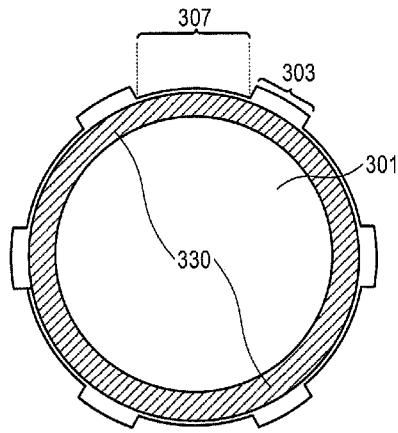

FIGS. 8A-B are cross-sections of shaft 300 of expandable sheath 20 at location 320. In this preferred embodiment, the sheath is made of a single polymeric material such as high-density polyethylene ("HDPE"). As seen in FIG. 8A, the sheath wall includes one or more beams 303 connected by one or more strips 305. Beams 303 and strips 305 extend longitudinally along sheath shaft 300. Beams 303 are areas of greater wall thickness of shaft 300, which confer longitudinal rigidity and column strength to shaft 300, while the strips are areas of thinner wall thickness, where shaft 300 material may easily expand radially. This may occur as plastic deformation in the case of a non-flexible material such as HDPE used in the current embodiment, or as elastic deformation in the case of a flexible material such as silicone. FIG. 8B is a cross-section of shaft 300 at location 320 showing the cross-section of shaft 300 in its expanded state, with beams 303, stretched strips 307, and instrument 330 inside shaft 300.

In use with systems of the invention, sheath 20 is inserted into a vessel together with needle 11 attached to vessel cannulation device 10. Sheath 20 is located over needle 11, such that needle 11 passes through lumen 301 of sheath 20. Sheath 20 is optionally attached to device 10 or to needle hub 312. This may be done using a snap connector, conical press fit, or a screw-on attachment, or other methods of attachment as known in the art. Preferably, such attachment would be sufficient for preventing sheath 20 from advancing unintentionally over needle 11, but not requiring significant force for disconnecting, Following vessel puncture noted in this case by insertion of guidewire 12 and by an indicator, or when used without vessel cannulation device 10, by blood flux through the needle or by blood seen in a "flash" chamber at the needle hub. The methods of constructing flash chambers are well known to those skilled in the art. Sheath 20 is slid into the vessel and needle 11 is removed. Beams 303 prevent buckling of sheath 300 during insertion, which could occur due to friction between it and the skin, subcutaneous tissues, and the vessel wall.

An endovascular instrument 330 having an outer diameter between that of needle 11 and the inner diameter ("ID") of sheath hub 304 may subsequently be introduced into sheath 20. As instrument 330 is advanced through sheath 20, it applies radial forces on shaft 300, and strips 305 expand until shaft 300 inner diameter ("ID") accommodates the instrument (see FIG. 8B) and allows it to enter the vessel.

The expendable sheath or portions thereof can be formed using one or more materials. Typically, the materials used in forming the sheath include medical grade synthetic materials or plastics. Exemplary materials may include, but are not limited to, flexible PVC, polyurethane, silicone, liner low-density polyethylene ("LLDPE"), polyethylene, high density polyethylene, ("DHPE"), polyethylene-lined ethylvinyl acetate ("PE-EVA"), polypropylene, latex, thermoplastic rubber, polytetrafluorethylene (PTFE), expandable polytetrafluorethylene (ePTFE), fluroethylene-propylene (FEP), perfluoralkoxy (PFA), ethylene-tetrafluoroethylene-copolymer (ETFE), ethylene-chlorotrifluoroethylene (ECTFE), polychloro-trifluoroethylene (PCTFE), polyimide (PI), polyetherimide (PEI), polyetherketone (PEEK), polyamide-imide (PAI), other fluoropolymers, and the like.

IV. Occlusion Catheter

Figure 9A:
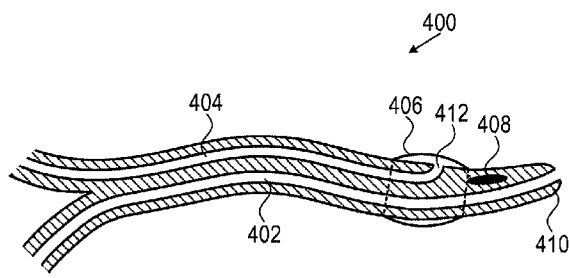
FIGS. 9A-B show one embodiment of a longitudinal section of a trackable aortic occlusion catheter in accordance with the principles of the invention.

The occlusion catheter of the preferred embodiment of the system described above is an aortic balloon catheter with a double lumen and a magnet at its tip. An example of such catheter is shown schematically in FIG. 9. More particularly, FIG. 9A shows occlusion catheter 400, having working lumen 402, balloon inflation lumen 404 and balloon 406. Lumen 402 extends throughout catheter 400 ending at occlusion catheter distal tip 410. Balloon 406 is positioned towards the distal end of the occlusion catheter proximal to the distal tip 410. Working lumen 402 may be used for measurement of pressure within vessel, administration of medications and fluids, and blood sampling proximal to the balloon. Catheter 400 also has balloon 406 in proximity of occlusion catheter distal tip 410, a balloon inflation lumen 404 extending throughout catheter 400 and ending at balloon inflation lumen opening 412, which is within balloon 406, and a magnet 408.

Figure 9B:
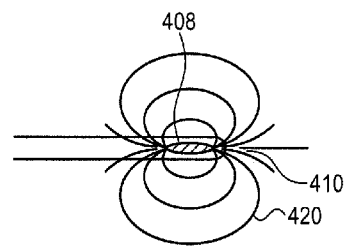

FIG. 9B shows the typical direction of the magnetic field lines 420, in the magnetic field caused by magnet 408 at tip 410 of occlusion catheter 400. In one embodiment, the magnet used is a small volume rare earth magnet, preferably of neodymium. The magnetic field produced by such a magnet having a preferred volume between 0.5 mm$^3$ and 30 mm$^3$ is sufficient for detection by the localizer device of the invention. The magnetic surface field strength emanating from such a magnet would be typically 5,000-50,000 gauss, preferably 10,000-20,000 gauss.

In use, the user first inspects the patient's surface anatomy and decides where she wants to deploy balloon 406, relative to anatomical landmarks, for example just below the xiphoid process. The user then places localizer 50 (described in detail later) over that area of the patient's body. Occlusion catheter 400 is inserted into a vessel through sheath 20 or other vascular access device as known in the art, placed for example at a femoral artery. Working lumen 402 may immediately be used for measurement of central arterial pressure, blood sampling, administration of fluids, blood, or medications. If occlusion for patient stabilization is required, catheter 400 is advanced to the estimated depth, which can be estimated for each specific patient for example by measuring the straight distance from puncture point to xiphoid process and adding 20%, which is a crude estimate of the actual distance within the body that the catheter would pass through the vascular system. As magnet 408 at tip 410 passes through the detection fields of detectors 51 of localizer 50, detectors indicate proximity of the magnet, and user can infer its approximate location. Specific to aortic occlusion in hemorrhagic shock, it is important to assure that catheter tip 410 was not unintentionally advanced into a contralateral inguinal or femoral artery, or into a renal artery. An indication by detectors 51 at the centerline of the patient's body excludes this possibility. It is also important to assure that balloon 406 is above the patient's diaphragm (between the abdomen and thorax) and not too deep inside the aorta, which might cause unnecessary and detrimental blockage of important arterial branches. An indication by detectors 51 approximately at the xiphoid process confirms proper positioning of balloon 406.

V. Localizer

Figure 10A:
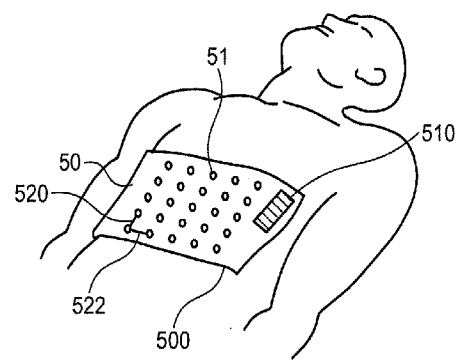
FIG. 10A shows a three-dimensional view of a preferred embodiment of a localizer in accordance with the principles of the invention.

The localizer device of the preferred embodiment of the system described above includes an array of detectors mounted on a soft pad or cloth. The localizer may be disposable, and therefore there are no sterility concerns regarding its use. Typically, localizer 50 will be placed over the patient's upper abdomen and lower chest, centered on the xiphoid process, as seen in FIG. 10A. More particularly, FIG. 10A is a three-dimensional view of localizer 50 on a patient's torso. Localizer 50 includes a pad 500 and one or more detectors 51. Pad 500 may be flexible. Pad 500 adapts itself to the patient's anatomy and thus remains stable on his body. The one or more detectors 51 may be provided in the form of a detector array. The arrangement of the one or more detectors 51 may be defined by rows and columns. An array of 5 rows by 5 columns of detectors 51 is shown. The array size may vary. In one embodiment, the array has a size ranging from 3 to 8 rows by 3 to 8 columns. The distance between rows 520 and the distance between columns 522 may differ. The arrangement of the one or more detectors 51 may differ. A power source 510 may be on pad 500, or separate from it. Power supply 510 is typically a battery of 1.5 V.

Figure 10B:
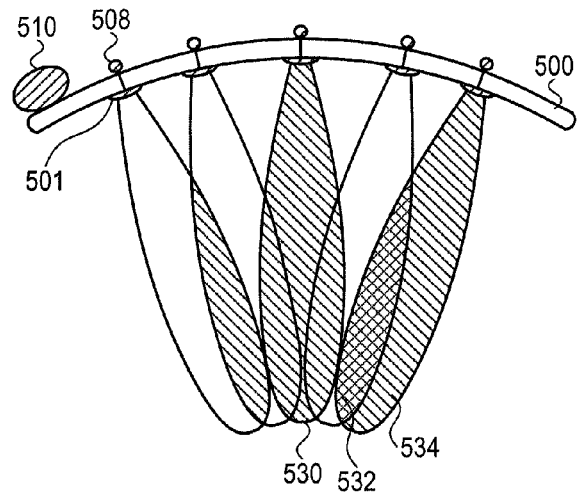
FIG. 10B shows a cross-sectional view of one embodiment of a localizer in accordance with the principles of the invention.

FIG. 10B is a cross-sectional view of localizer 50. Pad 500 is shown in cross-section with a row of detector circuits 501, each connected to a LED 508 extending above pad 500. Power source 510 is located at the side of pad 500. Each detector circuit 501 can detect the magnetic field of a magnet such as magnet 408, when it is within a certain full detector field 530. Detection of magnet presence within detector field 530 is indicated by light from LED 508. It is possible that more than one full detector fields 530 overlap to produce an overlapping detector field 532, while the remainder of full detector field 530 is non-overlapping detector field 534.

Figure 10C:
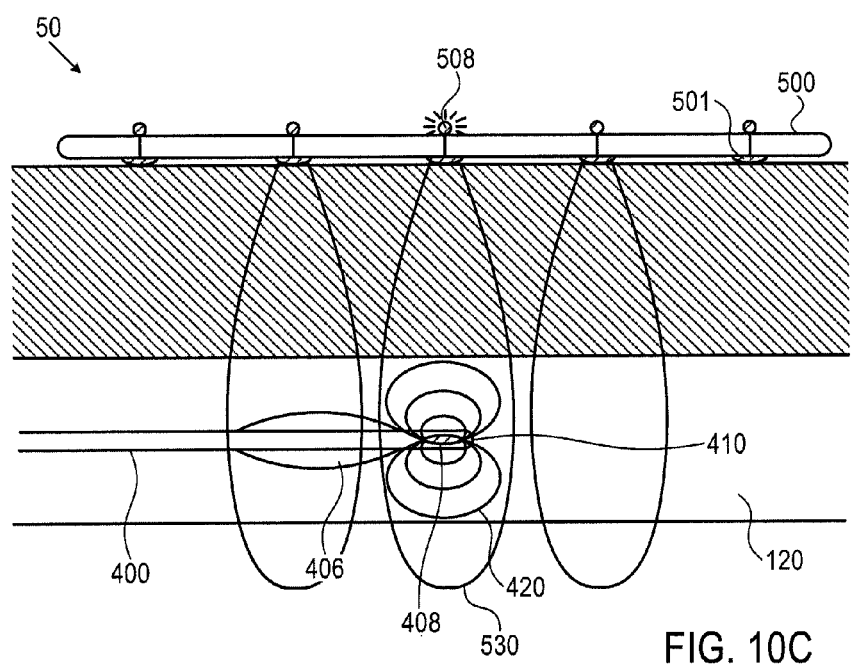
FIG. 10C shows a schematic longitudinal section of one embodiment of localizer in use on a patient in accordance with the principles of the invention.

FIG. 10C is a schematic longitudinal section of localizer 50 in use on a patient. Pad 500 is seen in longitudinal section, with LEDs 508 above and detector circuits 501 beneath it. Each detector circuit 501 is shown with a respective full detector field 530, covering the area of large vessel lumen 120, in this case an aorta. In FIG. 10C, magnet 408 is within full detector field 530 of the middle detector circuit 501, so that its respective LED lights indicating that the magnet is close to it. Pad 500 may typically be made of soft material such as silicon or any other suitable material. Dimensions may typically be 50 cm*50 cm-5 cm*5 cm, preferably 30 cm*30 cm-10 cm*10 cm. Thickness is typically 1 mm-20 mm, preferably 2 mm-10 mm.

Figure 10D:
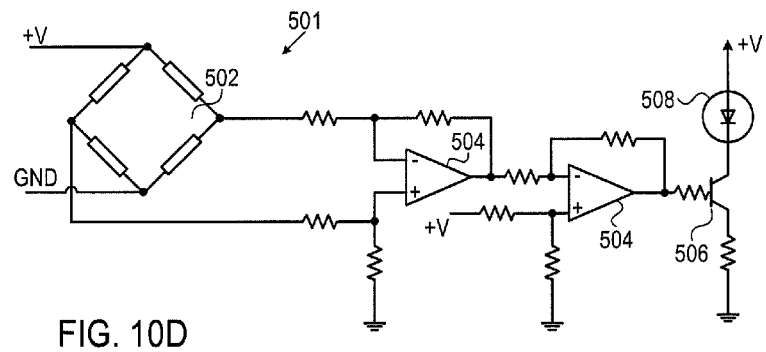
FIG. 10D is an electronic circuit drawing of a possible embodiment of a detector circuit in accordance with the principles of the invention.

FIG. 10D is an electronic circuit drawing of a possible embodiment of detector circuit 501. More particularly, FIG. 10D shows magnetic proximity sensor 502 connected to two operational amplifiers 504, and a transistor 506, operating a LED 508. This configuration provides double amplification of the sensor signal. Magnetic proximity sensor 502 typically provides a low voltage output e.g. 4 mv, which increases when a magnet is in its proximity as a function of the magnetic field strength.

The systems of the invention provide a complete solution for rapid, safe, and controlled aortic occlusion. In addition, each of the above-described system elements may be used independently of the rest of the system, for treatment of hemorrhagic shock as well as for other purposes.

For example, vessel cannulation device 10 may be used to achieve access into an artery for an endovascular procedure, which may be an elective procedure. Alternatively, the same device may be used to access a vein in case of urgent or difficult to find veins. The above may be performed with expandable sheath 20 over needle 11, or without using expandable sheath 20. In such case, vessel cannulation device 10 may be used for introducing the guidewire into the vessel, which may be followed by removal of the device and needle, and subsequent insertion of a regular large bore sheath with a dilator as in the Seldinger technique. The device may also be used to create access to other body cavities such as when performing lumbar puncture or insertion of cerebrospinal fluid (CSF) drains.

Alternatively, for vascular access, the expandable sheath may be used in combination with a standard hypodermic needle or an introducer needle commonly used for insertion of guidewires. Typical needle gauges used are 23 G-14 G, preferably 18 G-21 G, When used in such a manner, the user places the sheath over the needle and punctures the blood vessel with the needle and sheath together, sliding the sheath over the needle into the vessel when blood is seen at the needle hub. The occlusion catheter may be introduced via a regular sheath inserted using the Seldinger technique. It may be deployed under fluoroscopic guidance, or blindly. The localizer may be used for detection of other magnetically marked instruments within the body.

VI. Modifications and Alternate Embodiments

Following are possible modifications and alternative embodiments to the above-described system and its components.

A. Modifications to Vessel Cannulation Device

The following embodiments of vessel cannulation devices simplify the vascular access procedure and shorten the time until administration of treatment. This may be particularly useful in the trauma or shock setting where it may be very difficult to establish access to the vasculature of a hypotensive patient. These devices and methods may also be beneficial in non-urgent settings where they may save time and increase patient comfort by simplifying the procedure.

Figure 11A:
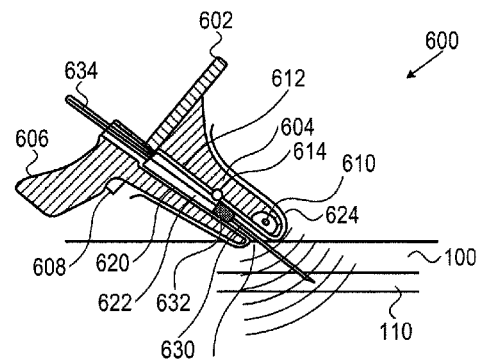
FIGS. 11A-E show various aspects of an embodiment of the vessel cannulation device in accordance with the principles of the invention.

Another embodiment of the invention described in FIGS. 11A-E is a handheld vessel cannulation device, which incorporates both a needle introducer system and an imaging system. More particularly, FIG. 11A shows a longitudinal section of handheld vessel cannulation device 600, consisting of a screen 602 and a handle 606 which extend from a body 604. Body 604 further includes at least one ultrasound transducer 610 and a slot 612. Trigger 608 on handle 606 or body 604 actuates a spring-loaded mechanism, which moves pusher knob 614 forward. A cartridge 620 may be inserted into slot 612. Cartridge 620 has groove 622 along which a needle 630 and its hub 632 may be slid forward when pushed by pusher knob 614. A guidewire 634 is inserted into needle 630. Cartridge 620 together with guidewire 634 and the front of body 604 are covered by sterile drape 624. Sterile drape 624 enables keeping needle 630, guidewire 634, and the device-patient interface sterile, while vessel cannulation device 600 itself does not have to be sterile. Sterile drape 624 also allows knob 614 to push needle 630 along groove 622 in cartridge 620 and allows user to manually push guidewire 634 into needle 630, without making actual physical contact between non-sterile user and device and sterile needle and guidewire. Aperture 626 extends through cartridge 620 and sterile drape 624 enabling passage of needle 320 and hub 322 there-through.

Figure 11B:
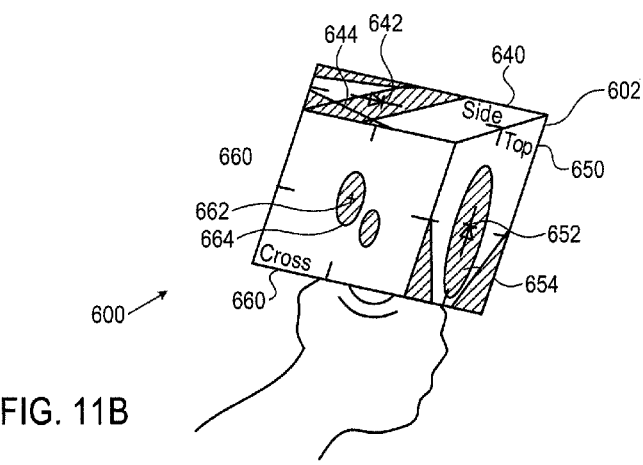

The imaging system of handheld vessel cannulation device 600 consists of one or more ultrasound transducers 610, which are used to obtain simultaneous longitudinal two dimensional views along the expected needle trajectory and/or a cross-sectional view at the anticipated location of the needle tip after its deployment. These images are displayed on screen 602 in real time (FIG. 11B). In this embodiment, the images constantly show where the needle will pass if deployed at that instant, and a specific point in each view is used as a "sight", marking where the tip of the needle will reach. More particularly, FIG. 11B shows screen 602 with side view 640 showing sight 642 centered within vessel side view 644, top view 650 showing sight 652 centered within vessel top view, and cross view 660 showing sight 662 centered within vessel cross view 664. Of note, as each such view shows a point at a fixed distance from the tip of needle 630 within a single plane, each view on its own provides sufficient information for unequivocal spatial localization of the target. However, identifying the vessel using a single view may be challenging, and additional views may make vessel identification easier for the user.

Figure 11C:
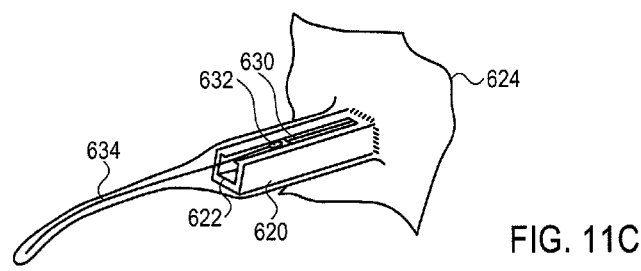
Figure 11D:
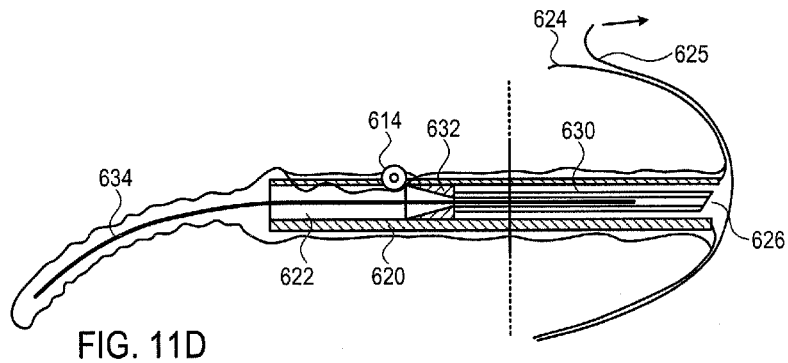
Figure 11E:
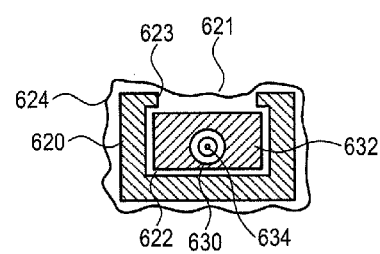

FIGS. 11C-E show detailed views of an embodiment of cartridge 620. More particularly, shown in FIG. 11C is a three-dimensional depiction of cartridge 620 with groove 622, in which is placed needle 630 having hub 632, and guidewire 634, all covered by sterile drape 624.

FIG. 11D shows a longitudinal section of cartridge 620 covered by sterile drape 624, which has on its front a removable adhesive cover 625. Hub 632 of needle 630 is shown within groove 622 where it can slide all the way through aperture 626. Guidewire 634 extends backwards from needle 630 and protrudes out of cartridge 622, still covered by sterile drape 624. Also shown is pusher knob 614, which protrudes into groove 622.

FIG. 11E show a cross-section of cartridge 620 at the line marked in drawing FIG. 11D. FIG. 11E shows cartridge 620, which has a generally U shaped cross-section with groove 622, and protrusions 623, which keep hub 632 of needle 630 inside groove 622. Gap 621 between protrusions 623 enables pusher knob 614 to protrude into groove 622 for pushing hub 632. Sterile drape 624 covers cartridge and has enough slack to protrude through gap 621 with pusher knob 614.

In use, the user disinfects the puncture site and removes adhesive cover 625 from front of cartridge 630, then places vessel cannulation device 600 on puncture site. On screen 602, the user identifies the vessel and points the device such that the sights are centered well within the vessel's lumen at all different views. As the user moves vessel cannulation device 600, views 640, 650, and 660 change their display to show the longitudinal section or cross-section corresponding to the exact angle of the device at each moment. Once she is satisfied with the aim, the user manually stabilizes the device on the patient and pulls trigger 608. When trigger 608 is pulled, pusher knob 614 thrusts needle 630 forward through the patient's tissues 100 in its predefined trajectory. Needle 630 is rigid, so that deviations from the planned trajectory are minimal.

A number of actions can be performed after the needle is inside the lumen including but not limited to:

Insertion of guidewire through needle for subsequent standard placement of sheath over the guidewire.
    Verification of location within arterial lumen by any one of the methods described below.
    Automatic or manual delivery of an over the needle sheath into the artery, by the device.

In other embodiments, only an imaging system is used. Examples of some exemplary embodiments employing the imaging system are described below.

An imaging system may be provided, which utilizes ultrasound to image at least one plane but possibly two perpendicular planes, or three preferably perpendicular planes intersecting at one point. The system may be used to initially locate the target vessel, and may be then anchored such that it constantly displays the vessel and target point in it. The needle is introduced manually, and is viewed on the screen when in the correct trajectory (i.e. when it is within the imaged planes).

Alternatively, the imaging system is static while the user attempts to move the needle within the imaged planes and not controlled by the orientation of the needle.

Figure 12:
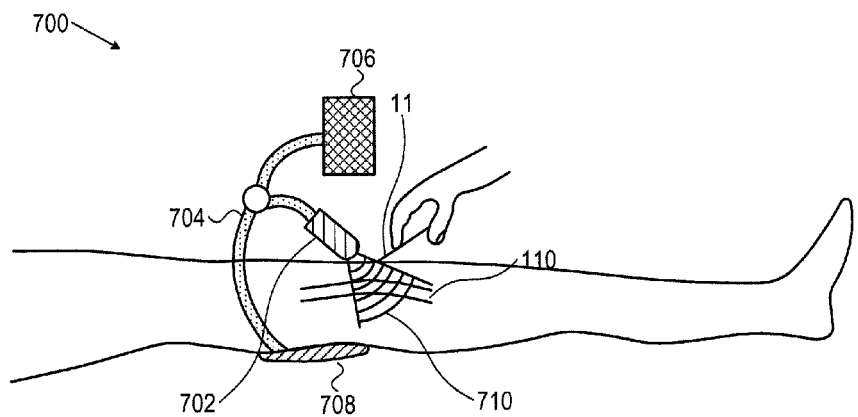
FIG. 12 shows a general view of an alternative embodiment of the vessel cannulation device in accordance with the principles of the invention.

More particularly, FIG. 12 shows a side view of a patient with imaging system 700 consisting of transducer 702 held by arm 704 connected to base 708. Optionally screen 706 also connects to arm 704. Preferably, arm 704 is made of a malleable material or construction allowing quick and easy change of the position of probe 702. Also shown in FIG. 12 is needle 11, which is inserted into vessel lumen 110 while passing through imaged plane 710.

Figure 13:
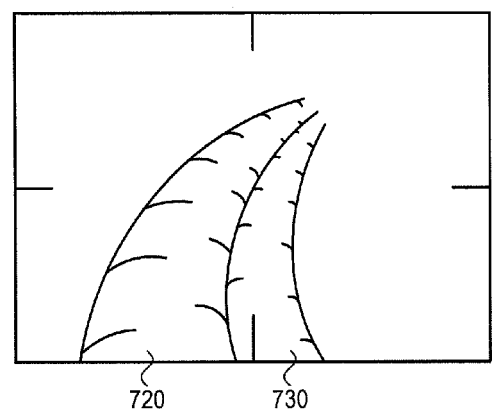
FIG. 13 shows a depiction of the screen view of one embodiment of the vessel cannulation device in accordance with the principles of the invention.

An alternative option is a three-dimensional ultrasound imaging system. This system continuously scans the target area and creates a three-dimensional reconstruction of the vessels. The needle is manually introduced and advanced by the user. The needle is automatically identified by the system, which can display the data in several ways: top, side, and cross-sectional views, or a reconstructed three-dimensional view from a neutral point of view, or three-dimensional image in which the vessel is shown from the needle's point of view, making needle navigation more intuitive (FIG. 13).

Externally, the system is identical to the previously described embodiment in FIG. 12. Transducer 702 may comprise a two dimensional (B-mode) transducer which mechanically swivels to acquire a three-dimensional image, or a dedicated "4D" probe which acquires the three-dimensional image in real time, as known by those familiar in the art. More particularly, FIG. 13 shows the screen image of the current embodiment. The target vessel 720, possibly an artery, is seen adjacent another anatomical structure 730, possibly a vein. Both are shown from the angle of view of the needle.

When used for guiding a needle 11 with an expandable sheath on it into a blood vessel, the current embodiment allows for very easy placement of an endovascular sheath.

Figure 14A:
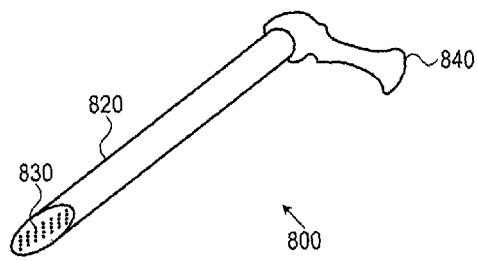
FIGS. 14A-C show another alternative embodiment of the vessel cannulation device in accordance with the principles of the invention.
Figure 14B:
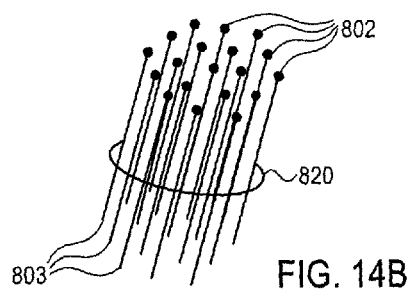
Figure 14C:
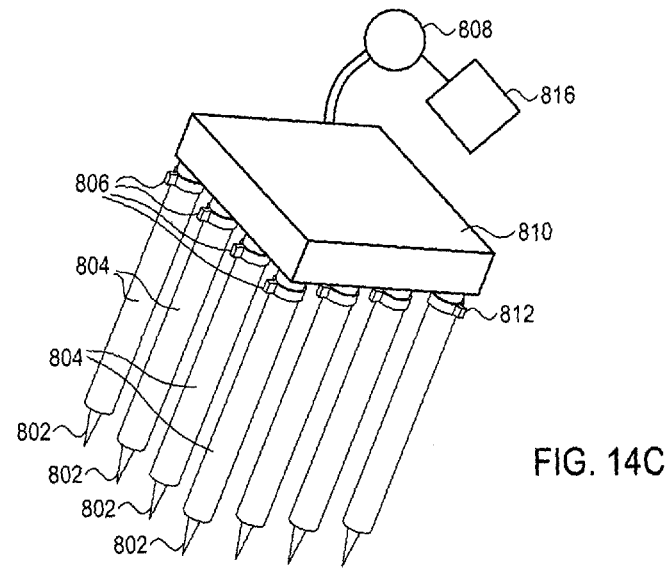

Yet another alternative way for introducing the sheath into a vessel described in FIGS. 14A-C is based on an introducer having an array of needles and a pressure measurement mechanism for identifying which needle has entered the vessel.

More particularly FIG. 14A schematically shows vessel cannulation device 800 having a handle 840, and an array of needles 820, said array ending with a beveled edge 830. This preferred arrangement 830 is used in order to prevent the "Fakir" phenomenon where penetration of all needles together becomes difficult.

FIG. 14B shows an example of said array 820 of needles 802, their distal tips 803 arranged such that they homogeneously cover a defined two-dimensional area (for example 19 needles arranged as a hexagon of 40 mm diameter) or three-dimensional shape (for example a sphere of 40 mm diameter). Needles would preferably be of a small diameter for example 25G, relatively long for example 1.5 inch, and made of as rigid a material as possible to prevent bending.

FIG. 14C shows a schematic representation of various aspects of the embodiment. More particularly, FIG. 14C shows manifold 810 from which extend needles 802 with sheaths 804 covering each of them. Each sheath 804 has a protrusion 806 at its proximal end. Sensor 808 is connected to manifold 810 and to control unit 816. Rotated protrusion 812 points to a different direction than all the rest of the non-rotated protrusions 806. Measurement of the pressure at the tips of the needles is performed by way of pressure sensors located inside each needle at its tip or at its base (for example a fiber optic micro sensor such as that described by Cottler et al., "Performance Characteristics of a New Generation Pressure Microsensor for Physiologic Applications" *Ann Biomedical Eng.* 2009 t; 37(8): 1638-1645) or by sensor 808 which receives pressure from all needles by way of manifold 810 which is electronically controlled such that at any single moment only one of needles 802 is in communication with sensor 808. Rapid alternation of the measurement between the needles enables a virtually continuous pressure measurement from all needles. A control unit receives the pressure measurements and operates a mechanism, which can push any of the sheaths further over the needle, or at least mechanically "mark" the sheath so that it can be manually pushed. Such marking can for example be done by rotation of the sheath such that protrusion 806 will be at a different angle from that of the other sheaths' protrusions (rotated protrusion 812) and as a result will engage with a member that pushes the needle forward.

In use, needle array 820 of vessel cannulation device 800 is aimed by the operator at the estimated location of the vessel entry point and is advanced such that all needles 802 penetrate the skin and underlying tissues. Control unit 816 integrates the inputs from all needles to create a spatial image of the pressures in the tissue. An algorithm may be used to identify a pulsatile pressure and the needle at which the pulsatile pressure is maximal and sufficient for being within an artery. Once such identification is made, the sheath of the appropriate needle is slid into the artery, and the device is removed. Sheaths can be exchanged into larger ones over the wire, or alternatively the original sheath may be an expandable sheath as described in the current invention, so it can be used without necessitating exchange.

Another useful part of this invention is a method for verification of arterial cannulation. As patients may be both extremely hypotensive and hypoxic, arterial blood may be dark and pulsations absent, so that it might be difficult to distinguish whether a sheath is in an artery or in a vein. The method is based on measurement of intraluminal pressure changes in response to small volume fluid withdrawal and injection. This is done by an automated system. A micro sensor placed in the artery continuously measures the pressure in it. An automatically controlled syringe rapidly withdraws a predefined volume of blood (e.g. 3 cc) and after a few seconds rapidly injects it back. As venous pressure is lower and its walls are more collapsible, a vein resists withdrawal more than an artery (i.e. there will be a greater fall in pressure and more force must be used to withdraw) whereas an artery will resist injection more than a vein (i.e. there will be a greater increase in pressure during injection). The relationship between the decreases in pressure during withdrawal to the increase during injection is characteristic of the vessel and a threshold number can be used to distinguish between an artery and a vein.

B. Modifications to Expandable Sheath

Numerous variations of the cross-sectional shape of sheath shaft 300 of expandable sheath 20 may be used, each with its specific advantages and disadvantages. Exemplary suitable variations are shown in FIGS. 15-21, which show cross-sectional views of embodiments of sheath shaft 300 of expandable sheath 20 at line 320.

Figure 15:
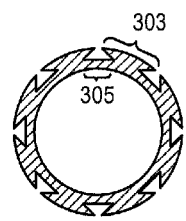
FIG. 15 shows a cross-section of an embodiment of an expandable sheath in accordance with the principles of the invention.

A variation on the cross-sectional shape of the expandable sheath previously described may be used to decrease the friction between the sheath and surrounding tissues during insertion. This variation is shown in FIG. 15. Beams 303 are triangular or trapezoid shaped, forming an almost continuous external surface, which will produce less friction than the shape in FIG. 8A. An additional advantage of this variation is that both strip width and beam base width are increased, thus enhancing expandability while maintaining column strength. In addition, with the beams essentially touching each other, the overall structural strength of the sheath is increased.

Figure 16:
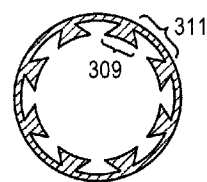
FIG. 16 shows a cross-section of an alternative embodiment of an expandable sheath in accordance with the principles of the invention.

FIG. 16 shows a different variation where the beams protrude inwards. More particularly, FIG. 16 shows beams 309, which are triangular or trapezoid shaped, forming an almost continuous internal surface, while the external surface made of strips 311 and bases of beams 309, is completely smooth and continuous. Such a surface will produce less friction than the shape in FIG. 8A. An additional advantage of this variation is that both strip width and beam base width are increased, thus enhancing expandability while maintaining column strength. Also, with the beams essentially touching each other, the overall structural strength of the sheath is increased. Importantly, wall tension on the strips is greater than in the previous embodiment as they have a larger diameter than strips 305 in FIG. 15 for any same OD and ID, allowing for easier expansion. Disadvantages include greater risk of wall rupture, as well as existence of indentations in the inner lumen wall, which might enhance blood clotting—an undesirable occurrence which might cause complications.

Figure 17A:
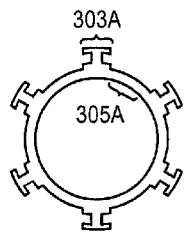
FIGS. 17A-D show cross-sections of alternative embodiments of an expandable sheath in accordance with the principles of the invention.
Figure 17B:
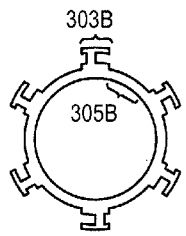
Figure 17C:
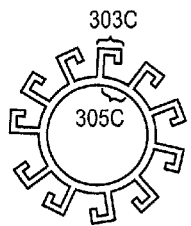
Figure 17D:
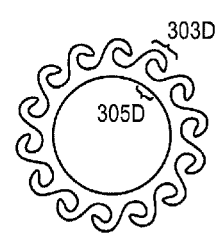
Figure 17E:
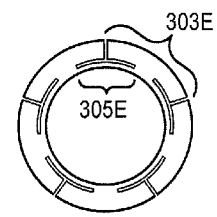
FIG. 17E shows a cross-section of a preferred embodiment of an expandable sheath in accordance with the principles of the invention.

FIGS. 17A-E show various possible cross-sectional shapes for the beams. More particularly, FIG. 17A shows beams 303a having an "I" shaped cross-section which confers very high column strength. Beams 303b shown in FIG. 17B are shown having a generally "U" shaped cross-section, which confers high column strength. Compared to beams 303a, beams 303b are configured to be easier for manufacturing. Beams 303c shown in FIG. 17C have a narrow base, which allows for wider strips 305c, thus creating a large, thin, and expandable surface area. Beams 303c also have a wide outer surface, which may be essentially continuous around the perimeter of the sheath, enabling formation of a smooth sheath. Beams 303d in FIG. 17D have a more wavy cross-section which may be beneficial for manufacturing purposes. Finally, FIG. 17E shows beams 303e, which have an arc shape, and are separated from each other and from strips 305e by thin slits. This embodiment has the advantage of having a completely smooth perimeter while the sheath it at its non-expanded state, as well as high column strength due to the width of beams 303e, and a large expandable area due to the width of strips 305e, while maintaining a thin sheath wall, as beams 303e have a low profile.

Figure 18A:
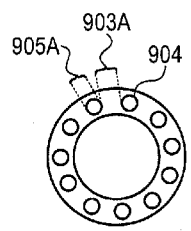
FIGS. 18A-C show cross-sections of alternative embodiments of an expandable sheath in accordance with the principles of the invention.

FIG. 18A is an embodiment where the strips and beams are formed by multiple channels 904 within the sheath wall, such that the areas around each channel form the strips 905a, and the areas between the channels, having a solid sheath wall, form the beams 903a. Of note, channels 904 may have an oval form, thus making wider strips and thinner beams, increasing expandability and vice versa.

Figure 18B:
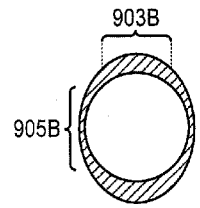
Figure 18C:
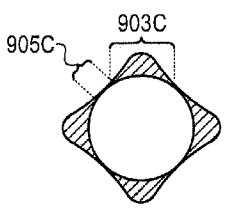

In FIGS. 18B and 18C, the lumen is circular while the external shape of the sheath is non-circular, such that thick and thin areas form the beams and strips.

Figure 19A:
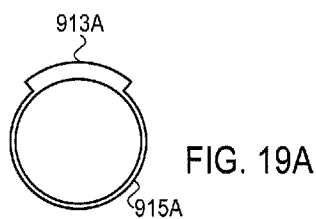
FIGS. 19A-D show cross-sections of alternative embodiments of an expandable sheath in accordance with the principles of the invention.
Figure 19B:
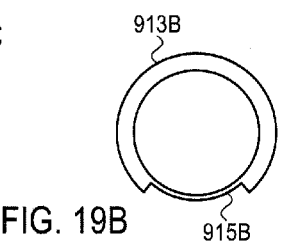
Figure 19C:
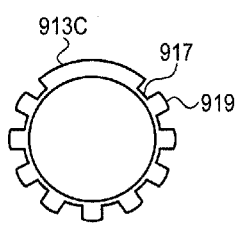
Figure 19D:
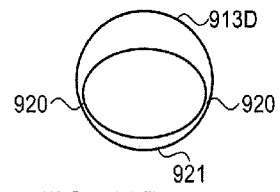

FIGS. 19A-D show asymmetrical cross-sections where a thicker area forms a single reinforcing non-expandable beam, and a thinner area forms the expandable section. More particularly, FIG. 19A shows narrow beam 913a covering a small part of the circumference, while most of the circumference is covered by wide strip 915a. This embodiment will tend to be more easily expanded while having a lower column strength. In contrast, FIG. 19B shows a wide beam 913b and a narrow strip 915b, so this embodiment will be stronger and less easily expanded. FIG. 19C shows an embodiment with single beam 913c and an expandable portion comprised of multiple narrow beams 919 and strips 917. Such a construct conveys both high column strength via relatively wide beam 913c and multiple strips 919, and high expandability via the presence of multiple strips 917. Similarly, multiple zones of differing rigidity and expandability may be formed around the sheath circumference. FIG. 19D shows a different approach to produce a similar result—an elliptical or non-circular lumen within a circular sheath forms thick areas in the wall—thick beam 913d and thin beam 921, and thin areas in the wall—strips 920.

Figure 20:
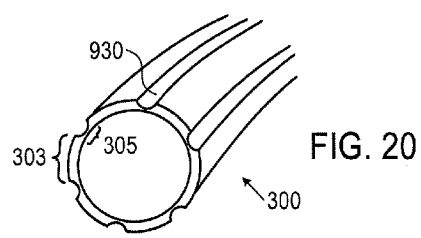
FIG. 20 shows a cross-section of an alternative embodiment of an expandable sheath in accordance with the principles of the invention.

An advantage of the above embodiments and variations of the sheath is that all may easily be manufactured by extrusion or micro-extrusion techniques, commonly used in medical device manufacturing. Alternative methods of manufacturing may include laser processing for forming thin areas around the sheath circumference (FIG. 20), CNC, micro-injection molding and more. More particularly, FIG. 20 is a three-dimensional image of a portion of sheath shaft 300 of expandable sheath 20 with strips 303 and strips 305 formed by making grooves 930 in the external surface of sheath shaft 300, using for example laser processing.

Tapering of the tip can be achieved by many techniques, either during the process of manufacturing the shaft, or as a post process.

Other embodiment of the invention shown in FIGS. 21A-E consist of a sheath shaft 300 made of two or more materials.

Figure 21A:
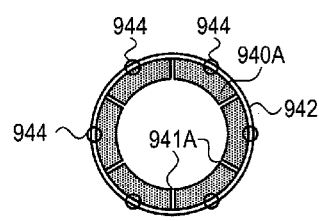
FIGS. 21A-E show cross-sections of alternative embodiments of an expandable sheath in accordance with the principles of the invention.

More particularly, FIG. 21A shows such a sheath formed of longitudinal beams 940a which have an arc shaped cross-section and a straight edge forming a straight separation line 941a between beams 940a and are made of a relatively rigid material, held together by an external layer of compliant material 942. Preferably, beams 940a and compliant material layer 942 are connected to each other at adhesion areas 944, to allow expansion of almost all of compliant material layer 942, since areas connected to beams 940a will become "splinted" and will not participate in expansion. Adhesion areas 944 may consist of points of adhesion between beams 940a and compliant material layer 942, or continuous lines of adhesion extending along the length of beams 940a. Preferably, adhesion areas 944 cover a small portion of the circumference of sheath shaft 300, to enable compliant layer 942 to expand freely without being limited by its connection to beams 940a. Optionally, adhesion points are made only at expandable sheath tip 302 to prevent pleating or folding back of compliant layer 942 due to resistance of tissues during insertion. The advantage of this embodiment is that use of two different materials allows easily achieving expandability by the compliant layer, while beams 940a confer column strength, and manufacturing may be easier. Manufacturing may for example be done by first manufacturing the beams e.g. by molding or longitudinally cutting a tube, then covering it with a thin tube of compliant material and connecting the layers at adhesion areas 944 by welding with laser, adhesion with a glue, thermal treatment or other ways. Alternatively, layer 942 may directly be formed over beams 940a by dipping. The material of compliant material layer 942 may be elastic or non-elastic. In case it is elastic, the sheath returns to its original diameter when tools are removed from it. In case it is non-elastic, compliant layer 942 will remain stretched, but will fold in when tools are removed, and will be easily removable.

Figure 21B:
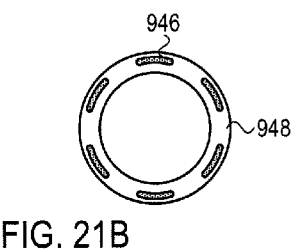

Alternatively, beams may be embedded within the compliant material as shown in FIG. 21B. More particularly, FIG. 21B shows beams 946, which are embedded within compliant material layer 948. An advantage of this embodiment is that adhesion between the layers is not required, as the beams are already within the compliant material. Different materials may be used in different beams within the same sheath to confer multiple structural properties to the sheath. For example, a beam made of a relatively rigid material such as HDPE may be used to add columnar strength and/or longitudinal rigidity to the sheath. A beam made of a malleable material such as stainless steel may be used. This will enable the sheath to assume a bend along its longitudinal axis and maintain the shape until it is intentionally changed.

Both above sheaths may be manufactured using micro co-extrusion techniques as known in the art. In such a case, the use of different materials having the same base compound is preferable, in order to enable good adhesion between the materials. However, as mentioned previously, this is not an absolute requirement, and using materials having different base compounds for intentionally preventing generalized adhesion between the layers may be desirable, to enable controlled localized adhesion only at adhesion areas 944.

Figure 21C:
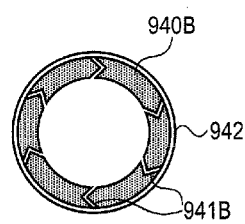
Figure 21D:
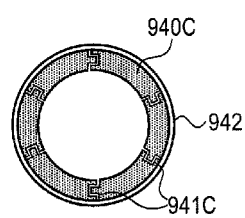

A further improvement to the embodiment shown in FIG. 21A, is shown in FIGS. 21C and 21D. These are examples of various shapes of separation lines 941b-c between beams 940b-c, which increase the structural strength of the non-expanded sheath.

More particularly, FIG. 21C shows beams 940b covered by compliant layer 942. Separation lines 941b are "V" shaped. This shape causes beams 940b to engage with each other while sheath shaft 300 is in its non-expanded state.

FIG. 21D shows beams 940c covered by compliant layer 942. Separation lines 941c are omega shaped such that each beam 940c protrudes into the adjacent beam 940c. This causes beams 940c to engage with each other while sheath shaft 300 is in its non-expanded state, and prevents individual beams from moving radially on their own.

Figure 21E:
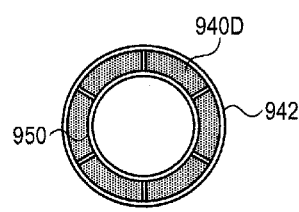

Finally, FIG. 21E shows an embodiment similar to the one in FIG. 21A with the addition of an internal compliant layer. More particularly, FIG. 21E shows beams 940d externally covered by compliant layer 942, and internally by internal compliant layer 950. This embodiment has the advantage of all beams 940b being in contact (as opposed to 21B where compliant material separates them) which reinforces the sheath, while at the same time having an compliant material both internally and externally to hold the beams together without creating adhesions between layers.

A possible manufacturing method for 21A is co-extrusion with the external layer lax (external layer being made of a flexible heat-shrinkable material, then undergoes heat treatment for shrinkage of the external layer to make it taut over the internal layer.

Figure 22A:
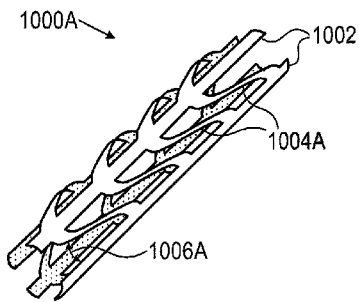
FIGS. 22A-C show three-dimensional views of alternative embodiments of an expandable sheath in accordance with the principles of the invention.
Figure 22B:
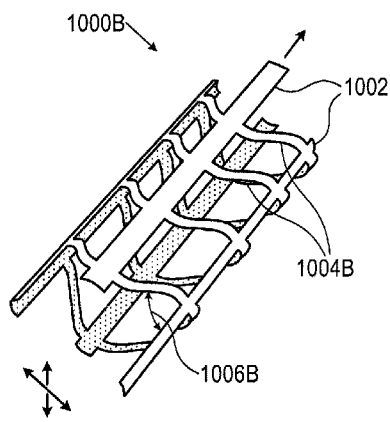
Figure 22C:
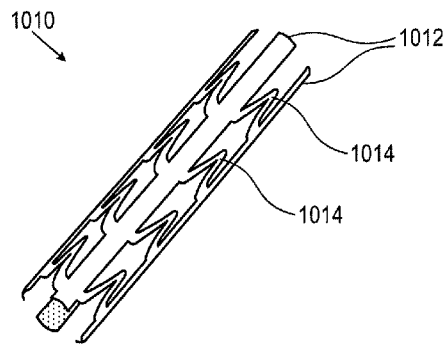

FIGS. 22A-C describe yet another alternative embodiment for sheath shaft 300 of expandable sheath 20, having an internal skeleton made of a relatively rigid material within a compliant material layer. More particularly, FIG. 22A is a three-dimensional image of an internal skeleton 1000a of said sheath shaft 300 in its non-expanded state. Skeleton 1000a is generally tubular shaped and has longitudinal beams 1002 interconnected by diagonal struts 1004a. The external layer is a thin tube made of a compliant material. The layers may be connected to each other in at least some points over the longitudinal beams or the struts. In the non-expanded state of skeleton 1000a, beams 1002 are adjacent to each other and diagonal struts 1004a are almost parallel to them, resulting in a sharp angle 1006a between beams and struts.

FIG. 22B is a three-dimensional image of an internal skeleton 1000b of said sheath shaft 300 in its expanded state. Skeleton 1000b is shown with longitudinal beams 1002 interconnected by expanded diagonal struts 1004b with blunt angle 1006b between them.

Having longitudinal beams throughout the length of sheath shaft 300 prevents a significant change in its length during expansion. However, as sheath shaft 300 is expanded by a tool introduced into it, the distance between beams 1002 increases, as does angle 1006a between diagonal struts 1004a and beams 1002. This causes a slight longitudinal movement of the beams in relation to each other, which may in turn cause a minor lengthening of sheath shaft 300.

FIG. 22C is another embodiment of an internal skeleton 1010 which avoids the above described relative movement. More particularly, FIG. 22C is a three-dimensional image of an internal skeleton 1010 of said sheath shaft 300 in its non-expanded state. Skeleton 1010 is shown with longitudinal beams 1012 interconnected by non-expanded symmetric struts 1014. Symmetric struts 1014 are generally "V" shaped with the point oriented towards the direction of insertion into the body. During expansion, the skeleton diameter increases, but there is no relative longitudinal movement between beams 1012 and therefore not even a minor change in the length of sheath shaft 300.

Internal skeletons 1000 and 1010 may be manufactured by laser cutting thin tubes of relatively rigid material, or by cutting a flat material and welding it into a tube, as is commonly done with stents. The outer layer may be added as a tube over the inner layer and attached to it by gluing or welding. Alternatively, the inner layer may be embedded within the expandable material, for example by dip coating.

Materials used for the inner layer may include metals such as stainless steel or nitinol, or polymers such as PEEK. A feature of this embodiment when a material capable of plastic deformation such as stainless steel is used is that the sheath may be able to maintain its expanded shape, which may be advantageous for some applications.

The embodiments described herein enable the expansion of the sheath to the desired diameter when an instrument is inserted into it through the hub towards the tip. However, in some instances, the friction forces applied by tissues on the tip of the sheath during insertion into the body could cause it to expand at its distal end (tip end), which might cause damage to tissues and/or hinder insertion of the sheath into the blood vessel. It is therefore a further objective of the current invention to prevent this occurrence. In general, designs which confer a preference for expansion from one side of the shaft more than from the other side would assit in obtaining this aspect of the invention. This can be done for example by modifications of the sheath tip, the shaft, or using parts external to the sheath such as the needle or adding a protective membrane. Such modifications may increase the forces required for tip expansion, such that they are greater than the forces required for shaft expansion.

Figure 23:
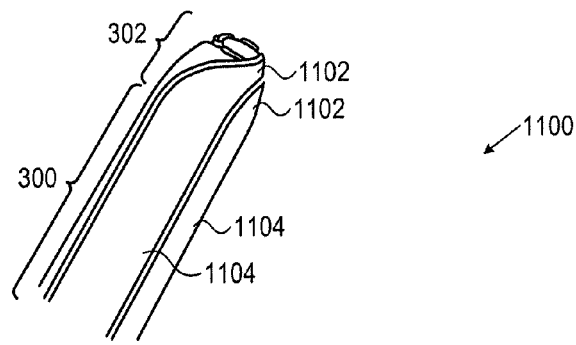
FIG. 23 shows a three-dimensional view of an alternative embodiment of an expandable sheath

FIG. 23 shows a three-dimensional depiction of an embodiment of sheath shaft 300 and tip 302 of expandable sheath 20, which decreases the chances of unintended tip expansion during its insertion into the body. More particularly, FIG. 23 shows a three-dimensional depiction of sheath shaft 300 and sheath tip 302 having straight beams 1104 along shaft 300 and curved part of beams 1102 along tip 302. In this embodiment, the longitudinal beams and strips, which are parallel to the sheath's longitudinal axis along the shaft, curve gradually along the tip such that at its edge they are essentially perpendicular to the longitudinal axis. Thus, forces applied onto the tip edge during insertion into the body, instead of acting to separate between the beams, will actually press them together, preventing tip expansion. This will not interfere with expansion from the hub side, as from that direction, the curvature of the beams gradually diverts from the longitudinal axis.

In one embodiment, this modification may be applied to the sheath using a secondary process with warming and rotating the tip over a mandrel.

Figure 24A:
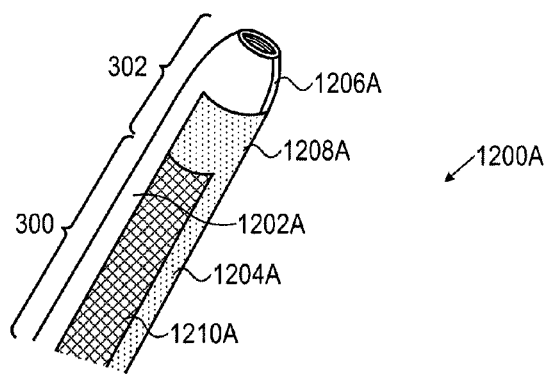
FIGS. 24A-B show three-dimensional views of an alternative embodiment of an expandable sheath in accordance with the principles of the invention.
Figure 24B:
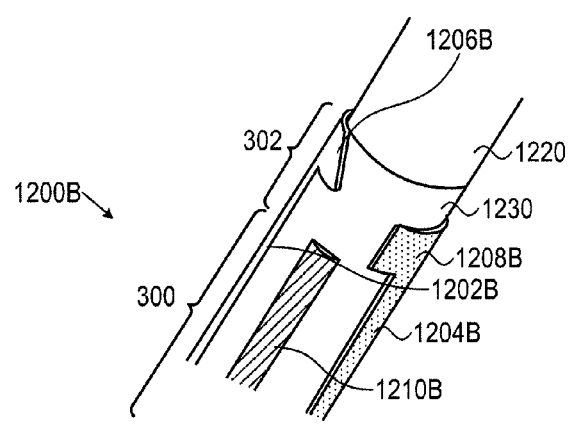

FIGS. 24A-B show another embodiment of a possible modification to the tip. In this embodiment, the tip edge is formed by a circular extension from only one of the beams, which completely encircles the tip and is interrupted by only one strip. Such a tip is more resistant to expansion than the regular tip. When a tool is inserted through the sheath, the circular extension opens and the beams move apart, the strips expanding between them.

More particularly FIG. 24A shows a three-dimensional depiction of an embodiment of sheath shaft 300 and tip 302 in the non-expanded state. FIG. 24 shows beam 1202a with circular extension 1206a, which completely encircles the tip, beam 1204a with partial circular extension 1208a, which partially encircles the tip, and beam 1210a, which ends with no extension at the border between shaft 300 and tip 302 barely touching circular extension 1208a. Together, circular extensions 1208a and 1206a form tip 302, while beams 1202a, 1204a, and 1210a form shaft 300. In this embodiment, strips interconnect the beams as previously described for example in FIG. 17E, but these are not seen in this image as they are concealed by the beams.

FIG. 24B shows a three-dimensional depiction of the above embodiment of sheath shaft 300 and tip 302 in the expanded state due to insertion of tool 1220 through sheath 20. Shown are beam 1202b with circular extension 1206b now only partly encircling the tip area, beam 1204b with partial circular extension 1208b which partially encircles the tip area, and beam 1210b. As the shaft has expanded, the beams and circular extensions are now at a distance from each other and as a result the gaps between them are covered by expanded strips 1230.

Figure 25A:
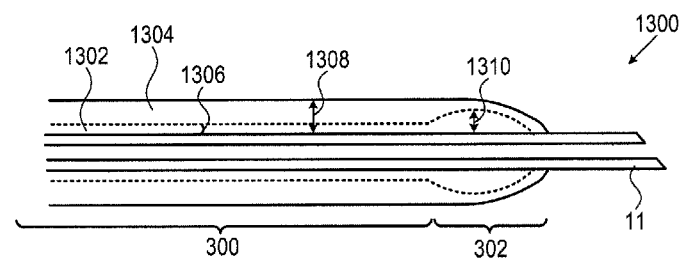
FIG. 25A-B show cross-sectional and longitudinal sections of an alternative embodiment of an expandable sheath in accordance with the principles of the invention.
Figure 25B:
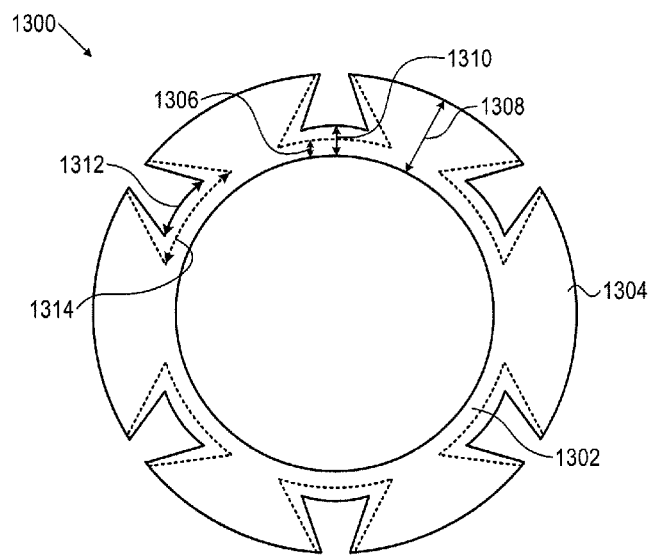

Another possible modification of the tip described in FIGS. 25A-B is a change in the dimensions of the strips and/or beams. For example, the strip areas at the tip may be narrower than at the shaft. The strips at the tip may additionally be thicker than at the shaft. This will require more force for expansion at the tip end and make unintended expansion less likely.

More particularly, FIG. 25A shows a longitudinal section through sheath 1300, showing shaft area 300 and tip area 302, as well as needle 11. Strip 1302 has thickness 1306 at shaft area 300 and 1310 at tip area 302. Beam 1304 has constant thickness 1308 along shaft and tips areas, until it tapers down at tip 302.

FIG. 25B shows a cross-section of sheath 1300 at line 1310. Beams 1304 are shown having constant thickness 1308. Strips 1302 are shown, having strip thickness at shaft area 1306, which is smaller than strip thickness at tip area 1310. Strip width at shaft area 1314 is greater than strip width at tip area 1312.

Figure 26:
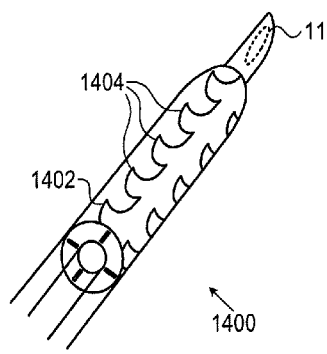
FIG. 26 shows a three-dimensional view of an alternative embodiment of an expandable sheath in accordance with the principles of the invention.

The shaft or the whole length of the sheath may be modified in such a way as to promote proximal to distal expansion vs. distal to proximal expansion. For example, the strips may take a nonlinear form, such that instead of a straight separation line between the beams, they form a jagged separation line as shown in FIG. 26. This jagged line has a further attribute of its "teeth" being pointed towards the tip. Separation of the beams from the direction of the tip towards the hub will meet with more resistance than separation from the hub towards the tip. More particularly FIG. 26 shows sheath 1400 on needle 11, jagged line 1402 with teeth 1404.

Figure 27:
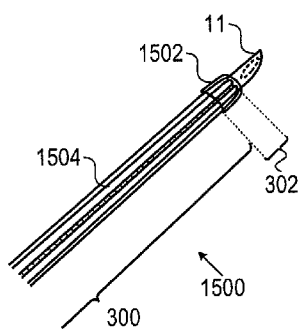
FIG. 27 is a three-dimensional view of an alternative embodiment of an expandable sheath in accordance with the principles of the invention.

FIG. 27 shows an additional approach in which an external reinforcing membrane is attached to the introducer tip. More particularly, FIG. 27 shows sheath 1500 on needle 11, external reinforcing membrane 1502, and shaft 1504. External reinforcing membrane 1502 holds the beams together at the introducer tip and prevents unintended expansion thereof. The membrane may be a tearable membrane or have elastic/plastic deformation properties such that greater force will be required to expand the tip in its presence. Once the sheath dilates upon instrument insertion, the required force will be reached and the membrane will tear or expand while remaining connected to the tip. This embodiment may be relatively easy to manufacture, as the sheath may be manufactured by extrusion, and the membrane may then be placed on the tip and connected by glue, thermal adhesion or other method known in the art.

Figure 28:
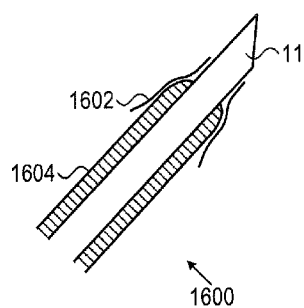
FIG. 28 shows a longitudinal section of an alternative embodiment of an expandable sheath in accordance with the principles of the invention.

Yet a different approach is provided by a thin protective membrane, which is connected to the needle circumferentially, and loosely covers the tip of the sheath. More particularly, FIG. 28 shows sheath 1600 on needle 11, protective membrane 1602, and shaft 1604. During insertion of the needle, the membrane protects the sheath tip from friction with the tissues. Once in the vessel, the needle is removed with the membrane, which folds back easily and follows the needle into the sheath. Such a membrane may be made of a thin film of nylon, PTFE or other polymer.

Figure 29:
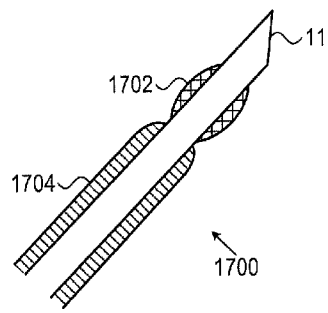
FIG. 29 shows a longitudinal section view of an alternative embodiment of an expandable sheath in accordance with the principles of the invention.

The needle may be adapted so as to provide an alternative solution for preventing introducer tip expansion during insertion as shown in FIG. 29. More particularly, FIG. 29 shows sheath 1700 on needle 11, enlargement on needle 1702 and shaft 1704. Enlargement 1702 has an OD equal to that of the sheath, and a short taper to the sheath's ID. The enlargement serves as a "shield" for the sheath during insertion, and is then pulled out through the sheath, which is possible due to the taper.

Figure 30A:
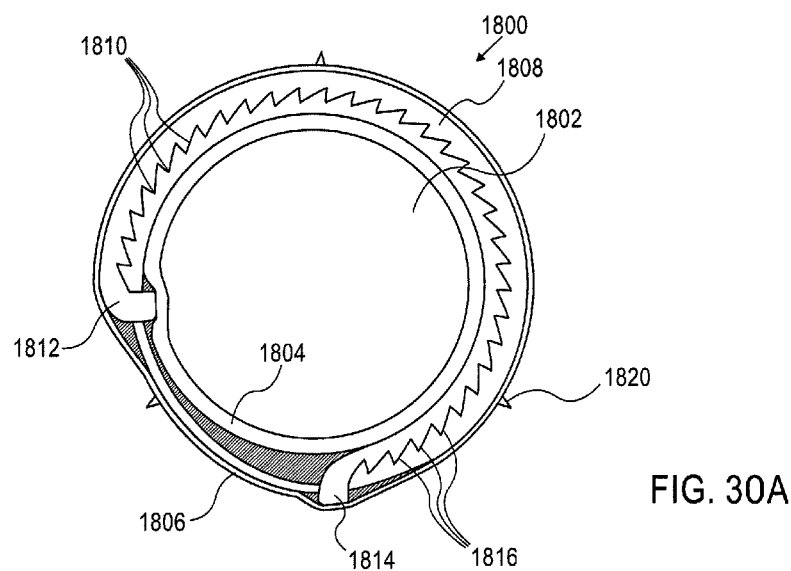
FIGS. 30A-B show a sectional and three-dimensional view of an alternative embodiment of an expandable sheath
Figure 30B:
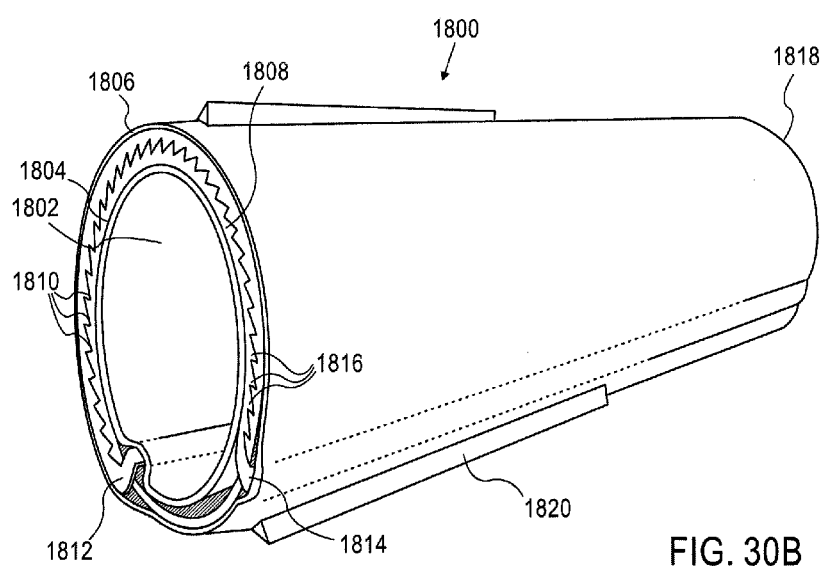

An alternative expandable sheath utilizing a ratchet mechanism is described in FIGS. 30A-B. More particularly, FIG. 30A is a cross-section of ratchet sheath 1800 having lumen 1802. Described from lumen 1802 outward, sheath 1800 includes inner expandable layer 1804, covered by roll 1808, which in turn is covered by external expandable layer 1806. Roll 1808 includes inward facing teeth 1810, inward facing holder 1812, outward facing teeth 1816, and outward facing holder 1814. FIG. 30B is a three-dimensional view of sheath 1800 showing all the aforementioned elements as well as distal tip 1818. Holders 1812 and 1814 extend along the length of sheath 1800. Roll 1808 is rolled upon itself such that holders 1812 and 1814 keep its teeth engaged with each other. In its non-expanded state all or most teeth are engaged, however as sheath is expanded by introduction of a tool through lumen 1802, teeth 1810 and 1816 slide over each other such that less teeth remain engaged. As a result of inward facing teeth 1810 and outward facing teeth 1816 being engaged, roll 1808 can only expand and cannot shrink back in diameter. The cutting elements 1820 on the proximal area of the sheath 1800 cuts through skin and subcutaneous tissue to enable expansion.

After placement of the sheath in the artery, the needle is removed, and an expander is inserted in the sheath to expand it, and is then removed. An advantage of this embodiment is that due to the ratchet mechanism, it resists external pressure and remains patent at its enlarged diameter, Additionally, the optional cutting elements 1820 on its outer surface cut through superficial tissue so that it does not interfere with sheath expansion.

Figure 31A:
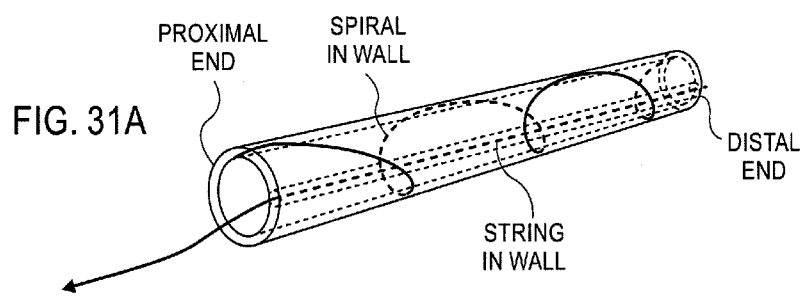
FIGS. 31A-B show three-dimensional views of an alternative embodiment of an expandable sheath in accordance with the principles of the invention.
Figure 31B:
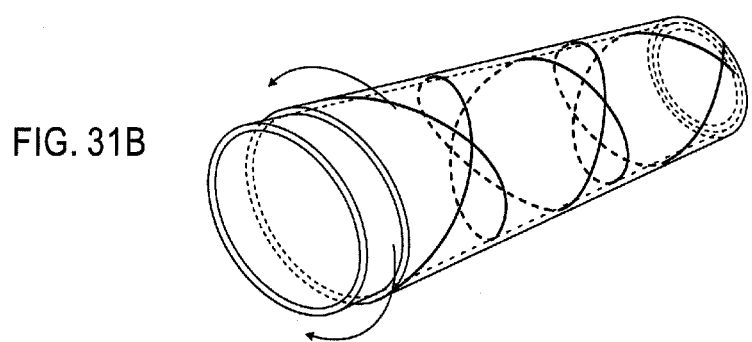

An alternative method of expansion, which relies on a spiral wire within the sheath wall, is described in FIGS. 31A-B. The sheath is shortened by pulling a string connected to its distal end (FIG. 31A), and this causes expansion of the spiral coils and the sheath. Alternatively, the sheath has two layers, each containing a spiral with opposing directions, and when these are rotated towards each other, the sheath shortens and expands (FIG. 31B). Once expanded, the sheath can be used for introducing endovascular devices into the artery.

Additional measures to decrease friction caused by surrounding tissues during insertion may include lubrication of the external aspect of the sheath by a biocompatible lubricant, surface treatment that will render the surface more slippery, as well as other methods known in the art.

Although described herein in the context of vascular access, it is clear to persons skilled in the art that the current invention may be applied to other medical areas. These include but are not limited to the following:

Minimally Invasive Surgery:

The current invention may serve for access to various surgical sites in the body such as to the abdomen in laparoscopic operations, the vertebrae/discs in spinal surgery, etc.

Drains:

Insertion of drains for removal of fluids (blood, exudate, pus etc.) or gases is a common procedure performed on many organs and anatomical structures: the chest—chest drains for traumatic pneumothorax, hemothorax or following thoracic surgery, the abdomen—drainage of ascites or post-operative abscesses, the kidneys—post operative drainage of urine, the urinary bladder—cystostomy for acute urinary retention, collections inside wounds at any site such as the axilla post mastectomy etc.

All these applications would benefit from the easy over the needle/mandrel insertion of a drain at a contracted state and its subsequent expansion for drainage of larger volumes. The expandable sheath may be maintained at an expanded state by insertion of a more rigid sheath of a desired diameter into it.

Urinary Catheter Placement:

Another application of the current invention is for urinary bladder catheterization for Foley catheter placement or procedures in the urinary tract such as ureteroscopy, cystoscopy, stent placement etc. The most pain sensitive part of the urethra is its external orifice. The non-expanded sheath can easily be inserted into the external urethral orifice with minimal pain to the patient. Subsequent insertion of catheters/instruments through it will minimize pain experienced by the patient, as friction will be between the catheter and sheath instead of between the catheter and urethra.

Lacrimal Duct Drainage:

in cases of obstruction of the lacrimal duct, a miniature version of the invention may be used to allow passage of lacrimal fluid into the nasal cavity. Placement of an expandable sheath is expected to cause less discomfort to the patient than a regular fixed diameter sheath.

Tracheal Intubation:

Placement of a tracheal tube could be more easily performed using a small diameter tube for finding and entering the airway, then expanding it along its entire length using a rigid inner tube. This method is described in FIGS. 32A-B.

Figure 32A:
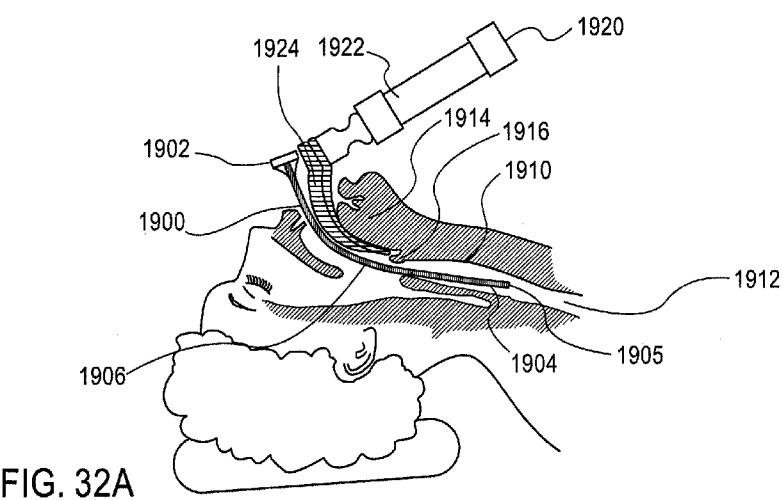
FIGS. 32A-B show use of an expandable sheath for insertion of an endotracheal tube in accordance with the principles of the invention.

More particularly, FIG. 32A shows a longitudinal section of a patient's airway during tracheal intubation showing larynx 1910, tracheal lumen 1912, epiglottis 1916, and tongue 1914. Also shown are a laryngoscope 1920 having handle 1922 and blade 1924 and expandable tracheal sheath 1900 having sheath hub 1902, sheath shaft 1906, sheath distal tip 1904, and sheath lumen 1905.

Figure 32B:
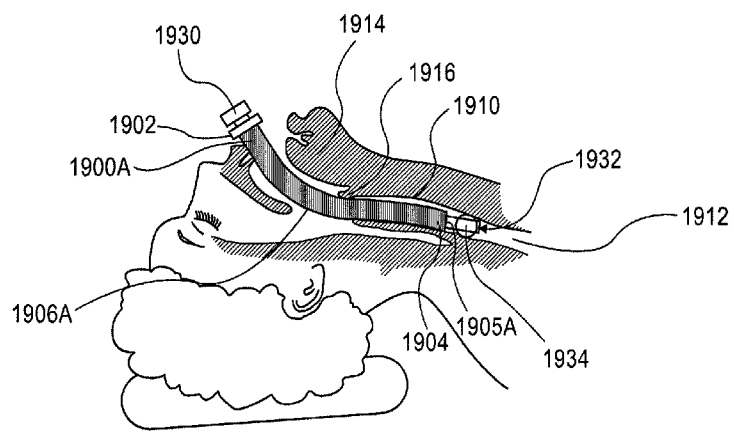

FIG. 32B shows a longitudinal section of a patient's airway after tracheal intubation showing larynx 1910, tracheal lumen 1912, epiglottis 1916, and tongue 1914. Also shown are a tracheal tube 1930 having lumen 1932 and balloon 1934, as well as expanded tracheal sheath 1900*a* having sheath hub 1902, expanded sheath shaft 1906*a*, sheath distal tip 1904 and expanded sheath lumen 1905*a*.

In use, blade 1924 of laryngoscope 1920 is used to lift tongue 1914. Expandable tracheal sheath 1900 is inserted into tracheal lumen 1912. Preferably as described above for various expandable sheath embodiments, tracheal tube 1900 has at least one longitudinal beam made of a malleable material, which enables shaping it with a slight longitudinal curve, which aids in intubation as known in the art. Following insertion of sheath 1900 into tracheal lumen 1912, laryngoscope 1920 is removed and endotracheal tube 1930 is inserted through lumen 1905 of sheath 1900 until its distal tip 1932 extends beyond distal tip 1904 of expanded tracheal sheath 1900*a*. Balloon 1934 of tracheal tube 1930 is inflated to secure it in place.

This embodiment has the advantage that as sheath 1900 has a small non-expanded diameter, its insertion is relatively easy compared with insertion of an endotracheal tube, which has a larger diameter. Additionally, sheath 1900 may assist in replacement of damaged endotracheal tubes without the need for reintubation. Sheath 1900 is held in place by holding sheath hub 1902, thus retaining the correct route into the trachea while endotracheal tube 1930 is removed and replaced. This is especially beneficial as the current practice is to insert amandrel into the endotracheal tube, remove it and reinsert a new tube over the manrel, which exposes the patient to the danger of injury from mandrel placement and from tube reintroduction in the larynx and trachea. In contrast, with use of the method of the invention, sheath 1900 will protect the patient's airway from possible injury that could be caused by reinsertion of the tube.

The current application may also be used for various applications in veterinary medicine.

C. Modifications to Occlusion Catheter

One of the problems with current instrumentation for endovascular occlusion is the large caliber of aortic occlusion balloons, which necessitates placement of large sheaths—usually at least 13 fr sheaths. The large diameter of current balloons is mainly due to the need for having both a working lumen and a lumen for balloon inflation, and due to the volume occupied by the deflated balloon over the catheter.

Embodiments shown in FIGS. 33-34 provide low profile arterial occlusion balloon embodiments wherein the balloon is located distal to the tip of the catheter, which enables crimping it into a much smaller size. Although not regular practice, in the specific emergency situation of exsanguination shock due to battlefield trauma, and more so when using the localizer device of the invention, a balloon may be placed without use of a guidewire, so a catheter having only one lumen for inflating the balloon may be used. Stabilization of the balloon distal to the catheter tip is required in order to enable its insertion into the sheath, as a flail balloon would cause difficulty in such insertion. This may be achieved in several ways.

Figure 33A:
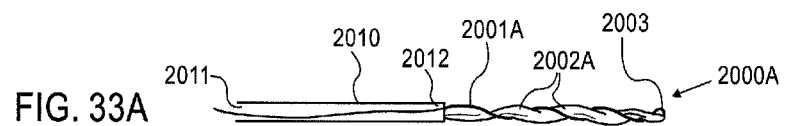
FIGS. 33A-B show side views of an embodiment of the occlusion catheter

FIG. 33A shows a side view of crimped occlusion balloon catheter 2000a consisting of catheter 2010 having lumen 2011, distal tip 2012, crimped balloon 2002a, stabilizing wire 2001a having distal tip 2003. Wire 2001a may be a nitinol wire having a "j" shaped tip as is known in the art, which has been coiled around balloon 2002a in such way as to keep it stable.

Figure 33B:
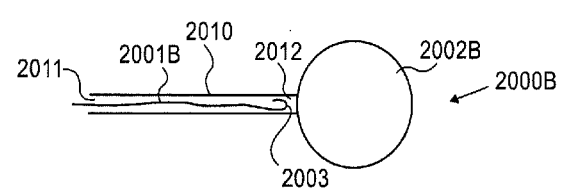

FIG. 33B shows a side view of deployed occlusion balloon catheter 2000b consisting of catheter 2010 having lumen 2011, distal tip 2012, inflated balloon 2002b, retracted stabilizing wire 2001b having distal tip 2003.

As shown in FIG. 33A, in the crimped state, stabilizing wire 2001a is coiled around balloon 2002a so as to hold it stable distal to tip 2012 of catheter 2010. Tip 2003 of wire 2001a is "J" shaped in order to prevent vascular injury by its edge during insertion.

As shown in FIG. 33B, during deployment wire 2001b is retracted, releasing balloon 2002b which is then inflated.

Figure 34A:
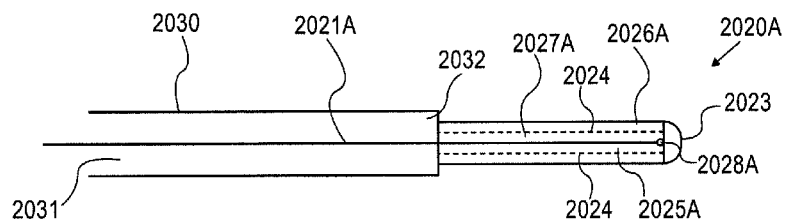
FIGS. 34A-B show side views of an alternative embodiment of the occlusion catheter in accordance with the principles of the invention.
Figure 34B:
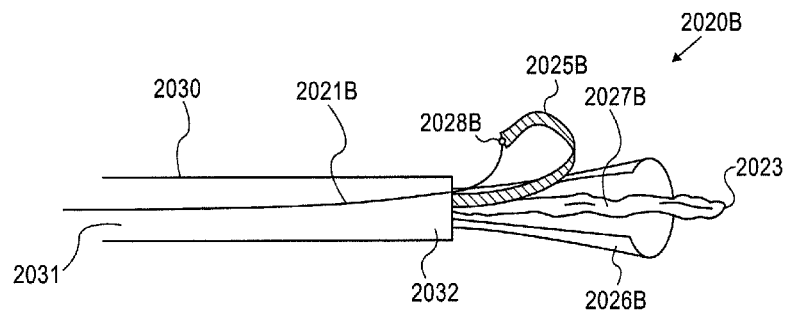

An alternative embodiment is shown in FIGS. 34A-B. In this embodiment, the balloon is held together by a thin wrap (FIG. 34A), which has tearable strip surrounded by perforated tear lines on both sides and has a wire attached to its end. The string is pulled, tearing the strip from the wrap and releasing the balloon for inflation.

More particularly, FIG. 34A shows a side view of occlusion catheter 2020a at crimped and wrapped state, consisting of catheter 2030 having lumen 2031 and distal tip 2032, wrapped balloon 2027a having tip 2023 and covered by intact wrapping 2026a having tearable strip 2025a delineated by perforated tearlines 2024 on each side. Wire 2021a passing through catheter lumen 2031 is attached to distal tip 2028a of tearable strip 2025a.

FIG. 34B shows a side view of occlusion catheter 2020b at crimped unwrapped state, consisting of catheter 2030 having lumen 2031 and distal tip 2032, unwrapped balloon 2027b having tip 2023. Torn wrapping 2026b and torn strip 2025b are seen separated from balloon 2027b. Wire 2021b is attached to distal tip 2028b of torn tearable strip 2025b, and is shown being retracted and tearing away strip 2025b from wrapping 2026b. Balloon 2027b can now be inflated.

In yet another embodiment, the pressure of balloon inflation itself expands balloon 2027a and tears wrapping 2026a at perforated tearlines 2024.

Alternatively, the balloon is manufactured such that it retains a tubular shape and is relatively rigid without any support. Inflation creates enough pressure to change the balloon's shape and inflate it.

Figure 35A:
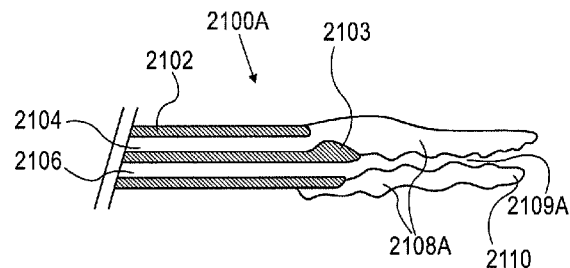
FIGS. 35A-B show a longitudinal section of an embodiment of a balloon catheter having its base on the catheter tip but mostly folding distal to catheter tip in accordance with the principles of the invention in accordance with the principles of the invention.
Figure 35B:
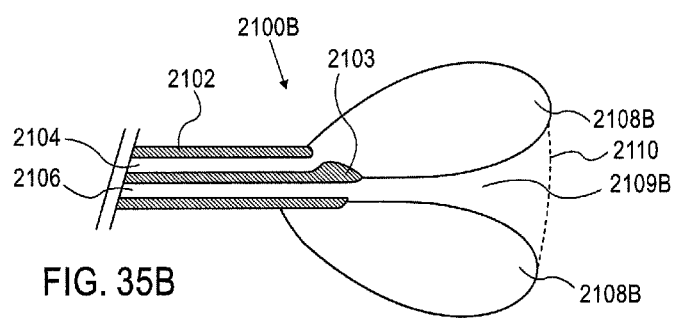

FIG. 35A-B shows a balloon catheter having its base on the catheter tip but mostly folding distal to catheter tip, thus creating a lower profile, while still having a lumen going through the balloon.

More particularly FIG. 35A shows a cross-section of distal part of occlusion catheter 2100a in its deflated state. Catheter 2100a includes catheter 2102 having tip 2103, balloon inflation lumen 2104 and working lumen 2106 extending throughout its length. Balloon 2108a is ring shaped and has lumen 2109a continuous with lumen 2106 of catheter 2102. Balloon 2108a surrounds opening of lumen 2106 at distal tip 2103 of catheter 2102, such that balloon inflation lumen 2104 opens into balloon 2108a. This structure enables crimping of balloon 2108a distal to tip 2103 of catheter 2102, such that most of the balloon material is beyond the tip and does not cause enlargement of its diameter at that point. In this way, a low profile balloon is provided. Deflated balloon 2108a may be stabilized in any of the methods previously described herein.

FIG. 35B shows a cross-section of distal part of occlusion catheter 2100b in its inflated state. Catheter 2100b includes catheter 2102 having tip 2103, balloon inflation lumen 2104 and working lumen 2106 extending throughout its length. Balloon 2108b is ring shaped and has lumen 2109b continuous with lumen 2106 of catheter 2102. Balloon 2108b surrounds opening of lumen 2106 at distal tip 2103 of catheter 2102, such that balloon inflation lumen 2104 opens into balloon 2108b. This structure provides an inflated balloon 2108b with a patent channel into blood vessel via working lumen 2106, which is continuous with lumen 2109b of balloon 2108b.

Figure 36A:
FIGS. 36A-C show a longitudinal section of an embodiment of a catheter with single lumen which can be used for inflation of balloon as well as for measuring pressure beyond the balloon in accordance with the principles of the invention.
Figure 36B:
Figure 36C:

Another embodiment of an occlusion catheter schematically shown in FIG. 36, is a balloon catheter having a single lumen, wherein the working lumen can be used for both inflating the balloon and as a working lumen for measuring, pressure beyond the balloon, fluid administration and drawing blood. This may be achieved for example by having a two way valve within the working lumen adjacent to the opening in the sidewall of said lumen used for inflating the balloon. The two way valve may be set to either of two positions, one allowing fluid communication between the balloon and the proximal working lumen while blocking the distal working lumen and the other position blocking the balloon inflation opening so as to keep the balloon inflated, while allowing fluid communication between the proximal and distal parts of the working lumen. Means for operating such valve may include but are not limited to mechanical means such as a wire extending throughout the length of the balloon catheter, electrical means such as an electronically operable valve, a hydraulically operated valve etc.

Another drawback of current balloon systems is that they require de-airing: prior to use of a balloon, the system is filled with an air-fluid mixture and then all the air is drawn out to make sure no bubbles are left, which might, if they embolize, cause a stroke. This is a simple procedure for an experienced endovascular surgeon at the angio-suite, but cumbersome at the battlefield. The current invention includes a closed system balloon catheter, which arrives pre-filled with fluid and has no openings, so that air cannot be introduced into the system.

Another option for a low profile arterial occlusion catheter is based on a non-inflatable occluder. One such embodiment described in FIGS. 37A-C is a reversed umbrella shaped device, with membranes between its arms.

Figure 37A:
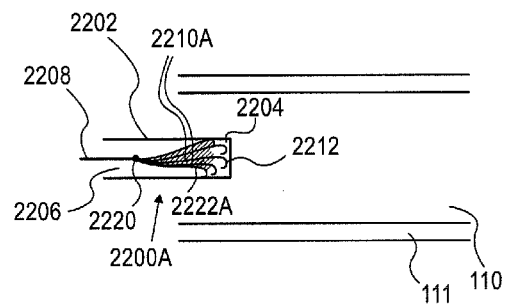
FIGS. 37A-C show longitudinal and cross-sectional views of an alternative embodiment of the occlusion catheter in accordance with the principles of the invention.

More particularly FIG. 37A shows a longitudinal section of occluder 2200a at its crimped state. Shown are vessel lumen 110 and catheter 2202 having lumen 2206 extending therethrough ending at distal tip 2204. Within catheter lumen 2206 is seen occluder 2200a including rigid wire 2208 ending at junction 2220 from which extend distally and radially arms 2210a, which in this figure are seen crimped inside lumen 2206, thus they are parallel to lumen 2206. Arms 2210a end at j tipped endings, which are soft and curved to prevent vessel injury. Between arms 2210a extends membrane 2222a made of a biocompatible sheet such as GORTEX or other materials known in the art.

Figure 37B:
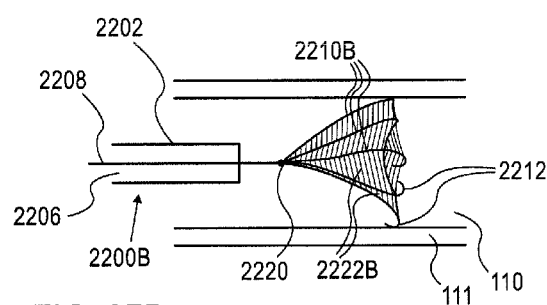

FIG. 37B shows a longitudinal section of occluder 2200b at its deployed state. Shown are vessel lumen 110 and catheter 2202 having lumen 2206 extending therethrough ending at distal tip 2204. Extending through catheter lumen 2206 is seen occluder 2200b including rigid wire 2208 ending at junction 2220 from which extend distally and radially arms 2210b, which in this figure are seen deployed inside vessel 110 and touching its walls 111. Arms 2210*b* end at j tipped endings, which are soft and curved to prevent vessel injury. Between arms 2210*b* extends membrane 2222*b*, in this figure forming an umbrella like structure together with arms 2210*b*, which blocks vessel lumen 110.

Figure 37C:
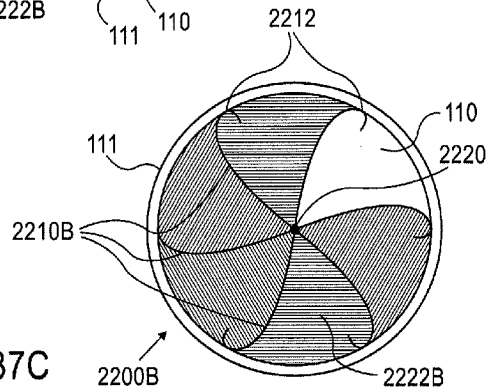

FIG. 37C shows a cross-section of occluder 2200*b* at its deployed state. Shown are vessel lumen 110 and its wall 111, junction 2220 from which extend distally and radially arms 2210*b*, which in this figure are seen deployed inside vessel 110 and touching its walls 111. Arms 2210*b* end at j tipped endings, which are soft and curved to prevent vessel injury. Between arms 2210*b* extends membrane 2222*b*, in this figure forming an umbrella like structure together with arms 2210*b*, which blocks vessel lumen 110.

Figure 38A:
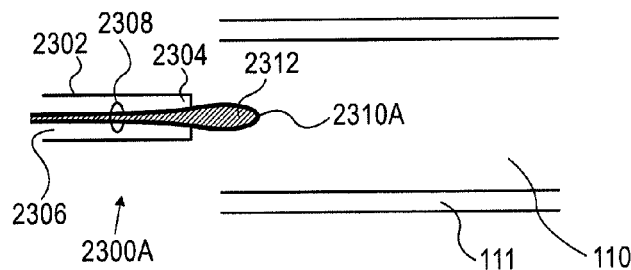
FIGS. 38A-C show longitudinal and cross-sectional views of an alternative embodiment of the occlusion catheter in accordance with the principles of the invention.
Figure 38B:
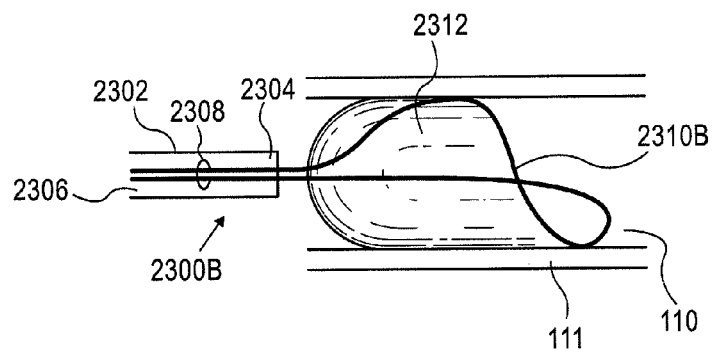
Figure 38C:
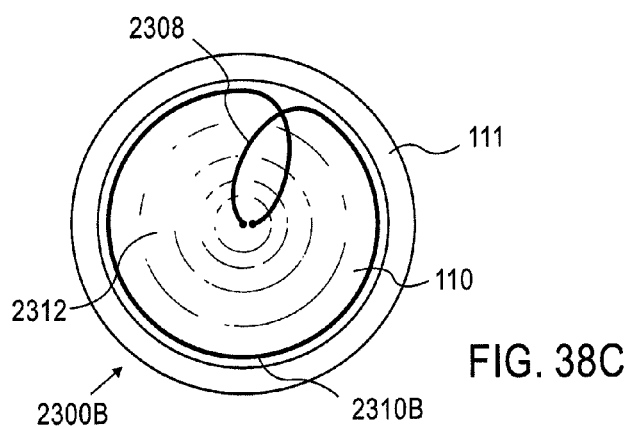

Alternatively, FIGS. 38A-C show an embodiment of an occluder having a single or several wire loops covered by a membrane. More particularly FIG. 38A shows a longitudinal section of occluder 2300*a* at its crimped state. Shown are vessel lumen 110 and catheter 2302 having lumen 2306 extending therethrough ending at distal tip 2304. Within catheter lumen 2306 is seen occluder 2300*a* including wires 2308 ending at crimped wire loop 2310*a*, and membrane 2312 made of a biocompatible sheet such as GORTEX or other materials known in the art, which extends between wires 2308.

FIG. 38B shows a longitudinal section of occluder 2300*b* at its deployed state. Shown are vessel lumen 110 and catheter 2302 having lumen 2306 extending therethrough ending at distal tip 2304. Within catheter lumen 2306 is seen occluder 2300*b* including wires 2308, in this figure deployed in vessel 110 with loop of deployed wire loop 2310*b* touching wall 111 of vessel 110, and membrane 2312 made of a biocompatible sheet such as GORTEX or other materials known in the art, which extend around wire loop 2310*b*.

FIG. 38C shows a cross-section of occluder 2300*b* at its deployed state. Shown are vessel lumen 110 and occluder 2300*b* including wires 2308, in this figure deployed in vessel 110 with loop of deployed wire loop 2310*b* touching wall 111 of vessel 110, and membrane 2312 made of a biocompatible sheet such as GORTEX or other materials known in the art, which extend around wire loop 2310*b*.

It may be of great benefit to perform the aortic occlusion with the occluder located as low in the aorta as possible, i.e. as close as possible to the injury/leakage site. This will prevent major organ systems from being exposed to unnecessary ischemia. For example, if the vascular injury is in a pelvic artery, there is no need for occlusion above the renal arteries. An infrarenal occlusion can be performed and perfusion to the kidneys and bowel may be preserved. Identification of the lowest effective level of occlusion can be done using a shifting balloon with concomitant arterial pressure measurement. Supradiaphragmatic occlusion is initially performed so that arterial pressure proximal to the balloon is restored. The balloon is then moved down the aorta approximately 5 cm at a time and measurements repeated until a fall in pressure is observed. The balloon must then be moved back up to the previously effective point. If a non-inflatable occluder such as described above is used, it may be moved downstream continuously until the pressure fall is observed, as deflation and re-inflation are not necessary.

Alternatively, FIGS. 39A-D describe a long tubular balloon, which can be used to identify the point of hemorrhage and perform an occlusion just above it. Supradiaphragmatic occlusion is performed, and the catheter is retracted, folding back the balloon edge, so that it gradually exposes more of the aorta to blood flow, until blood pressure falls. The balloon is then folded back slightly to move the occlusion above the hemorrhaging vessel.

Figure 39A:
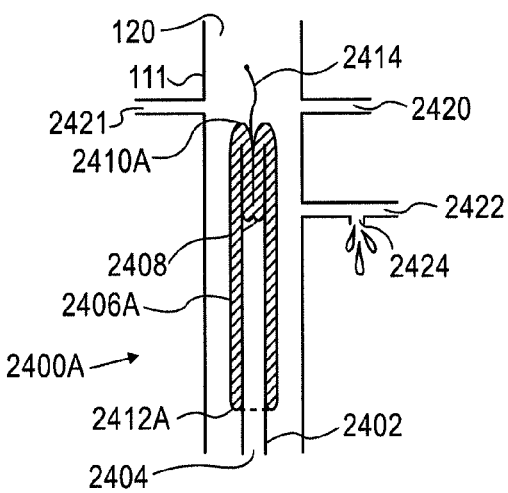
FIGS. 39A-D show longitudinal sections of an alternative embodiment of the occlusion catheter at various stages of deployment in accordance with the principles of the invention.

More particularly FIG. 39A shows a longitudinal section of large blood vessel 120 (e.g. aorta) showing vessel wall 111, distal branches 2420 and 2421 supplying vital organs and hemorrhaging vessel 2422 with point of hemorrhage 2424. Also shown is tubular occluder 2400*a* including catheter 2402 with lumen 2404 and distal end 2408, continuous with deflated tubular balloon 2406*a* having distal tip 2410*a* and proximal tip 2412*a*. Sensor 2414 extends distal to balloon distal tip 2410*a*. In this figure the vessel 2424 is seen hemorrhaging, and tubular occluder is inserted deflated before its inflation. Sensor 2414 is a fiber optic pressure transducer as known in the art but a catheter may be used instead for fluid pressure measurement. Pressure measured by sensor 2414 in an aorta in a state of hemorrhagic shock would be low e.g. 50 mmHg.

Figure 39B:
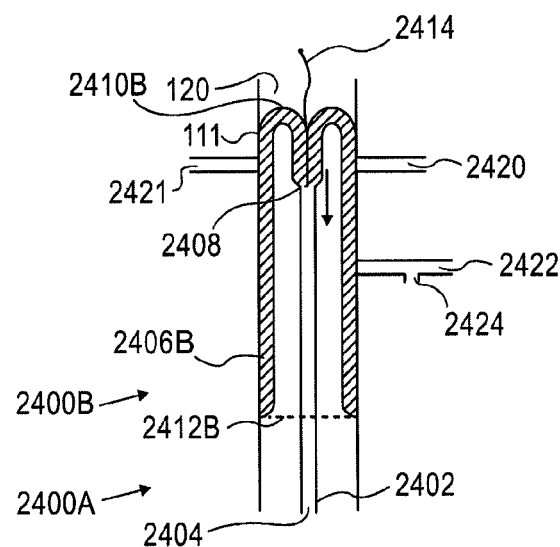

FIG. 39B shows a longitudinal section of large blood vessel 120 (e.g. aorta) showing vessel wall 111, distal branches 2420 and 2421 supplying vital organs and hemorrhaging vessel 2422 with point of hemorrhage 2424. Also shown is inflated tubular occluder 2400*b* including catheter 2402 with lumen 2404 and distal end 2408, continuous with tubular balloon 2406*b* having distal tip 2410*b* and proximal tip 2412*b*. Sensor 2414 extends distal to balloon distal tip 2410*b*. In this figure tubular balloon 2406*b* is inflated as distal as possible (for example at a supradiaphragmatic location) covering vessel 2422 so that hemorrhage from point 2424 has ceased. However, balloon 2406*b* also covers vessels 2420 and 2421, which supply vital organs (e.g. kidneys). Pressure measured by sensor 2414 in an aorta at this stage would be adequate, e.g. 100 mmHg or more. At this time, the user start pulling catheter 2402 proximally so that it moves proximally together with distal balloon tip 2410*b*, exposing the vessel wall around distal tip 2410*b* as it retracts, while balloon 2400*b* in area between distal tip 2410*b* and proximal tip 2412*b* remains adjacent to arterial wall 111, thus preventing blood flow at this area.

Figure 39C:
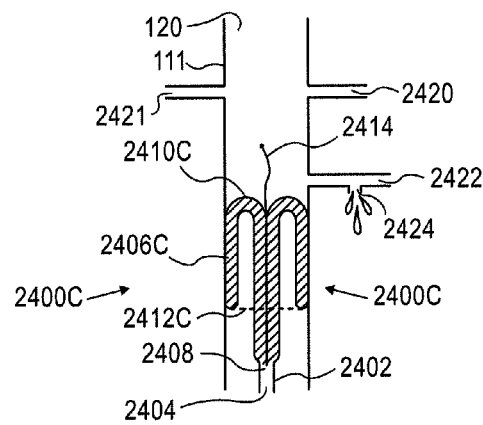

FIG. 39C shows a longitudinal section of large blood vessel 120 (e.g. aorta) showing vessel wall 111, distal branches 2420 and 2421 supplying vital organs and hemorrhaging vessel 2422 with point of hemorrhage 2424. Also shown is inflated tubular occluder 2400*c* including catheter 2402 with lumen 2404 and distal end 2408, continuous with tubular balloon 2406*c* having distal tip 2410*c* and proximal tip 2412*c*. Sensor 2414 extends distal to balloon distal tip 2410*c*. In this figure, tubular balloon tip 2410*c* has been retracted proximal to vessel 2422 so that hemorrhage from point 2424 has been renewed. Pressure measured by sensor 2414 in an aorta at this stage would again fall to a low level e.g. below 80 mmHg. If such fall in pressure occurs, the user starts to advance the catheter 2402 distally again to find the point where blood pressure stabilizes again.

Figure 39D:
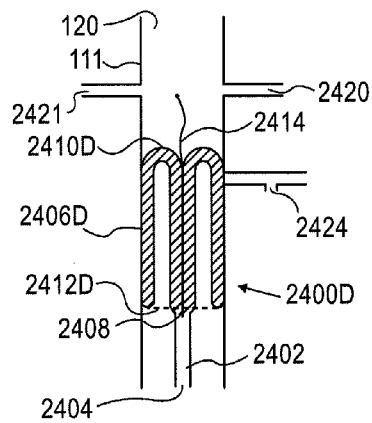

FIG. 39D shows a longitudinal section of large blood vessel 120 (e.g. aorta) showing vessel wall 111, distal branches 2420 and 2421 supplying vital organs and hemorrhaging vessel 2422 with point of hemorrhage 2424. Also shown is inflated tubular occluder 2400*d* including catheter 2402 with lumen 2404 and distal end 2408, continuous with tubular balloon 2406*d* having distal tip 2410*d* and proximal tip 2412*d*. Sensor 2414 extends distal to balloon distal tip 2410*d*. In this figure tubular balloon tip, 2410*d* has been advanced distal to vessel 2422 so that hemorrhage from point 2424 finally ceased. Pressure measured by sensor 2414 in an aorta at this stage would again stabilize to a higher level e.g. above 80 mmHg. The user stops moving the catheter when a stable blood pressure is achieved, and anchors it to prevent its dislodgement.

D. Pressure Control and Monitoring System:

An automated control system capable of inflating and deflating the occlusion balloon can provide additional important advantages. Pressure measurements proximal and distal to the occluder are obtained continuously and compared. The system can alert the user if central blood pressure falls too low for any reason, if balloon pressure falls too low and cannot be fixed—this could indicate balloon leakage or some other technical problem, assuming the patient has reasonable cardiac function. Balloon pressures can be kept at the lowest required level, thus avoiding possible injury to the aorta.

Another benefit of this system is use of automated intermittent pressure release for prevention of ischemia. The occlusion may be released or partially released every few minutes, so that the ischemic body parts may receive some perfusion without continuous hemorrhage.

An expandable sheath in accordance with one embodiment of the invention has a decreasing diameter going from the proximal to the distal end. A sheath hub, which may be constructed of a clear plastic, is attached to the distal end of the expandable sheath body. A needle passes through the sheath body. The sheath body may be constructed of a flexible material.

The distal end of an expandable sheath in accordance with one embodiment of the invention has a needle passing through the distal end. The distal end has a short slit. The expandable sheath body, through which the needle is passing, has a decreasing diameter going from the proximal to the distal end.

Another embodiment of an expandable sheath in accordance with one embodiment of the invention is expandable sheath body, which has a decreasing diameter going from the proximal to the distal end. A needle which may be made from plastic may pass through the expandable sheath body.

Figure 44:
FIG. 44 is a picture of an embodiment of a vessel cannulation device in accordance with principles of the invention.
Figure 45:
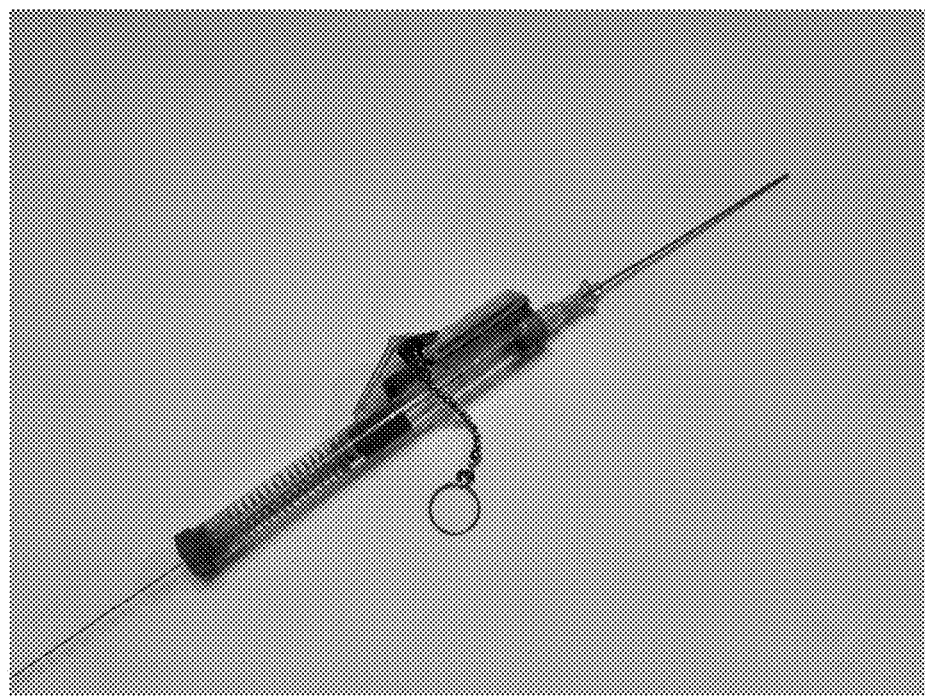
FIG. 45 is a picture of an embodiment of a vessel cannulation device in accordance with principles of the invention.

FIGS. 44 and 45 show different views of the same embodiment of the cannulation device of the invention. Shown in FIGS. 44 and 45 are a vessel cannulation device having a cannulation device body, a pressure chamber, a pressure sensor and a guidewire advancing member.

The cannulation device has a cannulation device body having a distal and proximal end. A needle having a lumen is shown disposed on the distal end. A cap is shown on the proximal end of the cannulation device body. The cannulation device body is configured for passing a guidewire. A guidewire is shown passing through the proximal end of the cannulation device body. At the distal end of the body, the device includes a pressure chamber, which may have a seal on it at proximal end. The pressure chamber is in fluid communication with the lumen of the needle. Also in fluid communication with the pressure chamber is a diaphragm, which is pressure operable. The diaphragm is in contact with a lever. The device includes an expandable member (such as e.g. a spring) having a proximal and a distal end, whose proximal is in contact with the seal at the proximal end. The device further includes an advancing member located at the distal end of the expandable member. The expandable member and advancing member are configured for passing the guidewire. The expandable member is operable via a lever which is connected to the pressure operable diaphragm. The lever further comprises a removable locking mechanism which prevents operation of the device. The tip of the device body is shown having slight taper. When in use the expandable member is provided in a compressed state held in place by advancing member. In use when the needle of the device encounters and punctures a blood vessel, blood (e.g. a fluid) enters the device which pressurizes the pressure chamber. In response to pressurization of the pressure chamber, the diaphragm moves. Movement of the diaphragm causes operation of the lever, which releases the advancing member as a result of which the guidewire is advanced.

Although the foregoing description is directed to the preferred embodiments of the invention, it is noted that other variations and modifications will be apparent to those skilled in the art, and may be made departing from the spirit or scope of the invention. Moreover, features described in connection with one embodiment of the invention may be used in conjunction with other embodiments, even if not explicitly stated above. The present invention may be embodied in other specific forms without departing from its spirit or essential characteristics. The described embodiments are to be considered in all respects only as illustrative and not restrictive.

What is claimed is:

1. A vessel cannulation device comprising:
   a cannulation device body having
   a distal end and proximal end,
   a pressure chamber,
   a guidewire lumen configured to receive a guidewire,
   a pressure sensor operatively coupled to the pressure chamber;
   a guidewire advancing member configured for advancing a guidewire through the guidewire lumen, wherein the guidewire advancing member is operably coupled to the pressure sensor; and
   a needle on the distal end of the device body, wherein the needle is coupled to the pressure chamber,
   wherein the device is configured to automatically advance a guidewire in response to a fluid acting on the pressure sensor, whereby the pressure sensor causes the guidewire advancing member to advance the guidewire.

2. The vessel cannulation device of claim 1, wherein the pressure sensor is a pressure operable diaphragm.

3. The vessel cannulation device of claim 2, wherein the pressure operable diaphragm is located on the exterior of the cannulation body and connected to the pressure chamber.

4. The vessel cannulation device of claim 1, wherein the needle is fluidly coupled to the pressure chamber.

5. The cannulation device of claim 1, further comprising a backplate covering the device body at the proximal end of the device body having an opening configured for passing the guidewire.

6. The cannulation device of claim 1, wherein the guidewire advancing member comprises:
   a large compressible member in contact with a backplate configured for passing a guidewire through the cannulation device;
   a gripper in connection with the large compressible member having an opening configured for passing a guidewire through the cannulation device, wherein the gripper is configured to engage and grip the guidewire;
   a small compressible member in connection with the gripper configured for passing a guidewire through the cannulation device; and
   a slidable member having a proximal end, a distal end and an opening configured for passing a guidewire through the cannulation device, wherein the proximal end of the slidable member is configured to be in connection with and surround the small compressible member, wherein the slidable member is positioned to be in connection with at least one side opening of the cannulation device and wherein the slidable member is configured to accommodate a lever; and the cannulation device further comprising:

an operable lever configured to pass through the at least one side opening and to be in connection with the slidable member, wherein the lever is in connection with the pressure sensor, such that pressure applied to the pressure sensor operates the operable lever.

7. The vessel cannulation device of claim 1, wherein the pressure chamber is partially prefilled with biologically acceptable fluid.

8. The vessel cannulation device of claim 7, wherein the prefilled fluid shortens response time.

9. A kit comprising:
the vessel cannulation device of claim 1;
an expandable sheath;
an occlusion catheter; and
a tip localization device.

10. A system for performing endovascular aortic occlusion comprising:
the vessel cannulation device of claim 1;
an expandable sheath;
an occlusion catheter; and
a tip localization device.

11. A system for treating hemorrhagic shock comprising the vessel cannulation device of claim 1;
an expandable sheath;
an occlusion catheter; and
a tip localization device.

12. A cannulation device comprising:
a housing having a distal end with a distal tip and a proximal end;
a lumen passing through at least the distal tip;
a sensor coupled to the lumen, the sensor being configured to sense a physiologic parameter, wherein the physiological parameter is a blood pressure; and
a blunting device advancing member configured to advance a blunting device, wherein the blunting device is operably coupled to the sensor and the blunting device comprises at least one guidewire,
wherein the blunting device advancing member is configured to automatically advance the blunting device in response to the sensor detecting the physiologic parameter within a pre-determined range.

13. The cannulation device of claim 12, wherein the sensor is a pressure sensor, a photoelectric sensor, a resistance sensor, or an ultrasonic sensor.

14. The cannulation device of claim 12, wherein the blunting device advancing member is configured to advance the blunting device when the sensor detects a blood pressure between 5-250 mm Hg.

15. The cannulation device of claim 12, wherein the sensor is configured to detect an arterial pressure or a venous pressure.

16. The cannulation device of claim 15, wherein the blunting device advancing member is configured to advance the blunting device when the sensor detects the venous pressure.

17. The cannulation device of claim 16, wherein the venous pressure is between 5-20 mm Hg.

18. The cannulation device of claim 15, wherein the blunting device advancing member is configured to advance the blunting device when the sensor detects the arterial pressure.

19. The cannulation device of claim 18, wherein the arterial pressure is between 20-250 mmHg.

20. The cannulation device of claim 12, wherein the sensor is a membrane or a pressure-operable diaphragm.

21. The cannulation device of claim 12, wherein device further comprises one or more ultrasound transducers.

22. The cannulation device of claim 12, wherein the device further comprises an imaging system to obtain images of the vessel.

23. The cannulation device of claim 12, wherein the blunting device further comprises a sheath.

24. The cannulation device of claim 12, wherein upon the sensor detecting that the physiologic parameter within a pre-determined range, the device is configured to automatically pass the blunting device into the vessel.

25. The cannulation device of claim 12, wherein upon the sensor detecting that the physiologic parameter within a pre-determined range, the device is configured to immediately automatically pass the blunting device comprising a guidewire through the distal tip of the needle into the vessel, the guidewire extending a distance beyond the distal tip of the needle preventing the needle from puncturing a wall of the vessel.

26. A method of cannulating at least one of an artery and a vein using the device of claim 12.

* * * * *